United States Patent
Javaherian et al.

(10) Patent No.: US 11,845,784 B2
(45) Date of Patent: Dec. 19, 2023

(54) MEANS AND METHODS FOR THE TREATMENT OF ANGIOGENESIS-, FIBROSIS- AND CANCER-RELATED DISEASES WITH PROTEIN OLIGOMERS COMPRISING NC-1-FC

(71) Applicant: Heidelberg Biotech GmbH, Heidelberg (DE)

(72) Inventors: Kashi Javaherian, Heidelberg (DE); Jürgen Debus, Heidelberg (DE); Amir Abdollahi, Heidelberg (DE)

(73) Assignee: Heidelberg Biotech GmbH, Heidelberg (DE)

( * ) Notice: Subject to any disclaimer, the term of this patent is extended or adjusted under 35 U.S.C. 154(b) by 319 days.

(21) Appl. No.: 17/048,158

(22) PCT Filed: Apr. 16, 2019

(86) PCT No.: PCT/EP2019/059747
§ 371 (c)(1),
(2) Date: Oct. 16, 2020

(87) PCT Pub. No.: WO2019/201892
PCT Pub. Date: Oct. 24, 2019

(65) Prior Publication Data
US 2021/0363225 A1 Nov. 25, 2021

(30) Foreign Application Priority Data
Apr. 17, 2018 (EP) .................................. 18167832

(51) Int. Cl.
C07K 14/78 (2006.01)
A61K 38/00 (2006.01)
A61P 19/04 (2006.01)
A61P 35/00 (2006.01)
A61K 45/06 (2006.01)

(52) U.S. Cl.
CPC .............. *C07K 14/78* (2013.01); *A61K 45/06* (2013.01); *A61P 19/04* (2018.01); *A61P 35/00* (2018.01); *A61K 38/00* (2013.01)

(58) Field of Classification Search
None
See application file for complete search history.

(56) References Cited

U.S. PATENT DOCUMENTS

| | | |
|---|---|---|
| 7,078,485 B2 | 7/2006 | Luo et al. |
| 7,524,811 B2 | 4/2009 | Folkman et al. |
| 8,703,908 B2 | 4/2014 | Lo et al. |
| 9,200,060 B2 | 12/2015 | Kannan et al. |
| 2009/0041770 A1 | 2/2009 | Chamberlain et al. |
| 2013/0165634 A1 | 6/2013 | Lo et al. |
| 2013/0177555 A1 | 7/2013 | Wilkinson et al. |

FOREIGN PATENT DOCUMENTS

| | | | |
|---|---|---|---|
| EP | 2561888 A1 | 2/2013 | |
| WO | 99/62944 A2 | 12/1999 | |
| WO | 2013026913 A2 | 2/2013 | |
| WO | 2013096291 A2 | 6/2013 | |
| WO | 2016040622 A1 | 3/2016 | |
| WO | 2016071377 A1 | 5/2016 | |
| WO | 2017093569 A1 | 6/2017 | |
| WO | WO-2017093569 A1 * | 6/2017 | ............... A61P 1/16 |
| WO | 2017151971 A2 | 9/2017 | |

OTHER PUBLICATIONS

Sasorith S and Lefranc M "Knobs-into-holes amino acid changes" The IMGT Biotechnology page. https://www.imgt.org/IMGTbiotechnology/Knobs-into-holes_IgG.html. (Year: 2013).*
Nobuhiro Abe et al.; Identification of a Novel Collagen Chain Represented by Extensive Interruptions in the Triple-Helical Region; Biochemical and Biophysical Research Communications; Oct. 29, 1993; 7 pages; vol. 196, No. 2.
Stephen F. Altschul et al.; Basic Local Alignment Search Tool; J. Mol. Biol.; 1990; 8 pages; vol. 215.
Gabriele Bergers et al.; Effects of Angiogenesis Inhibitors on Multistage Carcinogenesis in Mice; Science; Apr. 30, 1999; 5 pages; vol. 284.
Daniel J. Capon et al.; Designing CD4 Immunoadhesins for AIDS Therapy; Nature; Feb. 9, 1989; 7 pages; vol. 337.
Xiaoying Chen et al.; Fusion Protein Linkers: Property, Design and Functionality; Adv Drug Deliv Rev.; Oct. 15, 2013; 32 pages; vol. 65, No. 10.
Shan Chung et al.; Characterization of In Vitro Antibody-Dependent Cell-Mediated Cytotoxicity Activity of Therapeutic Antibodies—Impact of Effector Cells; Journal of Immunological Methods; 2014; 13 pages; vol. 407.
William F. Dall'Acqua et al.; Properties of Human IgG1s Engineered for Enhanced Binding to the Neonatal Fc Receptor (FcRn); Journal of Biological Chemistry; Aug. 18, 2006; 12 pages; vol. 281, No. 33.
Yuan-Hua Ding et al.; Zinc-Dependent Dimers Observed in Crystals of Human Endostatin; Proc. Natl. Acad. Sci. USA; Sep. 1998; 6 pages; vol. 95.

(Continued)

*Primary Examiner* — Sudhakar Katakam
*Assistant Examiner* — Zachary J Miknis
(74) *Attorney, Agent, or Firm* — Taft Stettinius & Hollister LLP

(57) ABSTRACT

The present invention pertains to a method for producing a protein oligomer comprising at least two, and preferably three heterodimeric human NC-I-Fc proteins, the method comprising: a) culturing a host cell expressing (i) a fusion protein comprising, from N- to C-terminus, human NC-1 from collagen 18 fused to human IgGI Fc with "knob" mutations, or human IgGI Fc with "knob" mutations fused to human NC-1 from collagen 18, and (ii) human IgGI Fc with "hole" mutations, under conditions which allow the formation of a protein oligomer comprising at least two, and preferably three heterodimeric human NC-1-Fc proteins, and wherein the fusion protein of (i) and the human IgGI Fc with "hole" mutations of (ii) are expressed in a ratio of 2:1 or higher, and b) obtaining the protein oligomer comprising at least two, and preferably three heterodimeric human NC-1-Fc proteins.

Figure 3:
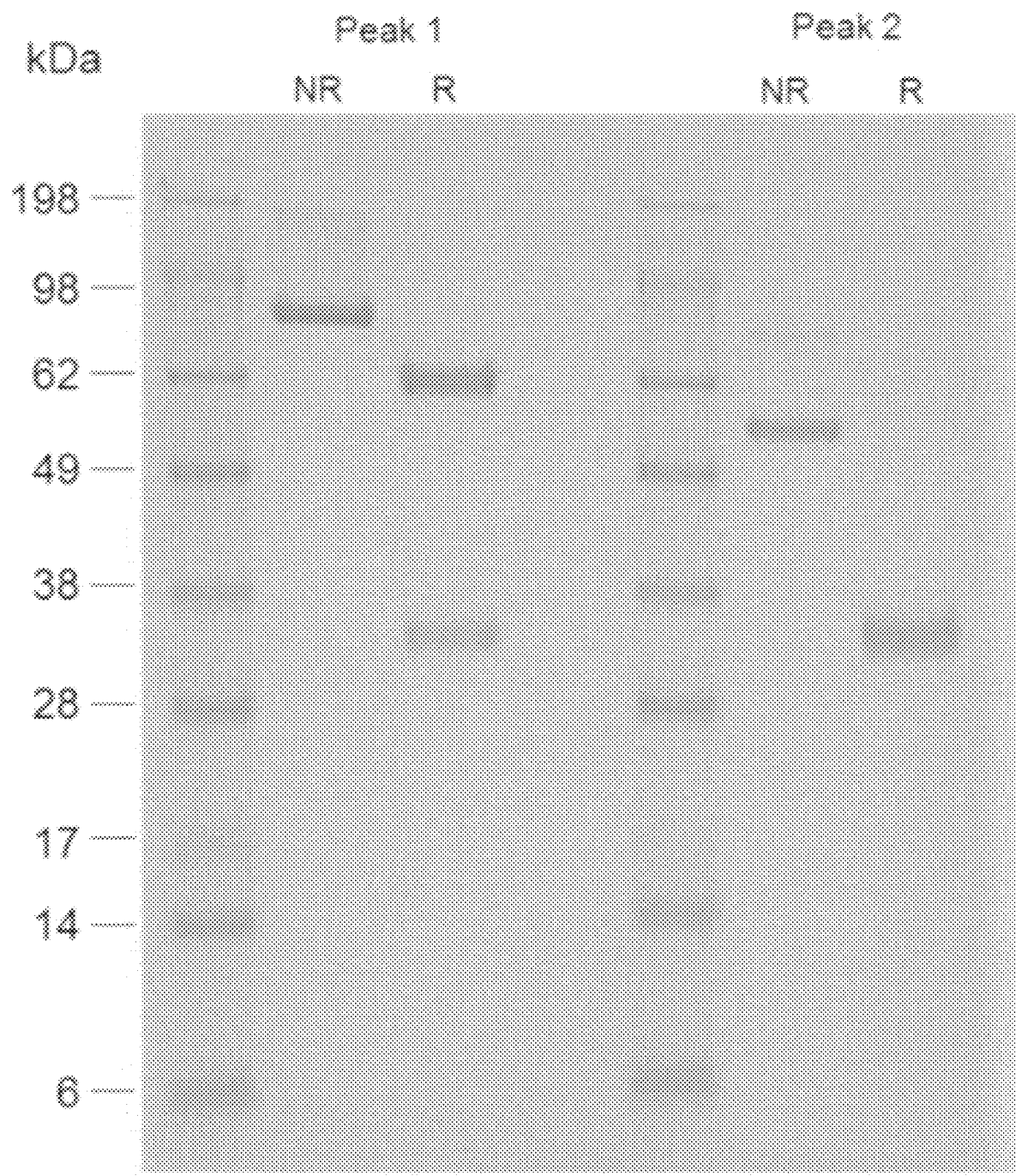

3 Claims, 26 Drawing Sheets
Specification includes a Sequence Listing.

(56) References Cited

OTHER PUBLICATIONS

M.S. Gordon et al.; Phase I Safety and Pharmacokinetic Study of Recombinant Human Anti-Vascular Endothelial Growth Factor in Patients with Advanced Cancer; Journal of Clinical Oncology; Feb. 1, 2001; 8 pages; vol. 19, No. 3.
Ritva Heljasvaara et al.; Generation of Biologically Active Endostatin Fragments from Human Collagen XVIII by Distinct Matrix Metalloproteases; Elsevier; Experimental Cell Research; 2005; 14 pages; 14 pages; vol. 307.
D.G. Higgins; Pubmed_Result.txt; Cabios; 1989; 1 page.
Jocelyn Holash et al.; VEGF-Trap: A VEGF Blocker with Potent Antitumor Effects; PNAS; Aug. 20, 2002; 6 pages; vol. 99, No. 17.
Calvin J. Kuo et al.; Oligomerization-Dependent Regulation of Motility and Morphogenesis by the Collagen XVIII NC1/Endostatin Domain; The Journal of Cell Biology; Mar. 19, 2001; 14 pages; vol. 152, No. 6.
Aran F. Labrijn et al.; Therapeutic IgG4 Antbodies Engage in Fab-arm Exchange with Endogenous Human IgG4 in Vivo; Nature Biotechnology; Aug. 2009; 7 pages; vol. 27, No. 8.
Tong-Young Lee et al.; Linking Antibody Fc Domain to Endostatin Significantly Improves Endostatin Half-Life and Efficacy; Cancer Therapy: Preclincal; Clin Cancer Res; Mar. 1, 2008; 7 pages; vol. 14, No. 5.
Kin-Ming Lo et al.; High Level Expression and Secretion of Fc-X Fusion Proteins in Mammalian Cells; Protein Engineering; 1998; 6 pages; vol. 11, No. 6.
Saul B. Needleman et al.; A General Method Applicable to the Search for Similarities in the Amino Acid Sequence of Two Proteins; J. Mol. Biol.; 1970; 11 pages; vol. 48.
Marijn Van Der Neut Kolfschoten et al.; Anti-Inflammatory Activity of Human IgG4 Antibodies by Dynamic Fab Arm Exchange; Science; Sep. 14, 2007; 5 pages; vol. 317.
Suk P. Oh et al.; Cloning of cDNA and Genomic DNA Encoding Human Type XVIII Collagen and Localization of the a1(XVIII) Collagen Gene to Mouse Chromosome 10 and Human Chromosome 21; Genomics; 1994; 6 pages; vol. 19.
Suk Paul Oh et al.; Isolation and Sequencing of cDNAs for Proteins with Multiple3 Domains of Gly-Xaa-Yaa Repeats Identify a Distinct Family of Collagenous Proteins; Proc. Natl. Acad. Sci. USA; May 1994; 5 pages; vol. 91.
Michael S. O'Reilly et al.; Endostatin: An Endogenous Inhibitor of Angiogenesis and Tumor Growth; Cell; Jan. 24, 1997; 9 pages; vol. 88.
Bhavin S. Parekh et al.; Development and Validation of an Antibody-Dependent Cell-Mediated Cytotoxicity—Reporter Gene Assay; Landes Bioscience; May/Jun. 2012; 9 pages.
Takako Sasaki et al.; Structure, Function and Tissue Forms of the C-Terminal Globular Domain of Collagen XVIII Containing the Angiogenesis Inhibitor Endostatin; The EMBO Journal; 1998; 8 pages; vol. 17, No. 15.
Lu Shan et al.; Generation and Characterization of an IgG4 Monomeric Fc Platform; PLOS One; Aug. 1, 2016; 18 pages.
Temple F. Smith et al.; Comparison of Biosequences; Advances in Applied Mathematics; 1981; 8 pages; vol. 2.
Minoru Tada et al.; Development of a Cell-Based Assay Measuring the Activation of FcyRIIa for the Characterization of Therapeutic Monoclonal Antibodies; PLOS One; Apr. 2014; 9 pages; vol. 9, Issue 4.
Robert M. Tjin Tham Sjin et al.; A 27-Amino-Acid Synthetic Peptide Corresponding to the Nh2 Terminal Zinc-Binding Domain of Endostatin is Responsible for Its Antitumor Activity; Cancer Res; May 1, 2005; 9 pages; vol. 65, No. 9.
Josef Vagner et al.; Peptidomimetics, A Synthetic Tool of Drug Discovery; Curr Opin Chem Biol; Jun. 2008; 10 pages; vol. 12, No. 3.
Ian C. Wilkinson et al.; Monovalent IgG4 Molecules Immunoglobulin Fc Mutations that Result in a Monomeric Structure; Landes Bioscience; May/Jun. 2013; 12 pages; vol. 5, Issue 3.
Makiko Yamashita et al.; A Novel Method for Evaluating Antibody-Dependent Cell-Mediated Cytotoxicity by Flowcytometry Using Cryopreserved Human Peripheral Blood Mononuclear Cells; Scientific Reports; Jan. 27, 2016; 10 pages.
Tianlei Ying et al.; Monomeric IgG1 Fc Molecules Displaying Unique Fc Receptor Interactions that are Exploitable to Treat Inflammation-Mediated Diseases; Landes Bioscience; Sep./Oct. 2014; 10 pages; vol. 6, No. 5.
Thomas Boehm et al.; Zinc-Binding of Endostatin is Essential for Its Antiangiogenic Activity; Biochemical and Biophysical Research Communications; 1998; 5 pages; vol. 252.
International Search Report; European Patent Office; International Application No. PCT/EP2019/059747; dated Aug. 29, 2019; 8 pages.
Written Opinion of the International Searching Authority; European Patent Office; International Application No. PCT/ EP2019/059747; dated Aug. 29, 2019; 9 pages.
Tianlei Ying et al.; Soluble Monomeric IgG1 Fc*; The Journal of Biological Chemistry; Jun. 1, 2012; 10 pages; vol. 287 No. 23.
European Office Action, European Patent Office, European Patent Application No. 19716928.7, dated Sep. 29, 2022, 4 pages.

* cited by examiner

Figure 1

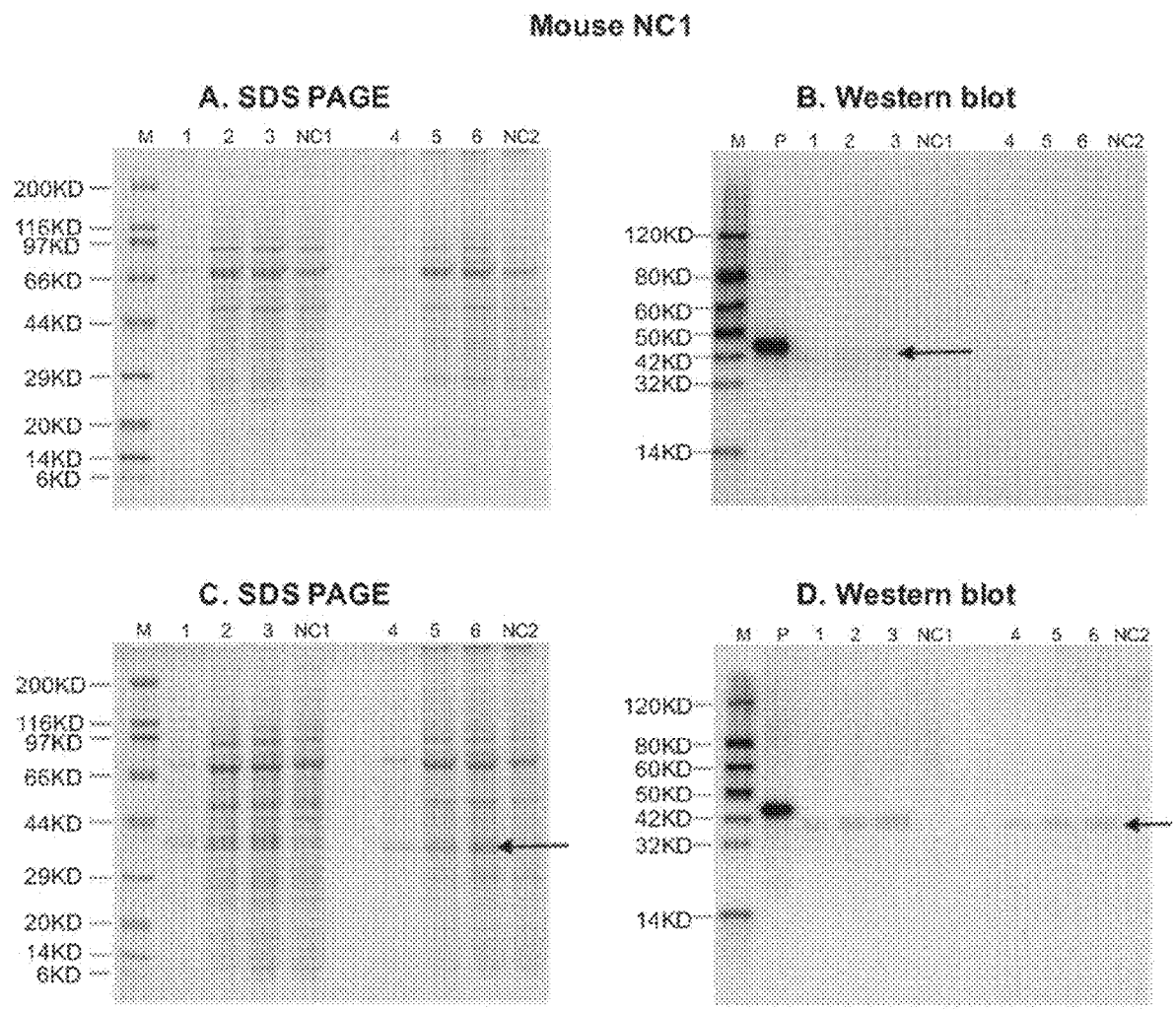

Fig. 1. SDS-Page (left) and Western blot (right) analysis of Mouse NC1 and Human NC1 from cell culture supernatant Lane M: Marker
Lane 1~3: Cell culture supernatant from day 2, 4 and 5 post-transfection under a reducing condition
Lane 4~6: Cell culture supernatant from day 2, 4 and 5 post-transfection under a non-reducing condition
Lane NC1: Negative control under a reducing condition
Lane NC2: Negative control under a non-reducing condition
Primary antibody: Mouse-anti-his mAb (GenScript, Cat.No.A00186)

Figure 2

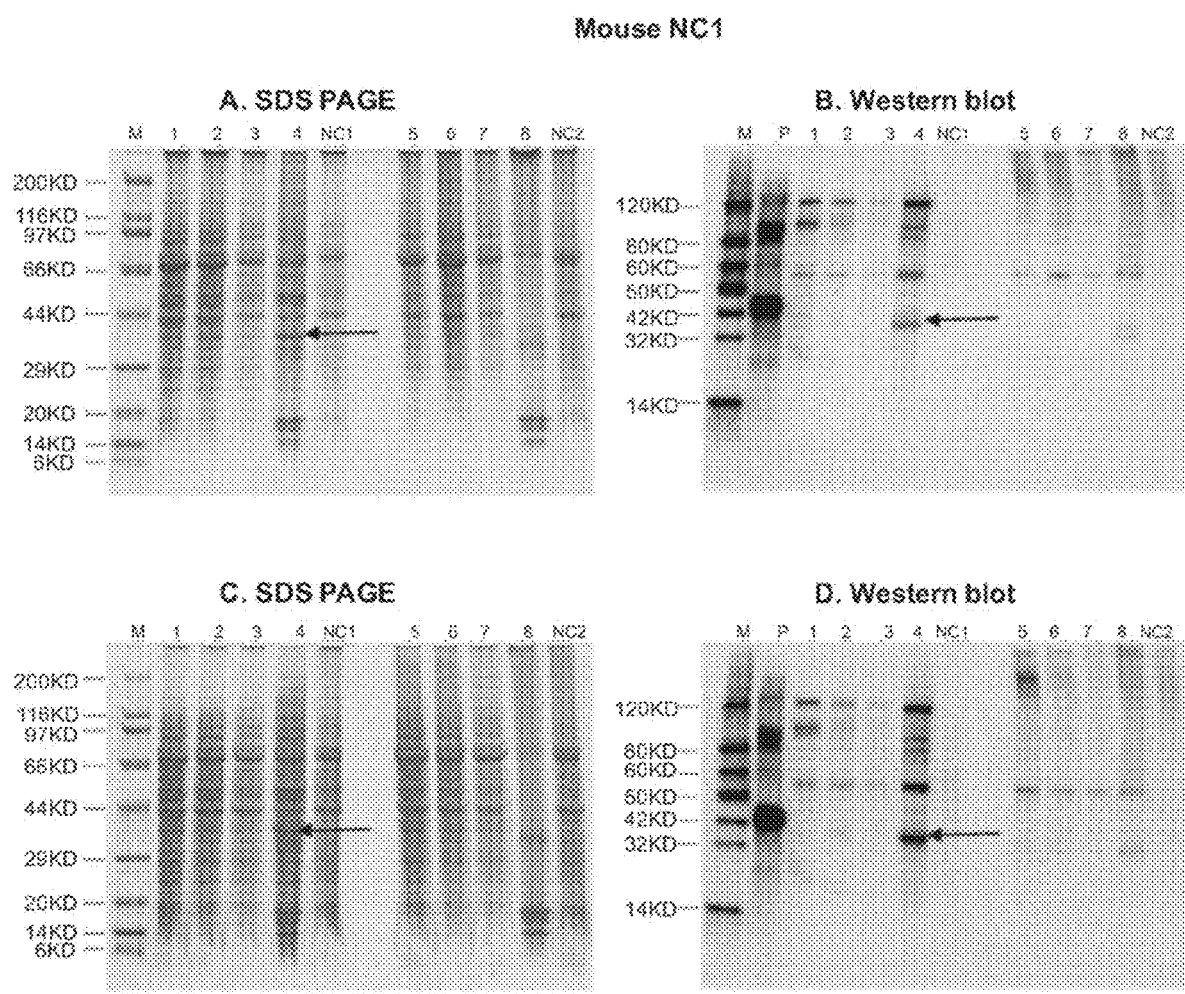

Fig. 2. SDS-Page analysis and Western blot analysis of cell lysates of Mouse NC1 and Human NC1
Lane M: Marker
Lane 1~3: Cell lysate from day 2, 4 and 5 post-transfection under a reducing condition
Lane 4: Cell debris from day 4 post-transfection under a reducing condition
Lane 5~7: Cell lysate from day 2, 4 and 5 post-transfection under a non-reducing condition
Lane 8: Cell debris from day 4 post-transfection under a non-reducing condition
Lane NC1: Negative control under a reducing condition
Lane NC2: Negative control under a non-reducing condition
Primary antibody: Mouse-anti-his mAb (GenScript, Cat.No.A00186)

| Retention Time (min) | |
|---|---|
| Degradation Peak (peak 1) | 13.057 |
| HCP (10.1%) | 16.325 |
| DS2 (10.0.10%) | 16.298 |
| DS1 (70.0%) | 16.164 |
| Monomer | 18.261 |
| Conformational Isomer (peak 2) | 18.717 |
| Dimer of Species | 18.693 |
| Gel Related Species | 20.752 |

Figure 4

Figure 8
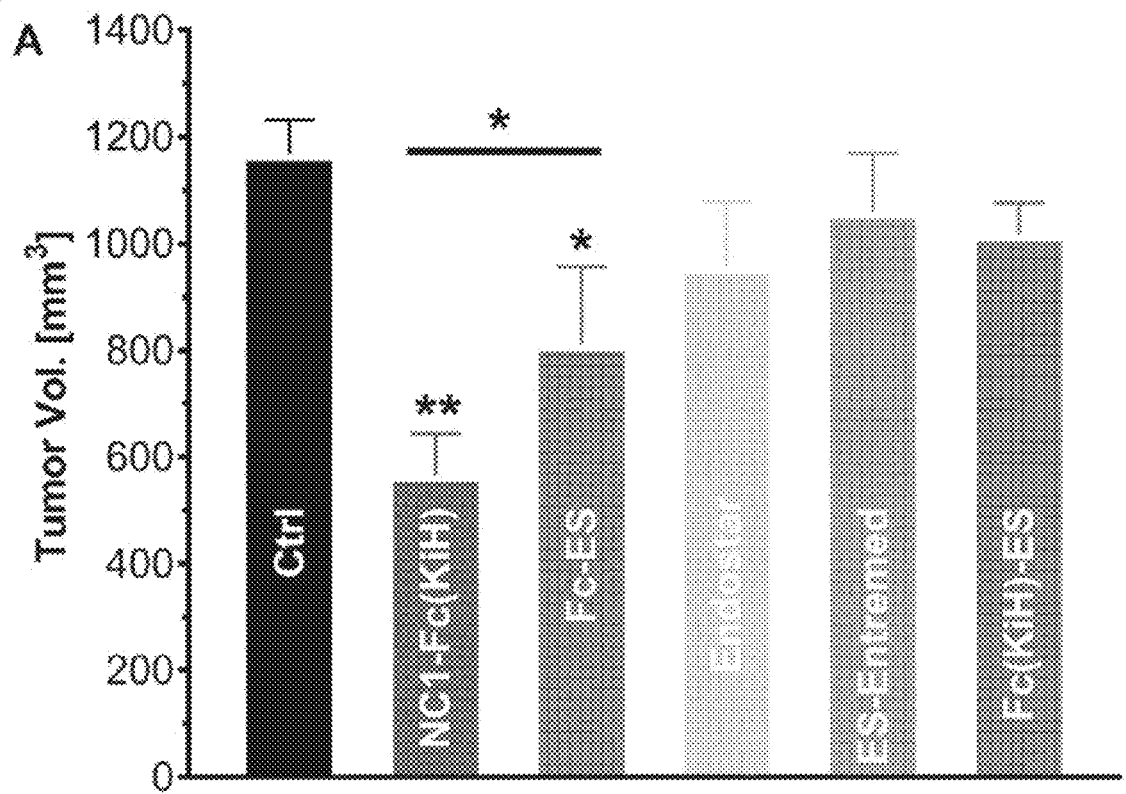
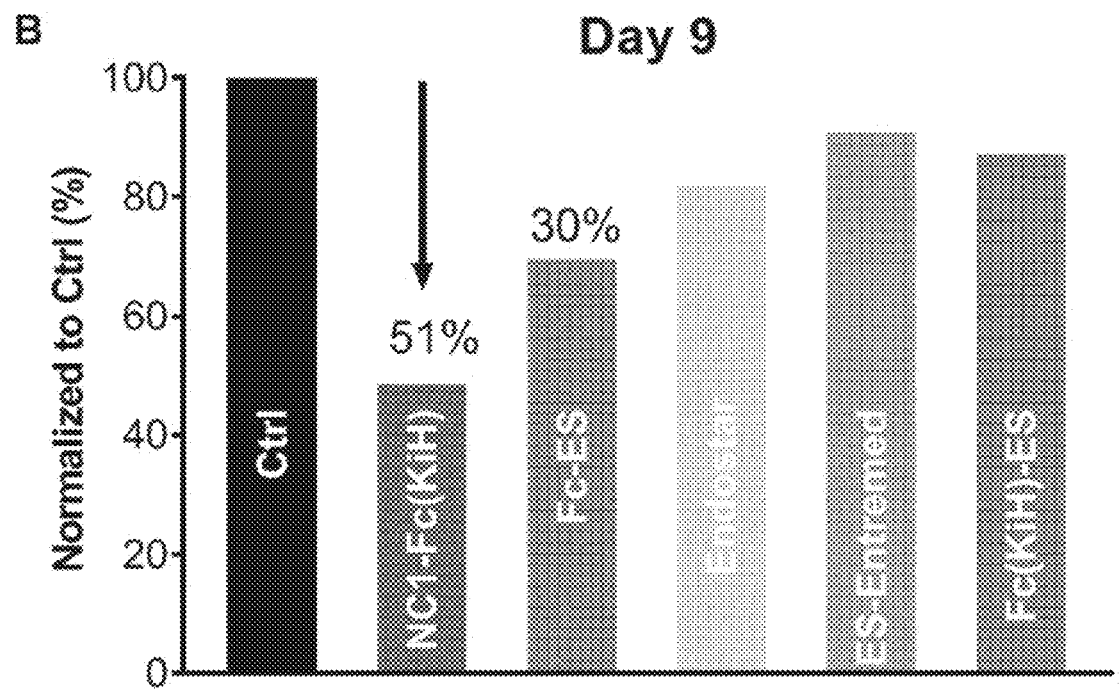

Figure 15
A
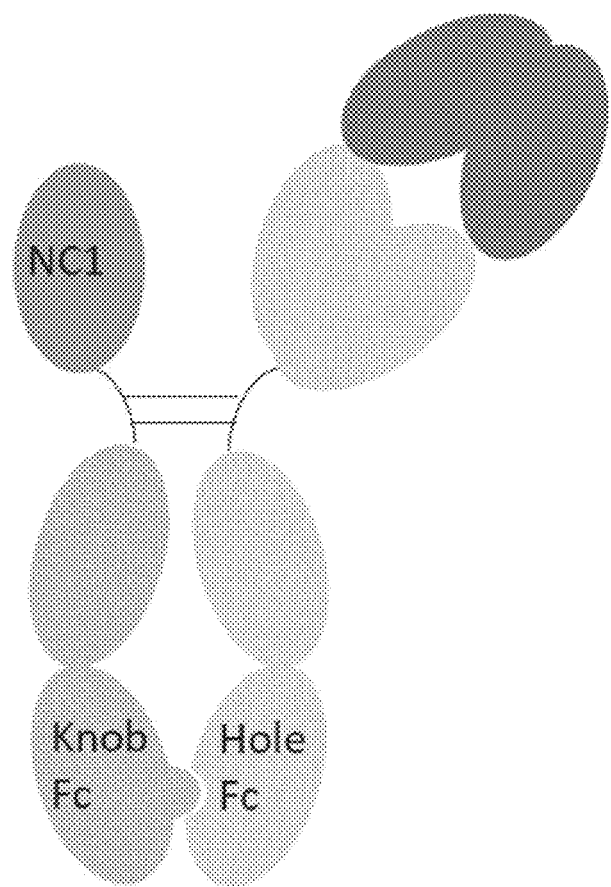
B
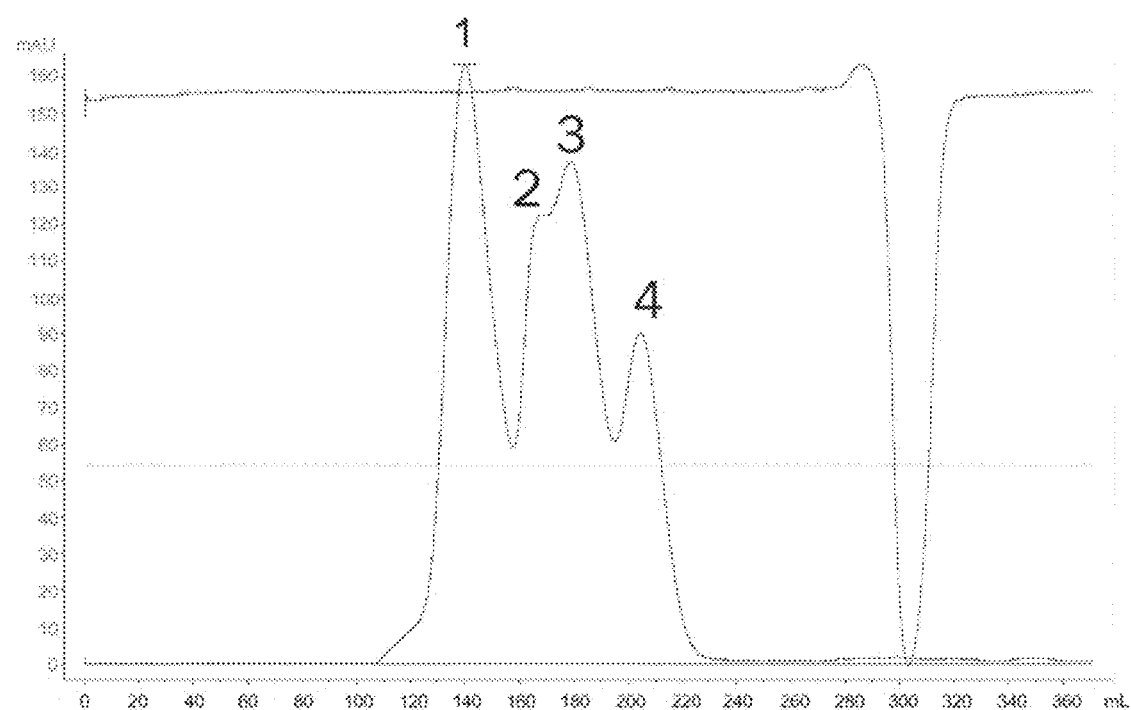

Figure 16:
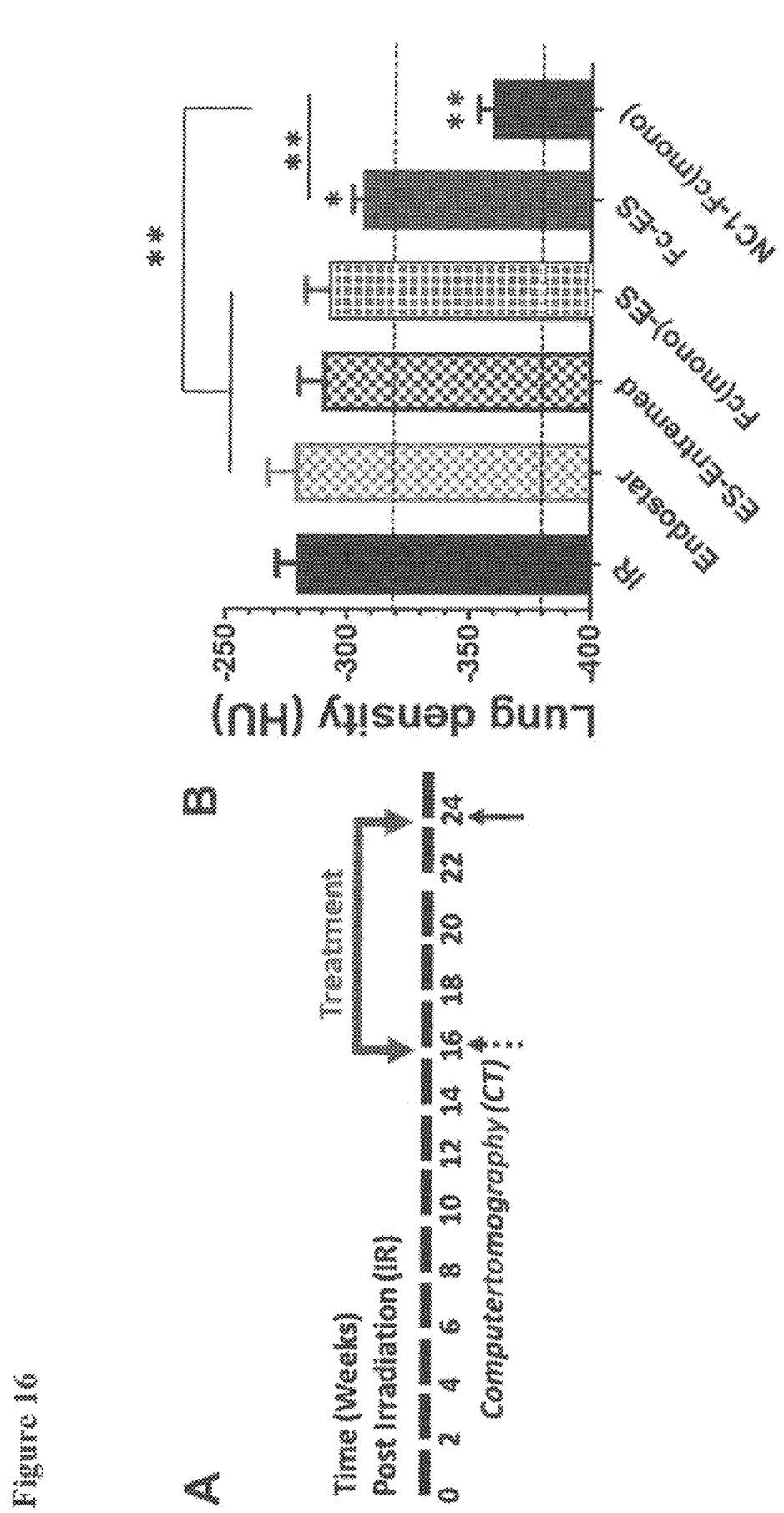

Figure 16
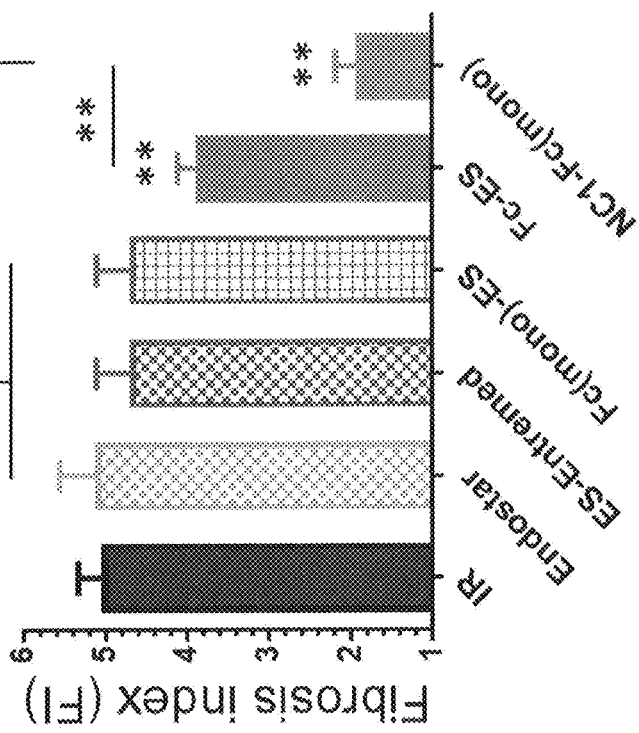
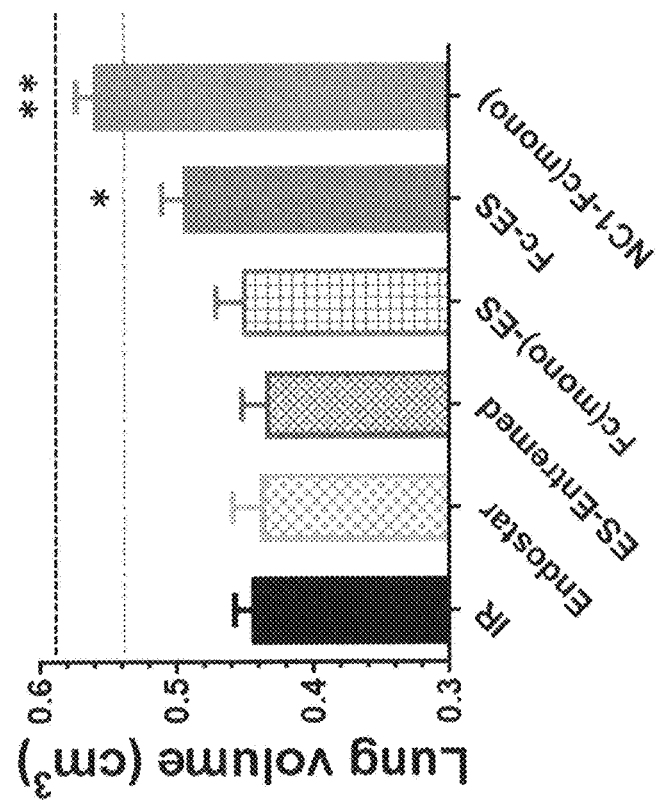

NC1-Fc(mono) forms a trimer

NON reduced Gel

1) Spectra Multicolor High Range Protein ladder
   (Thermo Scientific #26625) 10µl
2) Monomeric hFc-NC1 25µg
3) Monomeric hFc-NC1 crosslinked 25µg Figure 25
A
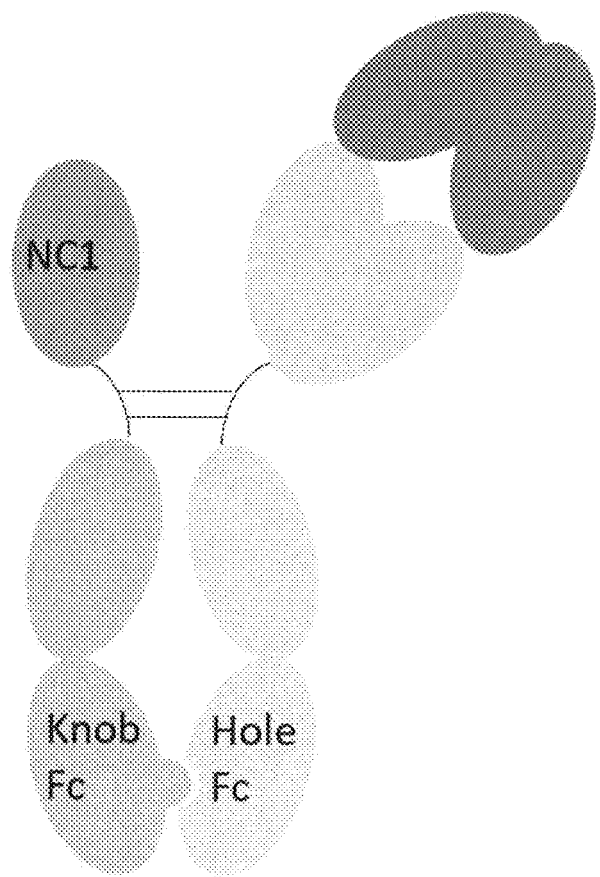
B
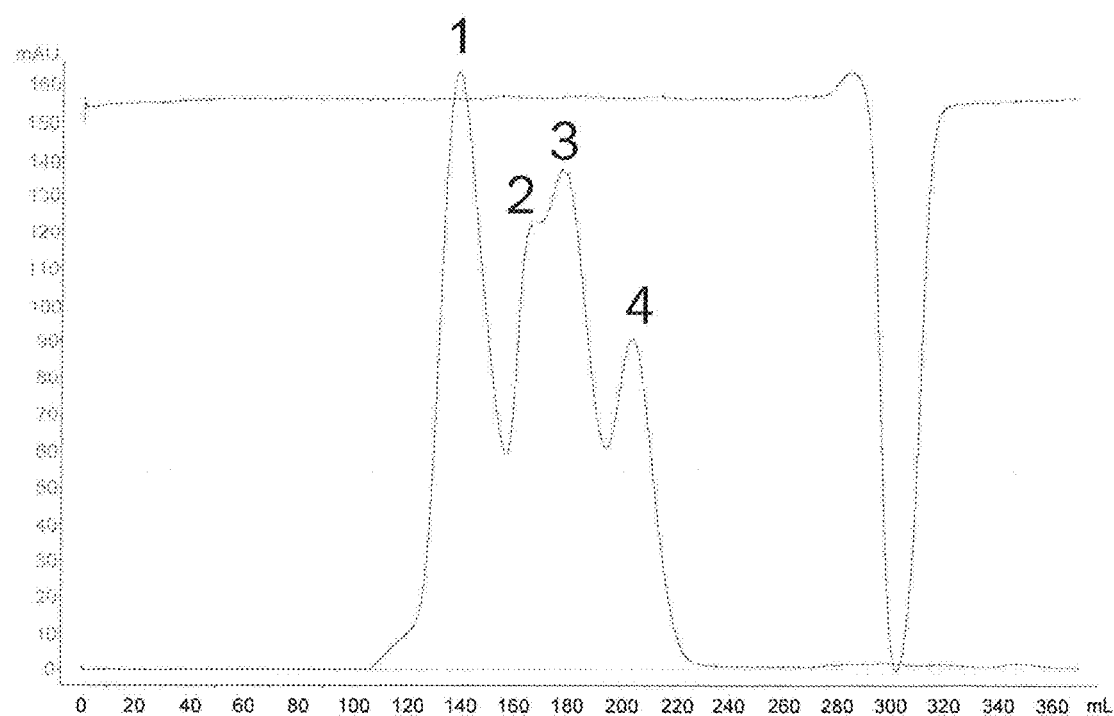

SEQUENCE LISTING

<160> NUMBER OF SEQ ID NOS: 42

<210> SEQ ID NO 1
<211> LENGTH: 1527
<212> TYPE: PRT
<213> ORGANISM: Mus musculus

<400> SEQUENCE: 1

Met Ala Pro Asp Pro Ser Arg Arg Leu Cys Leu Leu Leu Leu Leu
1               5                   10                  15

Leu Ser Cys Arg Leu Val Pro Ala Ser Ala Asp Gly Asn Ser Leu Ser
            20                  25                  30

Pro Leu Asn Pro Leu Val Trp Leu Trp Pro Pro Lys Thr Ser Asp Ser
        35                  40                  45

Leu Glu Gly Pro Val Ser Lys Pro Gln Asn Ser Ser Pro Val Gln Ser
    50                  55                  60

Thr Glu Asn Pro Thr Thr His Val Val Pro Gln Asp Gly Leu Thr Glu
65                  70                  75                  80

Gln Gln Thr Thr Pro Ala Ser Ser Glu Leu Pro Pro Glu Glu Glu Glu
                85                  90                  95

-continued

Glu Glu Asp Gln Lys Ala Gly Gln Gly Ser Pro Ala Thr Pro Ala
            100                 105                 110

Val Pro Ile Pro Leu Val Ala Pro Ala Ser Pro Asp Met Lys Glu
        115                 120                 125

Glu Asn Val Ala Gly Val Gly Ala Lys Ile Leu Asn Val Ala Gln Gly
    130                 135                 140

Ile Arg Ser Phe Val Gln Leu Trp Asp Glu Asp Ser Thr Ile Gly His
145                 150                 155                 160

Ser Ala Gly Thr Glu Val Pro Asp Ser Ser Ile Pro Thr Val Leu Pro
                165                 170                 175

Ser Pro Ala Glu Leu Ser Ser Ala Pro Gln Gly Ser Lys Thr Thr Leu
            180                 185                 190

Trp Leu Ser Ser Ala Ile Pro Ser Ser Pro Asp Ala Gln Thr Thr Glu
        195                 200                 205

Ala Gly Thr Leu Ala Val Pro Thr Gln Leu Pro Pro Phe Gln Ser Asn
    210                 215                 220

Leu Gln Ala Pro Leu Gly Arg Pro Ser Ala Pro Pro Asp Phe Pro Glu
225                 230                 235                 240

Asn Val Ala Glu Glu Val Gly Leu Leu Gln Leu Leu Gly Asp Pro Leu
                245                 250                 255

Pro Glu Lys Ile Ser Gln Ile Asp Asp Pro His Val Gly Pro Ala Tyr
            260                 265                 270

Ile Phe Gly Pro Asp Ser Asn Ser Gly Gln Val Ala Gln Tyr His Phe
        275                 280                 285

Pro Lys Leu Phe Phe Arg Asp Phe Ser Leu Leu Phe His Val Arg Pro
    290                 295                 300

Ala Thr Glu Ala Ala Gly Val Leu Phe Ala Ile Thr Asp Ala Ala Gln
305                 310                 315                 320

Val Val Val Ser Leu Gly Val Lys Leu Ser Glu Val Arg Asp Gly Gln
                325                 330                 335

Gln Asn Ile Ser Leu Leu Tyr Thr Glu Pro Gly Ala Ser Gln Thr Gln
            340                 345                 350

Thr Gly Ala Ser Phe Arg Leu Pro Ala Phe Val Gly Gln Trp Thr His
        355                 360                 365

Phe Ala Leu Ser Val Asp Gly Gly Ser Val Ala Leu Tyr Val Asp Cys
    370                 375                 380

Glu Glu Phe Gln Arg Val Pro Phe Ala Arg Ala Ser Gln Gly Leu Glu
385                 390                 395                 400

Leu Glu Arg Gly Ala Gly Leu Phe Val Gly Gln Ala Gly Thr Ala Asp
                405                 410                 415

Pro Asp Lys Phe Gln Gly Met Ile Ser Glu Leu Lys Val Arg Lys Thr
            420                 425                 430

Pro Arg Val Ser Pro Val His Cys Leu Asp Glu Glu Asp Asp Glu
        435                 440                 445

Asp Arg Ala Ser Gly Asp Phe Gly Ser Gly Phe Glu Glu Ser Ser Lys
    450                 455                 460

Ser His Lys Glu Asp Thr Ser Leu Leu Pro Gly Leu Pro Gln Pro Pro
465                 470                 475                 480

Pro Val Thr Ser Pro Pro Leu Ala Gly Gly Ser Thr Thr Glu Asp Pro
                485                 490                 495

Arg Thr Glu Glu Thr Glu Glu Asp Ala Ala Val Asp Ser Ile Gly Ala
            500                 505                 510

Glu Thr Leu Pro Gly Thr Gly Ser Ser Gly Ala Trp Asp Glu Ala Ile

-continued

```
            515                 520                 525
Gln Asn Pro Gly Arg Gly Leu Ile Lys Gly Met Lys Gly Gln Lys
        530                 535                 540
Gly Glu Pro Gly Ala Gln Gly Pro Pro Gly Ala Gly Pro Gln Gly
545                 550                 555                 560
Pro Ala Gly Pro Val Gln Ser Pro Asn Ser Gln Pro Val Pro Gly
                565                 570                 575
Ala Gln Gly Pro Pro Gly Pro Gln Gly Pro Pro Gly Lys Asp Gly Thr
            580                 585                 590
Pro Gly Arg Asp Gly Glu Pro Gly Asp Pro Gly Glu Asp Gly Arg Pro
            595                 600                 605
Gly Asp Thr Gly Pro Gln Gly Phe Pro Gly Thr Pro Gly Asp Val Gly
            610                 615                 620
Pro Lys Gly Glu Lys Gly Asp Pro Gly Ile Gly Pro Arg Gly Pro Pro
625                 630                 635                 640
Gly Pro Pro Gly Pro Pro Gly Pro Ser Phe Arg Gln Asp Lys Leu Thr
                645                 650                 655
Phe Ile Asp Met Glu Gly Ser Gly Phe Ser Gly Asp Ile Glu Ser Leu
                660                 665                 670
Arg Gly Pro Arg Gly Phe Pro Gly Pro Gly Pro Pro Gly Val Pro
            675                 680                 685
Gly Leu Pro Gly Glu Pro Gly Arg Phe Gly Ile Asn Gly Ser Tyr Ala
            690                 695                 700
Pro Gly Pro Ala Gly Leu Pro Gly Val Pro Gly Lys Glu Gly Pro Pro
705                 710                 715                 720
Gly Phe Pro Gly Pro Pro Gly Pro Pro Gly Lys Glu Gly
                725                 730                 735
Pro Pro Gly Val Ala Gly Gln Lys Gly Ser Val Gly Asp Val Gly Ile
                740                 745                 750
Pro Gly Pro Lys Gly Ser Lys Gly Asp Leu Gly Pro Ile Gly Met Pro
                755                 760                 765
Gly Lys Ser Gly Leu Ala Gly Ser Pro Gly Pro Val Gly Pro Pro Gly
            770                 775                 780
Pro Pro Gly Pro Pro Gly Pro Pro Gly Phe Ala Ala Gly Phe
785                 790                 795                 800
Asp Asp Met Glu Gly Ser Gly Ile Pro Leu Trp Thr Thr Ala Arg Ser
                805                 810                 815
Ser Asp Gly Leu Gln Gly Pro Pro Gly Ser Pro Gly Leu Lys Gly Asp
            820                 825                 830
Pro Gly Val Ala Gly Leu Pro Gly Ala Lys Gly Glu Val Gly Ala Asp
            835                 840                 845
Gly Ala Gln Gly Ile Pro Gly Pro Pro Gly Arg Gly Ala Ala Gly
            850                 855                 860
Ser Pro Gly Pro Lys Gly Glu Lys Gly Met Pro Gly Glu Lys Gly Asn
865                 870                 875                 880
Pro Gly Lys Asp Gly Val Gly Arg Pro Gly Leu Pro Gly Pro Pro Gly
                885                 890                 895
Pro Pro Gly Pro Val Ile Tyr Val Ser Ser Glu Asp Lys Ala Ile Val
                900                 905                 910
Ser Thr Pro Gly Pro Glu Gly Lys Pro Gly Tyr Ala Gly Phe Pro Gly
            915                 920                 925
Pro Ala Gly Pro Lys Gly Asp Leu Gly Ser Lys Gly Glu Gln Gly Leu
            930                 935                 940
```

-continued

```
Pro Gly Pro Lys Gly Glu Lys Gly Glu Pro Gly Thr Ile Phe Ser Pro
945                 950                 955                 960

Asp Gly Arg Ala Leu Gly His Pro Gln Lys Gly Ala Lys Gly Glu Pro
                965                 970                 975

Gly Phe Arg Gly Pro Pro Gly Tyr Gly Arg Pro Gly His Lys Gly
            980                 985                 990

Glu Ile Gly Phe Pro Gly Arg Pro Gly Arg Pro Gly Thr Asn Gly Leu
            995                 1000                1005

Lys Gly Glu Lys Gly Glu Pro Gly Asp Ala Ser Leu Gly Phe Ser Met
    1010                1015                1020

Arg Gly Leu Pro Gly Pro Pro Gly Pro Pro Gly Pro Pro Gly Pro Pro
1025                1030                1035                1040

Gly Met Pro Ile Tyr Asp Ser Asn Ala Phe Val Glu Ser Gly Arg Pro
                1045                1050                1055

Gly Leu Pro Gly Gln Gln Gly Val Gln Gly Pro Ser Gly Pro Lys Gly
                1060                1065                1070

Asp Lys Gly Glu Val Gly Pro Pro Gly Pro Pro Gly Gln Phe Pro Ile
            1075                1080                1085

Asp Leu Phe His Leu Glu Ala Glu Met Lys Gly Asp Lys Gly Asp Arg
    1090                1095                1100

Gly Asp Ala Gly Gln Lys Gly Glu Arg Gly Glu Pro Gly Ala Pro Gly
1105                1110                1115                1120

Gly Gly Phe Phe Ser Ser Val Pro Gly Pro Pro Gly Pro Pro Gly
                1125                1130                1135

Tyr Pro Gly Ile Pro Gly Pro Lys Gly Glu Ser Ile Arg Gly Pro Pro
            1140                1145                1150

Gly Pro Pro Gly Pro Gln Gly Pro Pro Gly Ile Gly Tyr Glu Gly Arg
    1155                1160                1165

Gln Gly Pro Pro Gly Pro Pro Gly Pro Pro Gly Pro Pro Ser Phe Pro
    1170                1175                1180

Gly Pro His Arg Gln Thr Val Ser Val Pro Gly Pro Pro Gly Pro Pro
1185                1190                1195                1200

Gly Pro Pro Gly Pro Pro Gly Ala Met Gly Ala Ser Ala Gly Gln Val
            1205                1210                1215

Arg Ile Trp Ala Thr Tyr Gln Thr Met Leu Asp Lys Ile Arg Glu Val
            1220                1225                1230

Pro Glu Gly Trp Leu Ile Phe Val Ala Glu Arg Glu Glu Leu Tyr Val
            1235                1240                1245

Arg Val Arg Asn Gly Phe Arg Lys Val Leu Leu Glu Ala Arg Thr Ala
            1250                1255                1260

Leu Pro Arg Gly Thr Gly Asn Glu Val Ala Ala Leu Gln Pro Pro Leu
1265                1270                1275                1280

Val Gln Leu His Glu Gly Ser Pro Tyr Thr Arg Arg Glu Tyr Ser Tyr
            1285                1290                1295

Ser Thr Ala Arg Pro Trp Arg Ala Asp Asp Ile Leu Ala Asn Pro Pro
    1300                1305                1310

Arg Leu Pro Asp Arg Gln Pro Tyr Pro Gly Val Pro His His His Ser
    1315                1320                1325

Ser Tyr Val His Leu Pro Pro Ala Arg Pro Thr Leu Ser Leu Ala His
    1330                1335                1340

Thr His Gln Asp Phe Gln Pro Val Leu His Leu Val Ala Leu Asn Thr
1345                1350                1355                1360
```

```
Pro Leu Ser Gly Gly Met Arg Gly Ile Arg Gly Ala Asp Phe Gln Cys
            1365                1370                1375

Phe Gln Gln Ala Arg Ala Val Gly Leu Ser Gly Thr Phe Arg Ala Phe
        1380                1385                1390

Leu Ser Ser Arg Leu Gln Asp Leu Tyr Ser Ile Val Arg Arg Ala Asp
        1395                1400                1405

Arg Gly Ser Val Pro Ile Val Asn Leu Lys Asp Glu Val Leu Ser Pro
        1410                1415                1420

Ser Trp Asp Ser Leu Phe Ser Gly Ser Gln Gln Leu Gln Pro Gly
1425                1430                1435                1440

Ala Arg Ile Phe Ser Phe Asp Gly Arg Asp Val Leu Arg His Pro Ala
            1445                1450                1455

Trp Pro Gln Lys Ser Val Trp His Gly Ser Asp Pro Ser Gly Arg Arg
            1460                1465                1470

Leu Met Glu Ser Tyr Cys Glu Thr Trp Arg Thr Glu Thr Thr Gly Ala
        1475                1480                1485

Thr Gly Gln Ala Ser Ser Leu Leu Ser Gly Arg Leu Leu Glu Gln Lys
            1490                1495                1500

Ala Ala Ser Cys His Asn Ser Tyr Ile Val Leu Cys Ile Glu Asn Ser
1505                1510                1515                1520

Phe Met Thr Ser Phe Ser Lys
                1525

<210> SEQ ID NO 2
<211> LENGTH: 1516
<212> TYPE: PRT
<213> ORGANISM: Homo sapiens

<400> SEQUENCE: 2

Met Ala Pro Tyr Pro Cys Gly Cys His Ile Leu Leu Leu Leu Phe Cys
1               5                   10                  15

Cys Leu Ala Ala Ala Arg Ala Asn Leu Leu Asn Leu Asn Trp Leu Trp
            20                  25                  30

Phe Asn Asn Glu Asp Thr Ser His Ala Ala Thr Thr Ile Pro Glu Pro
        35                  40                  45

Gln Gly Pro Leu Pro Val Gln Pro Thr Ala Asp Thr Thr His Val
    50                  55                  60

Thr Pro Arg Asn Gly Ser Thr Glu Pro Ala Thr Ala Pro Gly Ser Pro
65              70                  75                  80

Glu Pro Pro Ser Glu Leu Leu Glu Asp Gly Gln Asp Thr Pro Thr Ser
                85                  90                  95

Ala Glu Ser Pro Asp Ala Pro Glu Glu Asn Ile Ala Gly Val Gly Ala
            100                 105                 110

Glu Ile Leu Asn Val Ala Lys Gly Ile Arg Ser Phe Val Gln Leu Trp
        115                 120                 125

Asn Asp Thr Val Pro Thr Glu Ser Leu Ala Arg Ala Glu Thr Leu Val
    130                 135                 140

Leu Glu Thr Pro Val Gly Pro Leu Ala Leu Ala Gly Pro Ser Ser Thr
145             150                 155                 160

Pro Gln Glu Asn Gly Thr Thr Leu Trp Pro Ser Arg Gly Ile Pro Ser
                165                 170                 175

Ser Pro Gly Ala His Thr Thr Glu Ala Gly Thr Leu Pro Ala Pro Thr
            180                 185                 190

Pro Ser Pro Pro Ser Leu Gly Arg Pro Trp Ala Pro Leu Thr Gly Pro
        195                 200                 205
```

```
Ser Val Pro Pro Pro Ser Ser Glu Arg Ile Ser Glu Glu Val Gly Leu
    210                 215                 220

Leu Gln Leu Leu Gly Asp Pro Pro Gln Gln Val Thr Gln Thr Asp
225                 230                 235                 240

Asp Pro Asp Val Gly Leu Ala Tyr Val Phe Gly Pro Asp Ala Asn Ser
                245                 250                 255

Gly Gln Val Ala Arg Tyr His Phe Pro Ser Leu Phe Phe Arg Asp Phe
                260                 265                 270

Ser Leu Leu Phe His Ile Arg Pro Ala Thr Glu Gly Pro Gly Val Leu
    275                 280                 285

Phe Ala Ile Thr Asp Ser Ala Gln Ala Met Val Leu Leu Gly Val Lys
290                 295                 300

Leu Ser Gly Val Gln Asp Gly His Gln Asp Ile Ser Leu Leu Tyr Thr
305                 310                 315                 320

Glu Pro Gly Ala Gly Gln Thr His Thr Ala Ala Ser Phe Arg Leu Pro
                325                 330                 335

Ala Phe Val Gly Gln Trp Thr His Leu Ala Leu Ser Val Ala Gly Gly
                340                 345                 350

Phe Val Ala Leu Tyr Val Asp Cys Glu Glu Phe Gln Arg Met Pro Leu
    355                 360                 365

Ala Arg Ser Ser Arg Gly Leu Glu Leu Glu Pro Gly Ala Gly Leu Phe
370                 375                 380

Val Ala Gln Ala Gly Gly Ala Asp Pro Asp Lys Phe Gln Gly Val Ile
385                 390                 395                 400

Ala Glu Leu Lys Val Arg Arg Asp Pro Gln Val Ser Pro Met His Cys
                405                 410                 415

Leu Asp Glu Glu Gly Asp Asp Ser Asp Gly Ala Ser Gly Asp Ser Gly
                420                 425                 430

Ser Gly Leu Gly Asp Ala Arg Glu Leu Leu Arg Glu Thr Gly Ala
    435                 440                 445

Ala Leu Lys Pro Arg Leu Pro Ala Pro Pro Val Thr Thr Pro Pro
450                 455                 460

Leu Ala Gly Gly Ser Ser Thr Glu Asp Ser Arg Ser Glu Glu Val Glu
465                 470                 475                 480

Glu Gln Thr Thr Val Ala Ser Leu Gly Ala Gln Thr Leu Pro Gly Ser
                485                 490                 495

Asp Ser Val Ser Thr Trp Asp Gly Ser Val Arg Thr Pro Gly Gly Arg
                500                 505                 510

Val Lys Glu Gly Gly Leu Lys Gly Gln Lys Gly Glu Pro Gly Val Pro
                515                 520                 525

Gly Pro Pro Gly Arg Ala Gly Pro Gly Ser Pro Cys Leu Pro Gly
    530                 535                 540

Pro Pro Gly Leu Pro Cys Pro Val Ser Pro Leu Gly Pro Ala Gly Pro
545                 550                 555                 560

Ala Leu Gln Thr Val Pro Gly Pro Gln Pro Gly Pro Gly Pro Pro Gly
                565                 570                 575

Arg Asp Gly Thr Pro Gly Arg Asp Gly Glu Pro Gly Asp Pro Gly Glu
                580                 585                 590

Asp Gly Lys Pro Gly Asp Thr Gly Pro Gln Gly Phe Pro Gly Thr Pro
    595                 600                 605

Gly Asp Val Gly Pro Lys Gly Asp Lys Gly Asp Pro Gly Val Gly Glu
610                 615                 620
```

-continued

```
Arg Gly Pro Pro Gly Pro Gln Gly Pro Pro Gly Pro Pro Gly Pro Ser
625                 630                 635                 640

Phe Arg His Asp Lys Leu Thr Phe Ile Asp Met Glu Gly Ser Gly Phe
                645                 650                 655

Gly Gly Asp Leu Glu Ala Leu Arg Gly Pro Arg Gly Phe Pro Gly Pro
                660                 665                 670

Pro Gly Pro Pro Gly Val Pro Gly Leu Pro Gly Glu Pro Gly Arg Phe
            675                 680                 685

Gly Val Asn Ser Ser Asp Val Pro Gly Pro Ala Gly Leu Pro Gly Val
        690                 695                 700

Pro Gly Arg Glu Gly Pro Pro Gly Phe Pro Gly Leu Pro Gly Pro Pro
705                 710                 715                 720

Gly Pro Pro Gly Arg Glu Gly Pro Pro Gly Arg Thr Gly Gln Lys Gly
                725                 730                 735

Ser Leu Gly Glu Ala Gly Ala Pro Gly His Lys Gly Ser Lys Gly Ala
                740                 745                 750

Pro Gly Pro Ala Gly Ala Arg Gly Glu Ser Gly Leu Ala Gly Ala Pro
            755                 760                 765

Gly Pro Ala Gly Pro Pro Gly Pro Pro Gly Pro Pro Gly Pro Pro Gly
        770                 775                 780

Pro Gly Leu Pro Ala Gly Phe Asp Asp Met Glu Gly Ser Gly Gly Pro
785                 790                 795                 800

Phe Trp Ser Thr Ala Arg Ser Ala Asp Gly Pro Gln Gly Pro Pro Gly
                805                 810                 815

Leu Pro Gly Leu Lys Gly Asp Pro Gly Val Pro Gly Leu Pro Gly Ala
            820                 825                 830

Lys Gly Glu Val Gly Ala Asp Gly Val Pro Gly Phe Pro Gly Leu Pro
        835                 840                 845

Gly Arg Glu Gly Ile Ala Gly Pro Gln Gly Pro Lys Gly Asp Arg Gly
        850                 855                 860

Ser Arg Gly Glu Lys Gly Asp Pro Gly Lys Asp Gly Val Gly Gln Pro
865                 870                 875                 880

Gly Leu Pro Gly Pro Pro Gly Pro Pro Gly Pro Val Val Tyr Val Ser
                885                 890                 895

Glu Gln Asp Gly Ser Val Leu Ser Val Pro Gly Pro Glu Gly Arg Pro
                900                 905                 910

Gly Phe Ala Gly Phe Pro Gly Pro Ala Gly Pro Lys Gly Asn Leu Gly
            915                 920                 925

Ser Lys Gly Glu Arg Gly Ser Pro Gly Pro Lys Gly Glu Lys Gly Glu
        930                 935                 940

Pro Gly Ser Ile Phe Ser Pro Asp Gly Gly Ala Leu Gly Pro Ala Gln
945                 950                 955                 960

Lys Gly Ala Lys Gly Glu Pro Gly Phe Arg Gly Pro Pro Gly Pro Tyr
                965                 970                 975

Gly Arg Pro Gly Tyr Lys Gly Glu Ile Gly Phe Pro Gly Arg Pro Gly
                980                 985                 990

Arg Pro Gly Met Asn Gly Leu Lys Gly Glu Lys Gly Glu Pro Gly Asp
            995                 1000                1005

Ala Ser Leu Gly Phe Gly Met Arg Gly Met Pro Gly Pro Pro Gly Pro
            1010                1015                1020

Pro Gly Pro Pro Gly Pro Pro Gly Thr Pro Val Tyr Asp Ser Asn Val
1025                1030                1035                1040

Phe Ala Glu Ser Ser Arg Pro Gly Pro Pro Gly Leu Pro Gly Asn Gln
```

-continued

```
                    1045                1050                1055
Gly Pro Pro Gly Pro Lys Gly Ala Lys Gly Glu Val Gly Pro Pro Gly
                1060                1065                1070
Pro Pro Gly Gln Phe Pro Phe Asp Phe Leu Gln Leu Glu Ala Glu Met
            1075                1080                1085
Lys Gly Glu Lys Gly Asp Arg Gly Asp Ala Gly Gln Lys Gly Glu Arg
        1090                1095                1100
Gly Glu Pro Gly Gly Gly Phe Phe Gly Ser Ser Leu Pro Gly Pro
1105                1110                1115                1120
Pro Gly Pro Pro Gly Pro Arg Gly Tyr Pro Gly Ile Pro Gly Pro Lys
                1125                1130                1135
Gly Glu Ser Ile Arg Gly Gln Pro Gly Pro Pro Gly Pro Gln Gly Pro
                1140                1145                1150
Pro Gly Ile Gly Tyr Glu Gly Arg Gln Gly Pro Gly Pro Pro Gly
                1155                1160                1165
Pro Pro Gly Pro Pro Ser Phe Pro Gly Pro His Arg Gln Thr Ile Ser
            1170                1175                1180
Val Pro Gly Pro Pro Gly Pro Pro Gly Pro Pro Gly Pro Pro Gly Thr
1185                1190                1195                1200
Met Gly Ala Ser Ser Gly Val Arg Leu Trp Ala Thr Arg Gln Ala Met
                1205                1210                1215
Leu Gly Gln Val His Glu Val Pro Glu Gly Trp Leu Ile Phe Val Ala
                1220                1225                1230
Glu Gln Glu Glu Leu Tyr Val Arg Val Gln Asn Gly Phe Arg Lys Val
            1235                1240                1245
Gln Leu Glu Ala Arg Thr Pro Leu Pro Arg Gly Thr Asp Asn Glu Val
        1250                1255                1260
Ala Ala Leu Gln Pro Pro Val Val Gln Leu His Asp Ser Asn Pro Tyr
1265                1270                1275                1280
Pro Arg Arg Glu His Pro His Pro Thr Ala Arg Pro Trp Arg Ala Asp
                1285                1290                1295
Asp Ile Leu Ala Ser Pro Pro Arg Leu Pro Glu Pro Gln Pro Tyr Pro
            1300                1305                1310
Gly Ala Pro His His Ser Ser Tyr Val His Leu Arg Pro Ala Arg Pro
        1315                1320                1325
Thr Ser Pro Pro Ala His Ser His Arg Asp Phe Gln Pro Val Leu His
        1330                1335                1340
Leu Val Ala Leu Asn Ser Pro Leu Ser Gly Gly Met Arg Gly Ile Arg
1345                1350                1355                1360
Gly Ala Asp Phe Gln Cys Phe Gln Gln Ala Arg Ala Val Gly Leu Ala
                1365                1370                1375
Gly Thr Phe Arg Ala Phe Leu Ser Ser Arg Leu Gln Asp Leu Tyr Ser
            1380                1385                1390
Ile Val Arg Arg Ala Asp Arg Ala Ala Val Pro Ile Val Asn Leu Lys
        1395                1400                1405
Asp Glu Leu Leu Phe Pro Ser Trp Glu Ala Leu Phe Ser Gly Ser Glu
        1410                1415                1420
Gly Pro Leu Lys Pro Gly Ala Arg Ile Phe Ser Phe Asp Gly Lys Asp
1425                1430                1435                1440
Val Leu Arg His Pro Thr Trp Pro Gln Lys Ser Val Trp His Gly Ser
                1445                1450                1455
Asp Pro Asn Gly Arg Arg Leu Thr Glu Ser Tyr Cys Glu Thr Trp Arg
                1460                1465                1470
```

```
Thr Glu Ala Pro Ser Ala Thr Gly Gln Ala Ser Ser Leu Leu Gly Gly
        1475                1480                1485

Arg Leu Leu Gly Gln Ser Ala Ala Ser Cys His His Ala Tyr Ile Val
        1490                1495                1500

Leu Cys Ile Glu Asn Ser Phe Met Thr Ala Ser Lys
1505                1510                1515

<210> SEQ ID NO 3
<211> LENGTH: 315
<212> TYPE: PRT
<213> ORGANISM: Mus musculus

<400> SEQUENCE: 3

Ala Gly Gln Val Arg Ile Trp Ala Thr Tyr Gln Thr Met Leu Asp Lys
1               5                   10                  15

Ile Arg Glu Val Pro Glu Gly Trp Leu Ile Phe Val Ala Glu Arg Glu
            20                  25                  30

Glu Leu Tyr Val Arg Val Arg Asn Gly Phe Arg Lys Val Leu Leu Glu
        35                  40                  45

Ala Arg Thr Ala Leu Pro Arg Gly Thr Gly Asn Glu Val Ala Ala Leu
    50                  55                  60

Gln Pro Pro Leu Val Gln Leu His Glu Gly Ser Pro Tyr Thr Arg Arg
65                  70                  75                  80

Glu Tyr Ser Tyr Ser Thr Ala Arg Pro Trp Arg Ala Asp Asp Ile Leu
                85                  90                  95

Ala Asn Pro Pro Arg Leu Pro Asp Arg Gln Pro Tyr Pro Gly Val Pro
            100                 105                 110

His His His Ser Ser Tyr Val His Leu Pro Pro Ala Arg Pro Thr Leu
        115                 120                 125

Ser Leu Ala His Thr His Gln Asp Phe Gln Pro Val Leu His Leu Val
    130                 135                 140

Ala Leu Asn Thr Pro Leu Ser Gly Gly Met Arg Gly Ile Arg Gly Ala
145                 150                 155                 160

Asp Phe Gln Cys Phe Gln Gln Ala Arg Ala Val Gly Leu Ser Gly Thr
                165                 170                 175

Phe Arg Ala Phe Leu Ser Ser Arg Leu Gln Asp Leu Tyr Ser Ile Val
            180                 185                 190

Arg Arg Ala Asp Arg Gly Ser Val Pro Ile Val Asn Leu Lys Asp Glu
        195                 200                 205

Val Leu Ser Pro Ser Trp Asp Ser Leu Phe Ser Gly Ser Gln Gly Gln
    210                 215                 220

Leu Gln Pro Gly Ala Arg Ile Phe Ser Phe Asp Gly Arg Asp Val Leu
225                 230                 235                 240

Arg His Pro Ala Trp Pro Gln Lys Ser Val Trp His Gly Ser Asp Pro
                245                 250                 255

Ser Gly Arg Arg Leu Met Glu Ser Tyr Cys Glu Thr Trp Arg Thr Glu
            260                 265                 270

Thr Thr Gly Ala Thr Gly Gln Ala Ser Ser Leu Leu Ser Gly Arg Leu
        275                 280                 285

Leu Glu Gln Lys Ala Ala Ser Cys His Asn Ser Tyr Ile Val Leu Cys
    290                 295                 300

Ile Glu Asn Ser Phe Met Thr Ser Phe Ser Lys
305                 310                 315
```

<210> SEQ ID NO 4
<211> LENGTH: 312
<212> TYPE: PRT
<213> ORGANISM: Homo sapiens

<400> SEQUENCE: 4

Ser Gly Val Arg Leu Trp Ala Thr Arg Gln Ala Met Leu Gly Gln Val
1               5                   10                  15

His Glu Val Pro Glu Gly Trp Leu Ile Phe Val Ala Glu Gln Glu Glu
            20                  25                  30

Leu Tyr Val Arg Val Gln Asn Gly Phe Arg Lys Val Gln Leu Glu Ala
        35                  40                  45

Arg Thr Pro Leu Pro Arg Gly Thr Asp Asn Glu Val Ala Ala Leu Gln
    50                  55                  60

Pro Pro Val Val Gln Leu His Asp Ser Asn Pro Tyr Pro Arg Arg Glu
65                  70                  75                  80

His Pro His Pro Thr Ala Arg Pro Trp Arg Ala Asp Asp Ile Leu Ala
                85                  90                  95

Ser Pro Pro Arg Leu Pro Glu Pro Gln Pro Tyr Pro Gly Ala Pro His
            100                 105                 110

His Ser Ser Tyr Val His Leu Arg Pro Ala Arg Pro Thr Ser Pro Pro
        115                 120                 125

Ala His Ser His Arg Asp Phe Gln Pro Val Leu His Leu Val Ala Leu
    130                 135                 140

Asn Ser Pro Leu Ser Gly Gly Met Arg Gly Ile Arg Gly Ala Asp Phe
145                 150                 155                 160

Gln Cys Phe Gln Gln Ala Arg Ala Val Gly Leu Ala Gly Thr Phe Arg
                165                 170                 175

Ala Phe Leu Ser Ser Arg Leu Gln Asp Leu Tyr Ser Ile Val Arg Arg
            180                 185                 190

Ala Asp Arg Ala Ala Val Pro Ile Val Asn Leu Lys Asp Glu Leu Leu
        195                 200                 205

Phe Pro Ser Trp Glu Ala Leu Phe Ser Gly Ser Glu Gly Pro Leu Lys
    210                 215                 220

Pro Gly Ala Arg Ile Phe Ser Phe Asp Gly Lys Asp Val Leu Arg His
225                 230                 235                 240

Pro Thr Trp Pro Gln Lys Ser Val Trp His Gly Ser Asp Pro Asn Gly
                245                 250                 255

Arg Arg Leu Thr Glu Ser Tyr Cys Glu Thr Trp Arg Thr Glu Ala Pro
            260                 265                 270

Ser Ala Thr Gly Gln Ala Ser Ser Leu Leu Gly Gly Arg Leu Leu Gly
        275                 280                 285

Gln Ser Ala Ala Ser Cys His His Ala Tyr Ile Val Leu Cys Ile Glu
    290                 295                 300

Asn Ser Phe Met Thr Ala Ser Lys
305                 310

<210> SEQ ID NO 5
<211> LENGTH: 233
<212> TYPE: PRT
<213> ORGANISM: Mus musculus

<400> SEQUENCE: 5

Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys

```
                20                  25                  30
Ile Lys Asp Val Leu Met Ile Ser Leu Ser Pro Ile Val Thr Cys Val
            35                  40                  45

Val Val Asp Val Ser Glu Asp Pro Asp Val Gln Ile Ser Trp Phe
 50                  55                  60

Val Asn Asn Val Glu Val His Thr Ala Gln Thr Gln Thr His Arg Glu
 65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
                100                 105                 110

Asp Leu Pro Ala Pro Ile Glu Arg Thr Ile Ser Lys Pro Lys Gly Ser
            115                 120                 125

Val Arg Ala Pro Gln Val Tyr Val Leu Pro Pro Glu Glu Glu Met
130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
            195                 200                 205

Tyr Ser Cys Ser Val Val His Glu Gly Leu His Asn His His Thr Thr
    210                 215                 220

Lys Ser Phe Ser Arg Thr Pro Gly Lys
225                 230

<210> SEQ ID NO 6
<211> LENGTH: 232
<212> TYPE: PRT
<213> ORGANISM: Homo sapiens

<400> SEQUENCE: 6

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 7
<211> LENGTH: 28
<212> TYPE: PRT
<213> ORGANISM: Mus musculus

<400> SEQUENCE: 7

His Thr His Gln Asp Phe Gln Pro Val Leu His Leu Val Leu Tyr Ala
1               5                   10                  15

Val Thr Gly Arg Gly Asp Ser Pro Ala Ser Ser Lys
            20                  25

<210> SEQ ID NO 8
<211> LENGTH: 15
<212> TYPE: PRT
<213> ORGANISM: Mus musculus

<400> SEQUENCE: 8

Leu Tyr Ala Val Thr Gly Arg Gly Asp Ser Pro Ala Ser Ser Lys
1               5                   10                  15

<210> SEQ ID NO 9
<211> LENGTH: 26
<212> TYPE: PRT
<213> ORGANISM: Mus musculus

<400> SEQUENCE: 9

His Thr His Gln Asp Phe Gln Pro Val Leu His Leu Val Ala Leu Asn
1               5                   10                  15

Thr Pro Leu Ser Gly Gly Met Arg Gly Ile
            20                  25

<210> SEQ ID NO 10
<211> LENGTH: 25
<212> TYPE: PRT
<213> ORGANISM: Homo sapiens

<400> SEQUENCE: 10

His Ser His Arg Asp Phe Gln Pro Val Leu His Leu Val Ala Leu Asn
1               5                   10                  15

Ser Pro Leu Ser Gly Gly Met Arg Gly
            20                  25

<210> SEQ ID NO 11
<211> LENGTH: 15
<212> TYPE: PRT
<213> ORGANISM: Mus musculus

<400> SEQUENCE: 11

Leu Tyr Ala Val Thr Gly Arg Gly Asp Ser Pro Ala Ser Ser Lys
1               5                   10                  15
```

<210> SEQ ID NO 12
<211> LENGTH: 15
<212> TYPE: PRT
<213> ORGANISM: Homo sapiens

<400> SEQUENCE: 12

Val Tyr Ala Val Thr Gly Arg Gly Asp Ser Pro Ala Ser Ser Lys
1               5                   10                  15

<210> SEQ ID NO 13
<211> LENGTH: 27
<212> TYPE: PRT
<213> ORGANISM: Homo sapiens

<400> SEQUENCE: 13

His Ser His Arg Asp Phe Gln Pro Val Leu His Leu Val Tyr Ala Val
1               5                   10                  15

Thr Gly Arg Gly Asp Ser Pro Ala Ser Ser Lys
            20                  25

<210> SEQ ID NO 14
<211> LENGTH: 27
<212> TYPE: PRT
<213> ORGANISM: Homo sapiens

<400> SEQUENCE: 14

Ala Ser Ala Arg Asp Phe Gln Pro Val Leu His Leu Val Tyr Ala Val
1               5                   10                  15

Thr Gly Arg Gly Asp Ser Pro Ala Ser Ser Lys
            20                  25

<210> SEQ ID NO 15
<211> LENGTH: 27
<212> TYPE: PRT
<213> ORGANISM: Homo sapiens

<400> SEQUENCE: 15

His Ser His Arg Asp Phe Cys Pro Val Leu His Leu Val Tyr Ala Val
1               5                   10                  15

Thr Gly Arg Gly Asp Ser Pro Ala Ser Ser Lys
            20                  25

<210> SEQ ID NO 16
<211> LENGTH: 27
<212> TYPE: PRT
<213> ORGANISM: Homo sapiens

<400> SEQUENCE: 16

His Ser His Arg Asp Phe Gln Pro Val Leu His Leu Val Tyr Ala Val
1               5                   10                  15

Thr Gly Arg Ala Asp Ser Pro Ala Ser Ser Lys
            20                  25

<210> SEQ ID NO 17
<211> LENGTH: 25
<212> TYPE: PRT
<213> ORGANISM: Mus musculus

<400> SEQUENCE: 17

Ile Lys Pro Gly Ala Asp Tyr Thr Ile Thr Leu Tyr Ala Val Thr Gly
1               5                   10                  15

Arg Gly Asp Ser Pro Ala Ser Ser Lys

<210> SEQ ID NO 18
<211> LENGTH: 184
<212> TYPE: PRT
<213> ORGANISM: Mus musculus

<400> SEQUENCE: 18

```
His Thr His Gln Asp Phe Gln Pro Val Leu His Leu Val Ala Leu Asn
1               5                   10                  15

Thr Pro Leu Ser Gly Gly Met Arg Gly Ile Arg Gly Ala Asp Phe Gln
            20                  25                  30

Cys Phe Gln Gln Ala Arg Ala Val Gly Leu Ser Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Gly Ser Val Pro Ile Val Asn Leu Lys Asp Glu Val Leu Ser
65                  70                  75                  80

Pro Ser Trp Asp Ser Leu Phe Ser Gly Ser Gln Gly Gln Leu Gln Pro
                85                  90                  95

Gly Ala Arg Ile Phe Ser Phe Asp Gly Arg Asp Val Leu Arg His Pro
            100                 105                 110

Ala Trp Pro Gln Lys Ser Val Trp His Gly Ser Asp Pro Ser Gly Arg
        115                 120                 125

Arg Leu Met Glu Ser Tyr Cys Glu Thr Trp Arg Thr Glu Thr Thr Gly
    130                 135                 140

Ala Thr Gly Gln Ala Ser Ser Leu Leu Ser Gly Arg Leu Leu Glu Gln
145                 150                 155                 160

Lys Ala Ala Ser Cys His Asn Ser Tyr Ile Val Leu Cys Ile Glu Asn
                165                 170                 175

Ser Phe Met Thr Ser Phe Ser Lys
            180
```

<210> SEQ ID NO 19
<211> LENGTH: 180
<212> TYPE: PRT
<213> ORGANISM: Homo sapiens

<400> SEQUENCE: 19

```
His Ser His Arg Asp Phe Gln Pro Val Leu His Leu Val Ala Leu Asn
1               5                   10                  15

Ala Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
```

```
                130                 135                 140
Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr
            180

<210> SEQ ID NO 20
<211> LENGTH: 27
<212> TYPE: PRT
<213> ORGANISM: Mus musculus

<400> SEQUENCE: 20

His Thr His Gln Asp Phe Gln Pro Val Leu His Leu Val Ala Leu Asn
1               5                   10                  15

Thr Pro Leu Ser Gly Gly Met Arg Gly Ile Arg
            20                  25

<210> SEQ ID NO 21
<211> LENGTH: 48
<212> TYPE: PRT
<213> ORGANISM: Homo sapiens

<400> SEQUENCE: 21

Ser Tyr Cys Glu Thr Trp Arg Thr Glu Ala Pro Ser Ala Thr Gly Gln
1               5                   10                  15

Ala Ser Ser Leu Leu Gly Gly Arg Leu Leu Gly Gln Ser Ala Ala Ser
            20                  25                  30

Cys His His Ala Tyr Ile Val Leu Cys Ile Glu Asn Ser Phe Met Thr
        35                  40                  45

<210> SEQ ID NO 22
<211> LENGTH: 27
<212> TYPE: PRT
<213> ORGANISM: Homo sapiens

<400> SEQUENCE: 22

His Ser His Arg Asp Phe Gln Pro Val Leu His Leu Val Ala Leu Asn
1               5                   10                  15

Ala Pro Leu Ser Gly Gly Met Arg Gly Ile Arg
            20                  25

<210> SEQ ID NO 23
<211> LENGTH: 5
<212> TYPE: PRT
<213> ORGANISM: Artificial Sequence
<220> FEATURE:
<223> OTHER INFORMATION: Enterokinase cleavage site

<400> SEQUENCE: 23

Asp Asp Asp Asp Lys
1               5

<210> SEQ ID NO 24
<211> LENGTH: 227
<212> TYPE: PRT
<213> ORGANISM: Homo sapiens

<400> SEQUENCE: 24

Asp Lys Thr His Thr Cys Pro Pro Cys Pro Ala Pro Glu Leu Leu Gly
1               5                   10                  15
```

-continued

```
Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 25
<211> LENGTH: 227
<212> TYPE: PRT
<213> ORGANISM: Homo sapiens

<400> SEQUENCE: 25

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
130                 135                 140

Leu Trp Cys Leu Val Lys Gly Phe Tyr Pro Ser Asp Ile Ala Val Glu
```

```
                145                 150                 155                 160
Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
                    180                 185                 190

Asp Lys Ser Arg Trp Gln Gln Gly Asn Val Phe Ser Cys Ser Val Met
                    195                 200                 205

His Glu Ala Leu His Asn His Tyr Thr Gln Lys Ser Leu Ser Leu Ser
                    210                 215                 220

Pro Gly Lys
225

<210> SEQ ID NO 26
<211> LENGTH: 227
<212> TYPE: PRT
<213> ORGANISM: Homo sapiens

<400> SEQUENCE: 26

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
            50                  55                  60

His Asn Ala Lys Thr Lys Pro Arg Glu Glu Gln Tyr Asn Ser Thr Tyr
65              70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Cys Thr Leu Pro Pro Ser Arg Asp Glu Leu Thr Lys Asn Gln Val Ser
                130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Val Ser Lys Leu Thr Val
                    180                 185                 190

Asp Lys Ser Arg Trp Gln Gln Gly Asn Val Phe Ser Cys Ser Val Met
                    195                 200                 205

His Glu Ala Leu His Asn His Tyr Thr Gln Lys Ser Leu Ser Leu Ser
                    210                 215                 220

Pro Gly Lys
225

<210> SEQ ID NO 27
<211> LENGTH: 554
<212> TYPE: PRT
<213> ORGANISM: Homo sapiens

<400> SEQUENCE: 27

Ser Gly Val Arg Leu Trp Ala Thr Arg Gln Ala Met Leu Gly Gln Val
```

-continued

```
1               5                   10                  15
His Glu Val Pro Glu Gly Trp Leu Ile Phe Val Ala Glu Gln Glu Glu
                20                  25                  30
Leu Tyr Val Arg Val Gln Asn Gly Phe Arg Lys Val Gln Leu Glu Ala
                35                  40                  45
Arg Thr Pro Leu Pro Arg Gly Thr Asp Asn Glu Val Ala Ala Leu Gln
50                  55                  60
Pro Pro Val Val Gln Leu His Asp Ser Asn Pro Tyr Pro Arg Arg Glu
65                  70                  75                  80
His Pro His Pro Thr Ala Arg Pro Trp Arg Ala Asp Asp Ile Leu Ala
                85                  90                  95
Ser Pro Pro Arg Leu Pro Glu Pro Gln Pro Tyr Gly Ala Pro His
                100                 105                 110
His Ser Ser Tyr Val His Leu Arg Pro Ala Arg Pro Thr Ser Pro Pro
                115                 120                 125
Ala His Ser His Arg Asp Phe Gln Pro Val Leu His Leu Val Ala Leu
    130                 135                 140
Asn Ser Pro Leu Ser Gly Gly Met Arg Gly Ile Arg Gly Ala Asp Phe
145                 150                 155                 160
Gln Cys Phe Gln Gln Ala Arg Ala Val Gly Leu Ala Gly Thr Phe Arg
                165                 170                 175
Ala Phe Leu Ser Ser Arg Leu Gln Asp Leu Tyr Ser Ile Val Arg Arg
                180                 185                 190
Ala Asp Arg Ala Ala Val Pro Ile Val Asn Leu Lys Asp Glu Leu Leu
                195                 200                 205
Phe Pro Ser Trp Glu Ala Leu Phe Ser Gly Ser Glu Gly Pro Leu Lys
210                 215                 220
Pro Gly Ala Arg Ile Phe Ser Phe Asp Gly Lys Asp Val Leu Arg His
225                 230                 235                 240
Pro Thr Trp Pro Gln Lys Ser Val Trp His Gly Ser Asp Pro Asn Gly
                245                 250                 255
Arg Arg Leu Thr Glu Ser Tyr Cys Glu Thr Trp Arg Thr Glu Ala Pro
                260                 265                 270
Ser Ala Thr Gly Gln Ala Ser Ser Leu Leu Gly Gly Arg Leu Leu Gly
                275                 280                 285
Gln Ser Ala Ala Ser Cys His His Ala Tyr Ile Val Leu Cys Ile Glu
                290                 295                 300
Asn Ser Phe Met Thr Ala Ser Lys Asp Asp Asp Asp Lys Gly Gly
305                 310                 315                 320
Gly Gly Ser Glu Pro Lys Ser Gln Asp Lys Thr His Thr Cys Pro Pro
                325                 330                 335
Cys Pro Ala Pro Glu Leu Leu Gly Gly Pro Ser Val Phe Leu Phe Pro
                340                 345                 350
Pro Lys Pro Lys Asp Thr Leu Met Ile Ser Arg Thr Pro Glu Val Thr
                355                 360                 365
Cys Val Val Val Asp Val Ser His Glu Asp Pro Glu Val Lys Phe Asn
                370                 375                 380
Trp Tyr Val Asp Gly Val Glu Val His Asn Ala Lys Thr Lys Pro Arg
385                 390                 395                 400
Glu Glu Gln Tyr Asn Ser Thr Tyr Arg Val Val Ser Val Leu Thr Val
                405                 410                 415
Leu His Gln Asp Trp Leu Asn Gly Lys Glu Tyr Lys Cys Lys Val Ser
                420                 425                 430
```

-continued

```
Asn Lys Ala Leu Pro Ala Pro Ile Glu Lys Thr Ile Ser Lys Ala Lys
        435                 440                 445

Gly Gln Pro Arg Glu Pro Gln Val Tyr Thr Leu Pro Pro Cys Arg Asp
    450                 455                 460

Glu Leu Thr Lys Asn Gln Val Ser Leu Trp Cys Leu Val Lys Gly Phe
465                 470                 475                 480

Tyr Pro Ser Asp Ile Ala Val Glu Trp Glu Ser Asn Gly Gln Pro Glu
                485                 490                 495

Asn Asn Tyr Lys Thr Thr Pro Pro Val Leu Asp Ser Asp Gly Ser Phe
                500                 505                 510

Phe Leu Tyr Ser Lys Leu Thr Val Asp Lys Ser Arg Trp Gln Gln Gly
        515                 520                 525

Asn Val Phe Ser Cys Ser Val Met His Glu Ala Leu His Asn His Tyr
    530                 535                 540

Thr Gln Lys Ser Leu Ser Leu Ser Pro Gly
545                 550

<210> SEQ ID NO 28
<211> LENGTH: 232
<212> TYPE: PRT
<213> ORGANISM: Homo sapiens

<400> SEQUENCE: 28

Glu Pro Lys Ser Gln Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Asp Glu Leu Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

```
<210> SEQ ID NO 29
<211> LENGTH: 552
<212> TYPE: PRT
<213> ORGANISM: Homo sapiens

<400> SEQUENCE: 29

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Pro Gly Ser Asp Asp Asp Asp Lys
225                 230                 235                 240

Ser Gly Val Arg Leu Trp Ala Thr Arg Gln Ala Met Leu Gly Gln Val
                245                 250                 255

His Glu Val Pro Glu Gly Trp Leu Ile Phe Val Ala Glu Gln Glu Glu
            260                 265                 270

Leu Tyr Val Arg Val Gln Asn Gly Phe Arg Lys Val Gln Leu Glu Ala
        275                 280                 285

Arg Thr Pro Leu Pro Arg Gly Thr Asp Asn Glu Val Ala Ala Leu Gln
    290                 295                 300

Pro Pro Val Val Gln Leu His Asp Ser Asn Pro Tyr Pro Arg Arg Glu
305                 310                 315                 320

His Pro His Pro Thr Ala Arg Pro Trp Arg Ala Asp Asp Ile Leu Ala
                325                 330                 335

Ser Pro Pro Arg Leu Pro Glu Pro Gln Pro Tyr Pro Gly Ala Pro His
            340                 345                 350

His Ser Ser Tyr Val His Leu Arg Pro Ala Arg Pro Thr Ser Pro Pro
        355                 360                 365

Ala His Ser His Arg Asp Phe Gln Pro Val Leu His Leu Val Ala Leu
    370                 375                 380
```

-continued

```
Asn Ser Pro Leu Ser Gly Gly Met Arg Gly Ile Arg Gly Ala Asp Phe
385                 390                 395                 400

Gln Cys Phe Gln Gln Ala Arg Ala Val Gly Leu Ala Gly Thr Phe Arg
            405                 410                 415

Ala Phe Leu Ser Ser Arg Leu Gln Asp Leu Tyr Ser Ile Val Arg Arg
        420                 425                 430

Ala Asp Arg Ala Ala Val Pro Ile Val Asn Leu Lys Asp Glu Leu Leu
    435                 440                 445

Phe Pro Ser Trp Glu Ala Leu Phe Ser Gly Ser Glu Gly Pro Leu Lys
450                 455                 460

Pro Gly Ala Arg Ile Phe Ser Phe Asp Gly Lys Asp Val Leu Arg His
465                 470                 475                 480

Pro Thr Trp Pro Gln Lys Ser Val Trp His Gly Ser Asp Pro Asn Gly
            485                 490                 495

Arg Arg Leu Thr Glu Ser Tyr Cys Glu Thr Trp Arg Thr Glu Ala Pro
        500                 505                 510

Ser Ala Thr Gly Gln Ala Ser Ser Leu Leu Gly Gly Arg Leu Leu Gly
    515                 520                 525

Gln Ser Ala Ala Ser Cys His His Ala Tyr Ile Val Leu Cys Ile Glu
530                 535                 540

Asn Ser Phe Met Thr Ala Ser Lys
545                 550

<210> SEQ ID NO 30
<211> LENGTH: 227
<212> TYPE: PRT
<213> ORGANISM: Homo sapiens

<400> SEQUENCE: 30

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
        100                 105                 110

Glu Lys Thr Ile Ser Lys Ala Lys Gly Gln Pro Arg Glu Pro Gln Val
    115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Val Ser Lys Leu Thr Val
        180                 185                 190

Asp Lys Ser Arg Trp Gln Gln Gly Asn Val Phe Ser Cys Ser Val Met
    195                 200                 205
```

His Glu Ala Leu His Asn His Tyr Thr Gln Lys Ser Leu Ser Leu Ser
    210                 215                 220

Pro Gly Lys
225

<210> SEQ ID NO 31
<211> LENGTH: 555
<212> TYPE: PRT
<213> ORGANISM: Artificial Sequence
<220> FEATURE:
<223> OTHER INFORMATION: Heterodimeric NC1-Fc, Molecule 1, Chain 1

<400> SEQUENCE: 31

Ser Gly Val Arg Leu Trp Ala Thr Arg Gln Ala Met Leu Gly Gln Val
1               5                   10                  15

His Glu Val Pro Glu Gly Trp Leu Ile Phe Val Ala Glu Gln Glu Glu
            20                  25                  30

Leu Tyr Val Arg Val Gln Asn Gly Phe Arg Lys Val Gln Leu Glu Ala
        35                  40                  45

Arg Thr Pro Leu Pro Arg Gly Thr Asp Asn Glu Val Ala Ala Leu Gln
    50                  55                  60

Pro Val Val Gln Leu His Asp Ser Asn Pro Tyr Pro Arg Arg Glu
65                  70                  75                  80

His Pro His Pro Thr Ala Arg Pro Trp Arg Ala Asp Asp Ile Leu Ala
                85                  90                  95

Ser Pro Pro Arg Leu Pro Glu Pro Gln Pro Tyr Pro Gly Ala Pro His
            100                 105                 110

His Ser Ser Tyr Val His Leu Arg Pro Ala Arg Pro Thr Ser Pro Pro
        115                 120                 125

Ala His Ser His Arg Asp Phe Gln Pro Val Leu His Leu Val Ala Leu
    130                 135                 140

Asn Ser Pro Leu Ser Gly Gly Met Arg Gly Ile Arg Gly Ala Asp Phe
145                 150                 155                 160

Gln Cys Phe Gln Gln Ala Arg Ala Val Gly Leu Ala Gly Thr Phe Arg
                165                 170                 175

Ala Phe Leu Ser Ser Arg Leu Gln Asp Leu Tyr Ser Ile Val Arg Arg
            180                 185                 190

Ala Asp Arg Ala Ala Val Pro Ile Val Asn Leu Lys Asp Glu Leu Leu
        195                 200                 205

Phe Pro Ser Trp Glu Ala Leu Phe Ser Gly Ser Glu Gly Pro Leu Lys
    210                 215                 220

Pro Gly Ala Arg Ile Phe Ser Phe Asp Gly Lys Asp Val Leu Arg His
225                 230                 235                 240

Pro Thr Trp Pro Gln Lys Ser Val Trp His Gly Ser Asp Pro Asn Gly
                245                 250                 255

Arg Arg Leu Thr Glu Ser Tyr Cys Glu Thr Trp Arg Thr Glu Ala Pro
            260                 265                 270

Ser Ala Thr Gly Gln Ala Ser Ser Leu Leu Gly Gly Arg Leu Leu Gly
        275                 280                 285

Gln Ser Ala Ala Ser Cys His His Ala Tyr Ile Val Leu Cys Ile Glu
    290                 295                 300

Asn Ser Phe Met Thr Ala Ser Lys Asp Asp Asp Asp Lys Gly Gly
305                 310                 315                 320

Gly Gly Ser Glu Pro Lys Ser Gln Asp Lys Thr His Thr Cys Pro Pro
                325                 330                 335

Cys Pro Ala Pro Glu Leu Leu Gly Gly Pro Ser Val Phe Leu Phe Pro
             340                 345                 350

Pro Lys Pro Lys Asp Thr Leu Met Ile Ser Arg Thr Pro Glu Val Thr
             355                 360                 365

Cys Val Val Val Asp Val Ser His Glu Asp Pro Glu Val Lys Phe Asn
             370                 375                 380

Trp Tyr Val Asp Gly Val Glu Val His Asn Ala Lys Thr Lys Pro Arg
385                 390                 395                 400

Glu Glu Gln Tyr Asn Ser Thr Tyr Arg Val Val Ser Val Leu Thr Val
             405                 410                 415

Leu His Gln Asp Trp Leu Asn Gly Lys Glu Tyr Lys Cys Lys Val Ser
             420                 425                 430

Asn Lys Ala Leu Pro Ala Pro Ile Glu Lys Thr Ile Ser Lys Ala Lys
             435                 440                 445

Gly Gln Pro Arg Glu Pro Gln Val Tyr Thr Leu Pro Pro Cys Arg Asp
             450                 455                 460

Glu Leu Thr Lys Asn Gln Val Ser Leu Trp Cys Leu Val Lys Gly Phe
465                 470                 475                 480

Tyr Pro Ser Asp Ile Ala Val Glu Trp Glu Ser Asn Gly Gln Pro Glu
             485                 490                 495

Asn Asn Tyr Lys Thr Thr Pro Pro Val Leu Asp Ser Asp Gly Ser Phe
             500                 505                 510

Phe Leu Tyr Ser Lys Leu Thr Val Asp Lys Ser Arg Trp Gln Gln Gly
             515                 520                 525

Asn Val Phe Ser Cys Ser Val Met His Glu Ala Leu His Asn His Tyr
             530                 535                 540

Thr Gln Lys Ser Leu Ser Leu Ser Pro Gly Lys
545                 550                 555

<210> SEQ ID NO 32
<211> LENGTH: 237
<212> TYPE: PRT
<213> ORGANISM: Artificial Sequence
<220> FEATURE:
<223> OTHER INFORMATION: Heterodimeric NC1-Fc, Molecule 1, Chain 2

<400> SEQUENCE: 32

Gly Gly Gly Gly Ser Glu Pro Lys Ser Gln Asp Lys Thr His Thr Cys
1               5                   10                  15

Pro Pro Cys Pro Ala Pro Glu Leu Leu Gly Gly Pro Ser Val Phe Leu
             20                  25                  30

Phe Pro Pro Lys Pro Lys Asp Thr Leu Met Ile Ser Arg Thr Pro Glu
             35                  40                  45

Val Thr Cys Val Val Val Asp Val Ser His Glu Asp Pro Glu Val Lys
             50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
             85                  90                  95

Thr Val Leu His Gln Asp Trp Leu Asn Gly Lys Glu Tyr Lys Cys Lys
             100                 105                 110

Val Ser Asn Lys Ala Leu Pro Ala Pro Ile Glu Lys Thr Ile Ser Lys
             115                 120                 125

Ala Lys Gly Gln Pro Arg Glu Pro Gln Val Cys Thr Leu Pro Pro Ser
             130                 135                 140

```
Arg Asp Glu Leu Thr Lys Asn Gln Val Ser Leu Ser Cys Ala Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Val Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 33
<211> LENGTH: 555
<212> TYPE: PRT
<213> ORGANISM: Artificial Sequence
<220> FEATURE:
<223> OTHER INFORMATION: Homodimeric NC1-Fc, Molecule 2, Chain 1

<400> SEQUENCE: 33

Ser Gly Val Arg Leu Trp Ala Thr Arg Gln Ala Met Leu Gly Gln Val
1               5                   10                  15

His Glu Val Pro Glu Gly Trp Leu Ile Phe Val Ala Glu Gln Glu Glu
            20                  25                  30

Leu Tyr Val Arg Val Gln Asn Gly Phe Arg Lys Val Gln Leu Glu Ala
        35                  40                  45

Arg Thr Pro Leu Pro Arg Gly Thr Asp Asn Glu Val Ala Ala Leu Gln
    50                  55                  60

Pro Pro Val Val Gln Leu His Asp Ser Asn Pro Tyr Pro Arg Arg Glu
65                  70                  75                  80

His Pro His Pro Thr Ala Arg Pro Trp Arg Ala Asp Asp Ile Leu Ala
                85                  90                  95

Ser Pro Pro Arg Leu Pro Glu Pro Gln Pro Tyr Pro Gly Ala Pro His
            100                 105                 110

His Ser Ser Tyr Val His Leu Arg Pro Ala Arg Pro Thr Ser Pro Pro
        115                 120                 125

Ala His Ser His Arg Asp Phe Gln Pro Val Leu His Leu Val Ala Leu
    130                 135                 140

Asn Ser Pro Leu Ser Gly Gly Met Arg Gly Ile Arg Gly Ala Asp Phe
145                 150                 155                 160

Gln Cys Phe Gln Gln Ala Arg Ala Val Gly Leu Ala Gly Thr Phe Arg
                165                 170                 175

Ala Phe Leu Ser Ser Arg Leu Gln Asp Leu Tyr Ser Ile Val Arg Arg
            180                 185                 190

Ala Asp Arg Ala Ala Val Pro Ile Val Asn Leu Lys Asp Glu Leu Leu
        195                 200                 205

Phe Pro Ser Trp Glu Ala Leu Phe Ser Gly Ser Glu Gly Pro Leu Lys
    210                 215                 220

Pro Gly Ala Arg Ile Phe Ser Phe Asp Gly Lys Asp Val Leu Arg His
225                 230                 235                 240

Pro Thr Trp Pro Gln Lys Ser Val Trp His Gly Ser Asp Pro Asn Gly
                245                 250                 255

Arg Arg Leu Thr Glu Ser Tyr Cys Glu Thr Trp Arg Thr Glu Ala Pro
            260                 265                 270
```

```
Ser Ala Thr Gly Gln Ala Ser Ser Leu Leu Gly Gly Arg Leu Leu Gly
        275                 280                 285

Gln Ser Ala Ala Ser Cys His His Ala Tyr Ile Val Leu Cys Ile Glu
    290                 295                 300

Asn Ser Phe Met Thr Ala Ser Lys Asp Asp Asp Asp Lys Gly Gly
305                 310                 315                 320

Gly Gly Ser Glu Pro Lys Ser Gln Asp Lys Thr His Thr Cys Pro Pro
                325                 330                 335

Cys Pro Ala Pro Glu Leu Leu Gly Gly Pro Ser Val Phe Leu Phe Pro
            340                 345                 350

Pro Lys Pro Lys Asp Thr Leu Met Ile Ser Arg Thr Pro Glu Val Thr
        355                 360                 365

Cys Val Val Val Asp Val Ser His Glu Asp Pro Glu Val Lys Phe Asn
    370                 375                 380

Trp Tyr Val Asp Gly Val Glu Val His Asn Ala Lys Thr Lys Pro Arg
385                 390                 395                 400

Glu Glu Gln Tyr Asn Ser Thr Tyr Arg Val Val Ser Val Leu Thr Val
                405                 410                 415

Leu His Gln Asp Trp Leu Asn Gly Lys Glu Tyr Lys Cys Lys Val Ser
            420                 425                 430

Asn Lys Ala Leu Pro Ala Pro Ile Glu Lys Thr Ile Ser Lys Ala Lys
        435                 440                 445

Gly Gln Pro Arg Glu Pro Gln Val Tyr Thr Leu Pro Pro Cys Arg Asp
    450                 455                 460

Glu Leu Thr Lys Asn Gln Val Ser Leu Trp Cys Leu Val Lys Gly Phe
465                 470                 475                 480

Tyr Pro Ser Asp Ile Ala Val Glu Trp Glu Ser Asn Gly Gln Pro Glu
                485                 490                 495

Asn Asn Tyr Lys Thr Thr Pro Pro Val Leu Asp Ser Asp Gly Ser Phe
            500                 505                 510

Phe Leu Tyr Ser Lys Leu Thr Val Asp Lys Ser Arg Trp Gln Gln Gly
        515                 520                 525

Asn Val Phe Ser Cys Ser Val Met His Glu Ala Leu His Asn His Tyr
    530                 535                 540

Thr Gln Lys Ser Leu Ser Leu Ser Pro Gly Lys
545                 550                 555

<210> SEQ ID NO 34
<211> LENGTH: 555
<212> TYPE: PRT
<213> ORGANISM: Artificial Sequence
<220> FEATURE:
<223> OTHER INFORMATION: Homodimeric NC1-Fc, Molecule 2, Chain 2

<400> SEQUENCE: 34

Ser Gly Val Arg Leu Trp Ala Thr Arg Gln Ala Met Leu Gly Gln Val
1               5                   10                  15

His Glu Val Pro Glu Gly Trp Leu Ile Phe Val Ala Glu Gln Glu Glu
            20                  25                  30

Leu Tyr Val Arg Val Gln Asn Gly Phe Arg Lys Val Gln Leu Glu Ala
        35                  40                  45

Arg Thr Pro Leu Pro Arg Gly Thr Asp Asn Glu Val Ala Ala Leu Gln
    50                  55                  60

Pro Pro Val Val Gln Leu His Asp Ser Asn Pro Tyr Pro Arg Arg Glu
65                  70                  75                  80
```

```
His Pro His Pro Thr Ala Arg Pro Trp Arg Ala Asp Asp Ile Leu Ala
                85                  90                  95

Ser Pro Pro Arg Leu Pro Glu Pro Gln Pro Tyr Pro Gly Ala Pro His
            100                 105                 110

His Ser Ser Tyr Val His Leu Arg Pro Ala Arg Pro Thr Ser Pro Pro
        115                 120                 125

Ala His Ser His Arg Asp Phe Gln Pro Val Leu His Leu Val Ala Leu
130                 135                 140

Asn Ser Pro Leu Ser Gly Gly Met Arg Gly Ile Arg Gly Ala Asp Phe
145                 150                 155                 160

Gln Cys Phe Gln Gln Ala Arg Ala Val Gly Leu Ala Gly Thr Phe Arg
                165                 170                 175

Ala Phe Leu Ser Ser Arg Leu Gln Asp Leu Tyr Ser Ile Val Arg Arg
            180                 185                 190

Ala Asp Arg Ala Ala Val Pro Ile Val Asn Leu Lys Asp Glu Leu Leu
        195                 200                 205

Phe Pro Ser Trp Glu Ala Leu Phe Ser Gly Ser Glu Gly Pro Leu Lys
210                 215                 220

Pro Gly Ala Arg Ile Phe Ser Phe Asp Gly Lys Asp Val Leu Arg His
225                 230                 235                 240

Pro Thr Trp Pro Gln Lys Ser Val Trp His Gly Ser Asp Pro Asn Gly
                245                 250                 255

Arg Arg Leu Thr Glu Ser Tyr Cys Glu Thr Trp Arg Thr Glu Ala Pro
            260                 265                 270

Ser Ala Thr Gly Gln Ala Ser Ser Leu Leu Gly Gly Arg Leu Leu Gly
        275                 280                 285

Gln Ser Ala Ala Ser Cys His His Ala Tyr Ile Val Leu Cys Ile Glu
290                 295                 300

Asn Ser Phe Met Thr Ala Ser Lys Asp Asp Asp Asp Lys Gly Gly
305                 310                 315                 320

Gly Gly Ser Glu Pro Lys Ser Gln Asp Lys Thr His Thr Cys Pro Pro
                325                 330                 335

Cys Pro Ala Pro Glu Leu Leu Gly Gly Pro Ser Val Phe Leu Phe Pro
            340                 345                 350

Pro Lys Pro Lys Asp Thr Leu Met Ile Ser Arg Thr Pro Glu Val Thr
        355                 360                 365

Cys Val Val Val Asp Val Ser His Glu Asp Pro Glu Val Lys Phe Asn
370                 375                 380

Trp Tyr Val Asp Gly Val Glu Val His Asn Ala Lys Thr Lys Pro Arg
385                 390                 395                 400

Glu Glu Gln Tyr Asn Ser Thr Tyr Arg Val Val Ser Val Leu Thr Val
                405                 410                 415

Leu His Gln Asp Trp Leu Asn Gly Lys Glu Tyr Lys Cys Lys Val Ser
            420                 425                 430

Asn Lys Ala Leu Pro Ala Pro Ile Glu Lys Thr Ile Ser Lys Ala Lys
        435                 440                 445

Gly Gln Pro Arg Glu Pro Gln Val Cys Thr Leu Pro Pro Ser Arg Asp
450                 455                 460

Glu Leu Thr Lys Asn Gln Val Ser Leu Ser Cys Ala Val Lys Gly Phe
465                 470                 475                 480

Tyr Pro Ser Asp Ile Ala Val Glu Trp Glu Ser Asn Gly Gln Pro Glu
                485                 490                 495
```

-continued

Asn Asn Tyr Lys Thr Thr Pro Pro Val Leu Asp Ser Asp Gly Ser Phe
            500                 505                 510

Phe Leu Val Ser Lys Leu Thr Val Asp Lys Ser Arg Trp Gln Gln Gly
        515                 520                 525

Asn Val Phe Ser Cys Ser Val Met His Glu Ala Leu His Asn His Tyr
        530                 535                 540

Thr Gln Lys Ser Leu Ser Leu Ser Pro Gly Lys
545                 550                 555

<210> SEQ ID NO 35
<211> LENGTH: 424
<212> TYPE: PRT
<213> ORGANISM: Artificial Sequence
<220> FEATURE:
<223> OTHER INFORMATION: Heterodimeric Fc-Endostatin, Molecule 3, Chain
      1

<400> SEQUENCE: 35

Glu Pro Lys Ser Gln Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Cys Arg Asp Glu Leu Thr
130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Gly Gly Gly Ser Gly Gly Gly Gly
225                 230                 235                 240

Ser His Ser His Arg Asp Phe Gln Pro Val Leu His Leu Val Ala Leu
                245                 250                 255

Asn Ser Pro Leu Ser Gly Gly Met Arg Gly Ile Arg Gly Ala Asp Phe
            260                 265                 270

Gln Cys Phe Gln Gln Ala Arg Ala Val Gly Leu Ala Gly Thr Phe Arg
        275                 280                 285

Ala Phe Leu Ser Ser Arg Leu Gln Asp Leu Tyr Ser Ile Val Arg Arg
290                 295                 300

```
Ala Asp Arg Ala Ala Val Pro Ile Val Asn Leu Lys Asp Glu Leu Leu
305                 310                 315                 320

Phe Pro Ser Trp Glu Ala Leu Phe Ser Gly Ser Glu Gly Pro Leu Lys
                325                 330                 335

Pro Gly Ala Arg Ile Phe Ser Phe Asp Gly Lys Asp Val Leu Arg His
            340                 345                 350

Pro Thr Trp Pro Gln Lys Ser Val Trp His Gly Ser Asp Pro Asn Gly
        355                 360                 365

Arg Arg Leu Thr Glu Ser Tyr Cys Glu Thr Trp Arg Thr Glu Ala Pro
    370                 375                 380

Ser Ala Thr Gly Gln Ala Ser Ser Leu Leu Gly Gly Arg Leu Leu Gly
385                 390                 395                 400

Gln Ser Ala Ala Ser Cys His His Ala Tyr Ile Val Leu Cys Ile Glu
                405                 410                 415

Asn Ser Phe Met Thr Ala Ser Lys
                420

<210> SEQ ID NO 36
<211> LENGTH: 241
<212> TYPE: PRT
<213> ORGANISM: Artificial Sequence
<220> FEATURE:
<223> OTHER INFORMATION: Heterodimeric Fc-Endostatin, Molecule 3, Chain
      2

<400> SEQUENCE: 36

Glu Pro Lys Ser Gln Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Asp Glu Leu Thr
130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Gly Gly Gly Ser Gly Gly Gly Gly
```

```
225             230             235             240
Ser
```

<210> SEQ ID NO 37
<211> LENGTH: 539
<212> TYPE: PRT
<213> ORGANISM: Artificial Sequence
<220> FEATURE:
<223> OTHER INFORMATION: Monomeric NC1-Fc, Molecule 4, Chain 1

<400> SEQUENCE: 37

```
Ser Gly Val Arg Leu Trp Ala Thr Arg Gln Ala Met Leu Gly Gln Val
1               5                   10                  15

His Glu Val Pro Glu Gly Trp Leu Ile Phe Val Ala Glu Gln Glu Glu
            20                  25                  30

Leu Tyr Val Arg Val Gln Asn Gly Phe Arg Lys Val Gln Leu Glu Ala
        35                  40                  45

Arg Thr Pro Leu Pro Arg Gly Thr Asp Asn Glu Val Ala Ala Leu Gln
    50                  55                  60

Pro Pro Val Val Gln Leu His Asp Ser Asn Pro Tyr Pro Arg Arg Glu
65                  70                  75                  80

His Pro His Pro Thr Ala Arg Pro Trp Arg Ala Asp Asp Ile Leu Ala
                85                  90                  95

Ser Pro Pro Arg Leu Pro Glu Pro Gln Pro Tyr Pro Gly Ala Pro His
            100                 105                 110

His Ser Ser Tyr Val His Leu Arg Pro Ala Arg Pro Thr Ser Pro Pro
        115                 120                 125

Ala His Ser His Arg Asp Phe Gln Pro Val Leu His Leu Val Ala Leu
    130                 135                 140

Asn Ser Pro Leu Ser Gly Gly Met Arg Gly Ile Arg Gly Ala Asp Phe
145                 150                 155                 160

Gln Cys Phe Gln Gln Ala Arg Ala Val Gly Leu Ala Gly Thr Phe Arg
                165                 170                 175

Ala Phe Leu Ser Ser Arg Leu Gln Asp Leu Tyr Ser Ile Val Arg Arg
            180                 185                 190

Ala Asp Arg Ala Ala Val Pro Ile Val Asn Leu Lys Asp Glu Leu Leu
        195                 200                 205

Phe Pro Ser Trp Glu Ala Leu Phe Ser Gly Ser Glu Gly Pro Leu Lys
    210                 215                 220

Pro Gly Ala Arg Ile Phe Ser Phe Asp Gly Lys Asp Val Leu Arg His
225                 230                 235                 240

Pro Thr Trp Pro Gln Lys Ser Val Trp His Gly Ser Asp Pro Asn Gly
                245                 250                 255

Arg Arg Leu Thr Glu Ser Tyr Cys Glu Thr Trp Arg Thr Glu Ala Pro
            260                 265                 270

Ser Ala Thr Gly Gln Ala Ser Ser Leu Leu Gly Gly Arg Leu Leu Gly
        275                 280                 285

Gln Ser Ala Ala Ser Cys His His Ala Tyr Ile Val Leu Cys Ile Glu
    290                 295                 300

Asn Ser Phe Met Thr Ala Ser Lys Gly Gly Gly Ser Gly Gly Gly
305                 310                 315                 320

Gly Ser Ala Pro Glu Leu Leu Gly Gly Pro Ser Val Phe Leu Phe Pro
                325                 330                 335

Pro Lys Pro Lys Asp Thr Leu Tyr Ile Thr Arg Glu Pro Glu Val Thr
            340                 345                 350
```

```
Cys Val Val Asp Val Ser His Glu Asp Pro Glu Val Lys Phe Asn
        355                 360                 365

Trp Tyr Val Asp Gly Val Glu Val His Asn Ala Lys Thr Lys Pro Arg
    370                 375                 380

Glu Glu Gln Tyr Asn Ser Thr Tyr Arg Val Val Ser Val Leu Thr Val
385                 390                 395                 400

Leu His Gln Asp Trp Leu Asn Gly Lys Glu Tyr Lys Cys Lys Val Ser
                405                 410                 415

Asn Lys Ala Leu Pro Ala Pro Ile Glu Lys Thr Ile Ser Lys Ala Lys
            420                 425                 430

Gly Gln Pro Arg Glu Pro Gln Val Tyr Thr Leu Pro Pro Ser Arg Asp
        435                 440                 445

Glu Leu Thr Lys Asn Gln Val Ser Leu Thr Cys Leu Val Lys Gly Phe
    450                 455                 460

Tyr Pro Ser Asp Ile Ala Val Glu Trp Glu Ser Asn Gly Gln Pro Glu
465                 470                 475                 480

Asn Asn Tyr Lys Thr Thr Pro Pro Val Leu Asp Ser Asp Gly Ser Phe
                485                 490                 495

Arg Leu Tyr Ser Lys Leu Thr Val Asp Lys Ser Arg Trp Gln Gln Gly
            500                 505                 510

Asn Val Phe Ser Cys Ser Val Met His Glu Ala Leu His Asn His Tyr
        515                 520                 525

Thr Gln Lys Ser Leu Ser Leu Ser Pro Gly Lys
    530                 535

<210> SEQ ID NO 38
<211> LENGTH: 409
<212> TYPE: PRT
<213> ORGANISM: Artificial Sequence
<220> FEATURE:
<223> OTHER INFORMATION: Monomeric Fc-Endostatin, Molecule 5, Chain 1

<400> SEQUENCE: 38

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Arg Leu
                165                 170                 175
```

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Gly Gly Gly Ser Gly Gly Gly
    210                 215                 220

Gly Ser His Ser His Arg Asp Phe Gln Pro Val Leu His Leu Val Ala
225                 230                 235                 240

Leu Asn Ser Pro Leu Ser Gly Gly Met Arg Gly Ile Arg Gly Ala Asp
                245                 250                 255

Phe Gln Cys Phe Gln Gln Ala Arg Ala Val Gly Leu Ala Gly Thr Phe
            260                 265                 270

Arg Ala Phe Leu Ser Ser Arg Leu Gln Asp Leu Tyr Ser Ile Val Arg
            275                 280                 285

Arg Ala Asp Arg Ala Ala Val Pro Ile Val Asn Leu Lys Asp Glu Leu
            290                 295                 300

Leu Phe Pro Ser Trp Glu Ala Leu Phe Ser Gly Ser Glu Gly Pro Leu
305                 310                 315                 320

Lys Pro Gly Ala Arg Ile Phe Ser Phe Asp Gly Lys Asp Val Leu Arg
                325                 330                 335

His Pro Thr Trp Pro Gln Lys Ser Val Trp His Gly Ser Asp Pro Asn
            340                 345                 350

Gly Arg Arg Leu Thr Glu Ser Tyr Cys Glu Thr Trp Arg Thr Glu Ala
            355                 360                 365

Pro Ser Ala Thr Gly Gln Ala Ser Ser Leu Leu Gly Gly Arg Leu Leu
            370                 375                 380

Gly Gln Ser Ala Ala Ser Cys His His Ala Tyr Ile Val Leu Cys Ile
385                 390                 395                 400

Glu Asn Ser Phe Met Thr Ala Ser Lys
                405

<210> SEQ ID NO 39
<211> LENGTH: 340
<212> TYPE: PRT
<213> ORGANISM: Artificial Sequence
<220> FEATURE:
<223> OTHER INFORMATION: Cloned Mouse NC1 - PRT

<400> SEQUENCE: 39

Met Gly Trp Ser Cys Ile Ile Leu Phe Leu Val Ala Thr Ala Thr Gly
1               5                   10                  15

Val His Ser His His His His His Ala Gly Gln Val Arg Ile Trp
            20                  25                  30

Ala Thr Tyr Gln Thr Met Leu Asp Lys Ile Arg Glu Val Pro Glu Gly
            35                  40                  45

Trp Leu Ile Phe Val Ala Glu Arg Glu Leu Tyr Val Arg Val Arg
    50                  55                  60

Asn Gly Phe Arg Lys Val Leu Leu Glu Ala Arg Thr Ala Leu Pro Arg
65                  70                  75                  80

Gly Thr Gly Asn Glu Val Ala Ala Leu Gln Pro Pro Leu Val Gln Leu
                85                  90                  95

His Glu Gly Ser Pro Tyr Thr Arg Arg Glu Tyr Ser Tyr Ser Thr Ala
            100                 105                 110

Arg Pro Trp Arg Ala Asp Asp Ile Leu Ala Asn Pro Pro Arg Leu Pro
            115                 120                 125

```
Asp Arg Gln Pro Tyr Pro Gly Val Pro His His Ser Ser Tyr Val
    130                 135                 140

His Leu Pro Pro Ala Arg Pro Thr Leu Ser Leu Ala His Thr His Gln
145                 150                 155                 160

Asp Phe Gln Pro Val Leu His Leu Val Ala Leu Asn Thr Pro Leu Ser
                165                 170                 175

Gly Gly Met Arg Gly Ile Arg Gly Ala Asp Phe Gln Cys Phe Gln Gln
            180                 185                 190

Ala Arg Ala Val Gly Leu Ser Gly Thr Phe Arg Ala Phe Leu Ser Ser
        195                 200                 205

Arg Leu Gln Asp Leu Tyr Ser Ile Val Arg Arg Ala Asp Arg Gly Ser
    210                 215                 220

Val Pro Ile Val Asn Leu Lys Asp Glu Val Leu Ser Pro Ser Trp Asp
225                 230                 235                 240

Ser Leu Phe Ser Gly Ser Gln Gly Gln Leu Gln Pro Gly Ala Arg Ile
                245                 250                 255

Phe Ser Phe Asp Gly Arg Asp Val Leu Arg His Pro Ala Trp Pro Gln
            260                 265                 270

Lys Ser Val Trp His Gly Ser Asp Pro Ser Gly Arg Arg Leu Met Glu
        275                 280                 285

Ser Tyr Cys Glu Thr Trp Arg Thr Glu Thr Thr Gly Ala Thr Gly Gln
    290                 295                 300

Ala Ser Ser Leu Leu Ser Gly Arg Leu Leu Glu Gln Lys Ala Ala Ser
305                 310                 315                 320

Cys His Asn Ser Tyr Ile Val Leu Cys Ile Glu Asn Ser Phe Met Thr
                325                 330                 335

Ser Phe Ser Lys
            340

<210> SEQ ID NO 40
<211> LENGTH: 1047
<212> TYPE: DNA
<213> ORGANISM: Artificial Sequence
<220> FEATURE:
<223> OTHER INFORMATION: Cloned Mouse NC1 - DNA

<400> SEQUENCE: 40
gaattcccgc cgccaccatg gctggtcct gcatcattct gtttctggtg gccacagcca    60
ccggcgtgca ctctcaccat caccatcatc acgctggcca agtgcggatc tgggccacct   120
atcagaccat gctggacaag atcagagagg tgcccgaagg ctggctgatc ttcgtggccg   180
aacgggaaga actgtacgtc agagtgcgga acggcttcag aaaggtgctg ctggaagcca   240
gaacagccct gctagaggc acaggcaatg aagtggctgc tctgcagcct cctctggtcc    300
aactgcacga gggcagccct tacaccagaa gagagtacag ctacagcacc gccagacctt   360
ggagagccga cgacattctg gccaatcctc aagactgcc cgacagacag ccttatcctg    420
gcgtgccaca ccaccacagc agctatgttc atctgcctcc agccagacct acactgagcc   480
tggctcacac ccaccaggat ttccagcctg tgctgcatct ggtggctctg aacacacctc   540
tgagcggcgg catgagagga atcagaggcg ccgatttcca gtgctttcag caggccagag   600
ccgtgggcct gagcggaact tttagagcct tcctgagcag cagactgcag gacctgtaca   660
gcattgtgcg gagggccgat agaggcagcg tgcccattgt gaacctgaag gacgaggtgc   720
tgagcccctc ttgggatagc ctgtttagcg gctctcaggg ccaactgcaa ccaggcgcca   780
```

-continued

```
gaatcttcag cttcgacggc agagatgtgc tgagacaccc tgcctggcct cagaaatctg    840
tgtggcatgg cagcgaccca tctggcagac ggctgatgga agctactgc gagacatggc     900 ggaccgagac aacaggcgct acaggacagg caagctctct gctgagtggc agactgctgg    960
aacagaaggc cgccagctgc cacaacagct acatcgtgct gtgcatcgag aacagcttca   1020
tgaccagctt cagcaagtga taagctt                                        1047
```

<210> SEQ ID NO 41
<211> LENGTH: 337
<212> TYPE: PRT
<213> ORGANISM: Artificial Sequence
<220> FEATURE:
<223> OTHER INFORMATION: Cloned Human NC1 - PRT

<400> SEQUENCE: 41

```
Met Gly Trp Ser Cys Ile Ile Leu Phe Leu Val Ala Thr Ala Thr Gly
1               5                   10                  15

Val His Ser His His His His His His Ser Gly Val Arg Leu Trp Ala
            20                  25                  30

Thr Arg Gln Ala Met Leu Gly Gln Val His Glu Val Pro Glu Gly Trp
        35                  40                  45

Leu Ile Phe Val Ala Glu Gln Glu Leu Tyr Val Arg Val Gln Asn
    50                  55                  60

Gly Phe Arg Lys Val Gln Leu Glu Ala Arg Thr Pro Leu Pro Arg Gly
65                  70                  75                  80

Thr Asp Asn Glu Val Ala Ala Leu Gln Pro Pro Val Val Gln Leu His
                85                  90                  95

Asp Ser Asn Pro Tyr Pro Arg Arg Glu His Pro His Pro Thr Ala Arg
            100                 105                 110

Pro Trp Arg Ala Asp Asp Ile Leu Ala Ser Pro Pro Arg Leu Pro Glu
        115                 120                 125

Pro Gln Pro Tyr Pro Gly Ala Pro His His Ser Ser Tyr Val His Leu
    130                 135                 140

Arg Pro Ala Arg Pro Thr Ser Pro Pro Ala His Ser His Arg Asp Phe
145                 150                 155                 160

Gln Pro Val Leu His Leu Val Ala Leu Asn Ser Pro Leu Ser Gly Gly
                165                 170                 175

Met Arg Gly Ile Arg Gly Ala Asp Phe Gln Cys Phe Gln Gln Ala Arg
            180                 185                 190

Ala Val Gly Leu Ala Gly Thr Phe Arg Ala Phe Leu Ser Ser Arg Leu
        195                 200                 205

Gln Asp Leu Tyr Ser Ile Val Arg Arg Ala Asp Arg Ala Ala Val Pro
    210                 215                 220

Ile Val Asn Leu Lys Asp Glu Leu Leu Phe Pro Ser Trp Glu Ala Leu
225                 230                 235                 240

Phe Ser Gly Ser Glu Gly Pro Leu Lys Pro Gly Ala Arg Ile Phe Ser
                245                 250                 255

Phe Asp Gly Lys Asp Val Leu Arg His Pro Thr Trp Pro Gln Lys Ser
            260                 265                 270

Val Trp His Gly Ser Asp Pro Asn Gly Arg Arg Leu Thr Glu Ser Tyr
        275                 280                 285

Cys Glu Thr Trp Arg Thr Glu Ala Pro Ser Ala Thr Gly Gln Ala Ser
    290                 295                 300

Ser Leu Leu Gly Gly Arg Leu Leu Gly Gln Ser Ala Ala Ser Cys His
305                 310                 315                 320
```

```
His Ala Tyr Ile Val Leu Cys Ile Glu Asn Ser Phe Met Thr Ala Ser
            325                 330                 335
Lys

<210> SEQ ID NO 42
<211> LENGTH: 1038
<212> TYPE: DNA
<213> ORGANISM: Artificial Sequence
<220> FEATURE:
<223> OTHER INFORMATION: Cloned Human NC1 - DNA

<400> SEQUENCE: 42
gaattcccgc cgccaccatg ggctggtcct gcatcattct gtttctggtg gccacagcca     60
ccggcgtgca ctctcaccat caccatcatc atagcggcgt gcggctgtgg gctacaagac    120
aggctatgct gggacaagtg cacgaggtgc cagaaggctg gctgatcttt gtggccgagc    180
aagaggaact gtacgtgcgg gtgcagaacg gcttcagaaa ggtgcagctg gaagccagaa    240
cacccctgcc tagaggcacc gacaatgaag tggctgctct gcagcctcct gtggtgcagc    300
tccacgacag caaccectat cctagaagag agcaccctca tcctaccgcc agaccttgga    360
gagccgacga cattctggcc tctccaccta gactgcctga gcctcagcct tatcctggcg    420
ctcctcacca cagcagctat gtgcatctga ggcctgccag acctacaagc cctcctgctc    480
acagccacag agacttccag cctgtgctgc atctggtggc tctgaactct cctctgtccg    540
gcggcatgag aggaatcaga ggcgccgatt ccagtgctt ccagcaggcc agagctgttg    600
gactggccgg aaccttcaga gccttcctgt ctagcagact gcaggacctg tacagcatcg    660
tgcgcagagc cgatagagcc gccgtgccta tcgtgaacct gaaggacgag ctgctgttcc    720
ctagctggga agccctgttt agcggctctg agggacctct gaaaccaggc gccagaatct    780
tcagcttcga cggcaaggac gtgctgagac accctacctg gcctcagaaa tctgtgtggc    840
acggcagcga cccaacgga agaaggctga cagagagcta ctgcgaaacc tggcggacag    900
aagccccatc tgcaacagga caggccagct ctttgctcgg aggtagactg cttggacaga    960
gcgccgcctc ttgtcaccac gcctatatcg tgctgtgcat cgagaacagc ttcatgaccg   1020
ccagcaagtg ataagctt                                                  1038
```

MEANS AND METHODS FOR THE TREATMENT OF ANGIOGENESIS-, FIBROSIS- AND CANCER-RELATED DISEASES WITH PROTEIN OLIGOMERS COMPRISING NC-1-FC

CROSS-REFERENCE TO RELATED APPLICATIONS

This application is a U.S. National Phase of International PCT Application No. PCT/EP2019/059747 filed Apr. 16, 2019, which claims priority to European Patent Application Serial No. 18167832.7 filed Apr. 17, 2018, the contents of each application are incorporated herein by reference in their entirety.

The present invention pertains to a method for producing a protein oligomer comprising at least two, and preferably three heterodimeric human NC-1-Fc proteins, the method comprising: a) culturing a host cell expressing (i) a fusion protein comprising, from N- to C-terminus, human NC-1 from collagen 18 fused to human IgG1 Fc with "knob" mutations, or human IgG1 Fc with "knob" mutations fused to human NC-1 from collagen 18, and (ii) human IgG1 Fc with "hole" mutations, under conditions which allow the formation of a protein oligomer comprising at least two, and preferably three heterodimeric human NC-1-Fc proteins, and wherein the fusion protein of (i) and the human IgG1 Fc with "hole" mutations of (ii) are expressed in a ratio of 2:1 or higher, and b) obtaining from the host cell of step a) the protein oligomer comprising at least two, and preferably three heterodimeric human NC-1-Fc proteins. The invention further relates to a method for producing a protein oligomer comprising at least two, and preferably three monomeric human NC-1-Fc proteins, the method comprising: a) culturing a host cell expressing a fusion protein comprising, from N- to C-terminus, human NC-1 from collagen 18 fused to human IgG1 Fc, or human IgG1 Fc fused to human NC-1 from collagen 18, wherein the human IgG1 Fc comprises at least one monomeric mutation, preferably the monomeric mutation F405R, and one or more half-life extension mutations, preferably the half-life extension mutations M252Y, S254T and T256E, under conditions which allow the formation of a protein oligomer comprising at least two, and preferably three monomeric human NC-1-Fc proteins, and b) obtaining from the host cell of step a) the protein oligomer comprising at least two, and preferably three monomeric human NC-1-Fc proteins. Furthermore, the invention provides for a protein oligomer comprising at least two, and preferably three heterodimeric human NC-1-Fc proteins for use in treating, ameliorating or preventing an angiogenesis-related disease, wherein the heterodimeric human NC-1-Fc protein comprises (i) a fusion protein comprising, from N- to C-terminus, human NC-1 from collagen 18 fused to human IgG1 Fc with "knob" mutations, or human IgG1 Fc with "knob" mutations fused to human NC-1 from collagen 18, and (ii) the human IgG1 Fc with "hole" mutations, wherein the "knob" mutations and "hole" mutations in human IgG1 Fc are defined as set forth in the present application. The invention also concerns a monomeric NC-1-Fc protein, comprising human NC-1 from collagen 18 and a Fc domain from human IgG1, wherein the Fc domain from human IgG1 comprises at least one monomeric mutation, preferably the monomeric mutation F405R, and one or more half-life extension mutations, preferably the half-life extension mutations M252Y, S254T and T256E. The invention also relates to a protein oligomer comprising at least two of said monomeric human NC-1-Fc fusion proteins for use as a medicament, preferably for treating an angiogenesis-related disease, fibrosis or a fibrosis-associated disease, vascular endothelial growth factor (VEGF)-related disease or matrix metalloproteinase (MMP)-related disease.

Original recombinant endostatin produced 1997 by Folkman laboratory (O'Reilly et al., Cell 88(2): 277-85, 1997) was a non-soluble aggregate generated in $E.\ coli$ that was injected s.c. into mice. Subsequently, soluble endostatin was produced in yeast. The Entremed monomeric endostatin lacks in a substantial portion of the critical N-terminal Zn2+ binding domain. This one showed moderate response in Phase I trials and the production was so expensive that only few trials were conducted (for review see Abdollahi DRU 2015 PMID: 15939343).

Chinese scientists developed Endostar by adding a His-tag to the N-terminus, leading to better solubilization, and found a refolding procedure to produce endostatin monomer in bacterial culture, which was effective and received Chinese FDA approval, in non-small cell lung cancer (U.S. Pat. No. 7,078,485B2).

Therefore, even production of endostatin constituted a challenge. Dr. Javaherian developed together with Lexigen, later Merck KGa, the Fc-endostatin originally to circumvent two obstacles, i.e., improve expression of large amount of endostatin for clinical trial level production using the conventional well established antibody production platforms. Furthermore, later studies revealed a better half-life (Lee et al. CCR 14(5): 1487-93, 2008) which was another argument for Fc-endostatin over only 30 min to 1 h half-life of the recombinant endostatin molecule.

Production of collagen 18 NC-1 which includes the endostatin domain was from the beginning a big challenge due to aggregation of the molecule over the oligomerization domain. Therefore, no-in-vivo data exist on the efficacy of recombinant NC-1 and only little research was conducted on this so far believed precursor molecule to endostatin.

Dr. Javaherian and few other labs were able to express very little of recombinant NC-1 by His-tag or Flag-tag, but it was never enough for a preclinical dosing of animals. Therefore, production of NC-1 amounts relevant for in-vivo studies still constitute a major challenge.

In light of the above, there is a need in the art for the development of effective methods for producing NC-1 in amounts sufficient for preclinical and clinical studies.

The technical problem underlying the present invention could be seen as the provision of means and methods which comply with the afore-mentioned needs. This technical problem has been solved by the embodiments characterized in the claims and herein below.

Accordingly, the present invention relates to a method for producing a protein oligomer comprising at least two, and preferably three heterodimeric human NC-1-Fc proteins, the method comprising:

a) culturing a host cell expressing (i) a fusion protein comprising, from N- to C-terminus, human NC-1 from collagen 18 fused to human IgG1 Fc with "knob" mutations, or human IgG1 Fc with "knob" mutations fused to human NC-1 from collagen 18, and (ii) human IgG1 Fc with "hole" mutations, under conditions which allow the formation of a protein oligomer comprising at least two, and preferably three heterodimeric human NC-1-Fc proteins, and wherein the fusion protein of (i) and the human IgG1 Fc with "hole" mutations of (ii) are expressed in a ratio of 2:1 or higher, and b) obtaining from the host cell of step a) the protein oligomer comprising at least two, and preferably three heterodimeric human NC-1-Fc proteins.

In this method of the invention, a protein oligomer is produced. The protein oligomer comprises at least two heterodimeric human NC-1-Fc proteins but can comprise also more than two heterodimeric human NC-1-Fc proteins, such as three, four, five, six or even more heterodimeric human NC-1-Fc proteins. Preferably, the protein oligomer comprises three heterodimeric human NC-1-Fc proteins.

Figure 9:
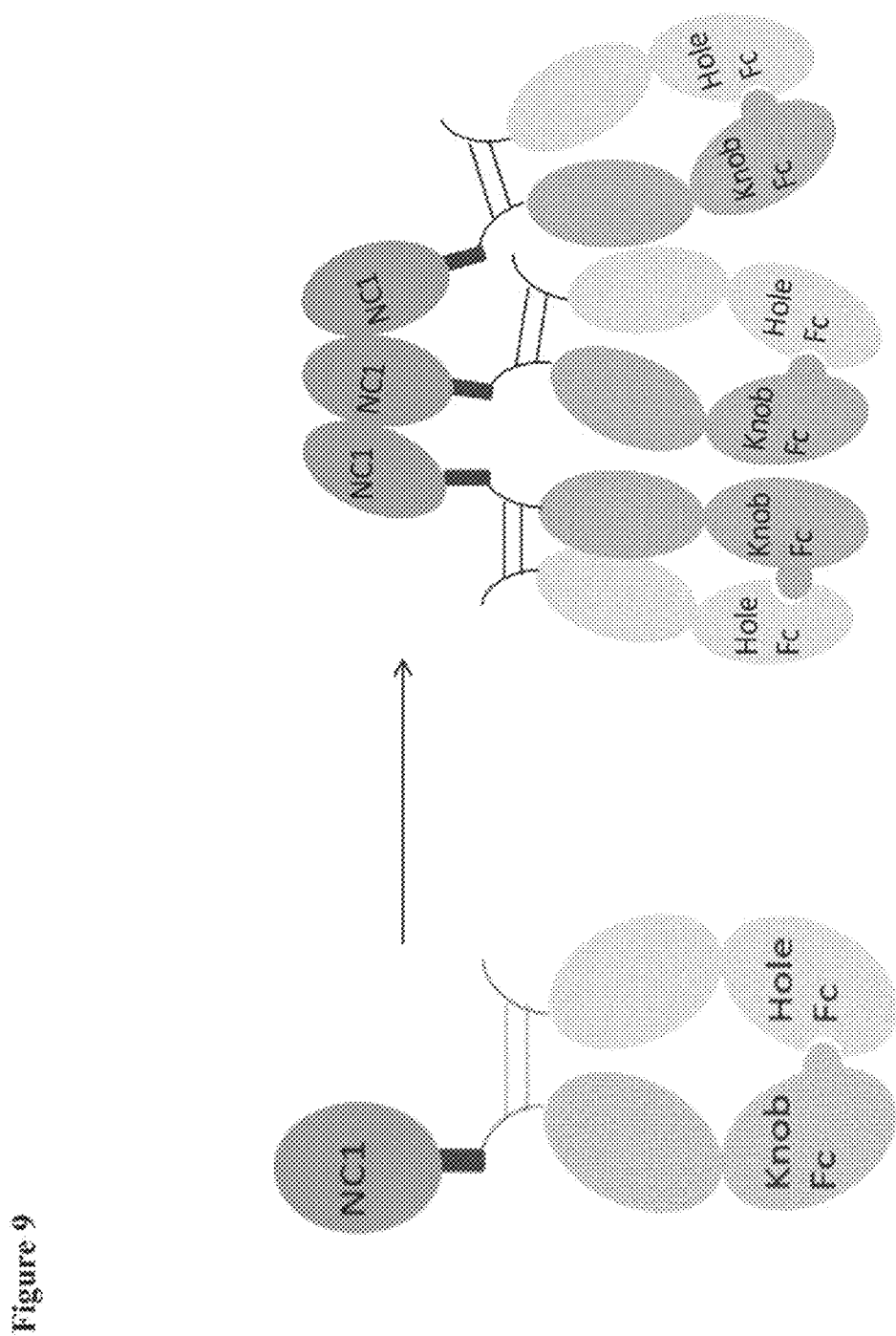

A heterodimeric human NC-1-Fc protein and a protein oligomer encompassing three heterodimeric human NC-1-Fc proteins are illustrated in FIG. 9.

The heterodimeric human NC-1-Fc protein comprises (i) a fusion protein comprising, from N- to C-terminus, human NC-1 from collagen 18 fused to human IgG1 Fc with "knob" mutations, or a fusion protein comprising, from N-terminus to C-terminus, human IgG1 Fc with "knob" mutations fused to human NC-1 from collagen 18. The Fc "knobs-into-holes" (KiH) strategy is well known in the art and explained elsewhere herein. Said fusion protein (i) is also referred to herein as "NC-1-Fc-knob", if human NC-1 from collagen 18 is positioned at the N-terminus, and human IgG1 Fc with "knob" mutations is located at the C-terminus of the fusion protein. Accordingly, "Fc-knob-NC-1" corresponds to a fusion protein in which human IgG1 Fc with "knob" mutations is located at the N-terminus, and human NC-1 from collagen 18 is positioned at the C-terminus of the fusion protein.

The heterodimeric human NC-1-Fc protein further comprises (ii) a Fc domain from IgG1 with "hole" mutations. Said Fc domain (ii) is also referred to herein as "Fc-hole".

The heterodimeric human NC-1-Fc protein comprising (i) NC-1-Fc-knob or Fc-knob-NC-1 and (ii) Fc-hole is also referred to herein as "NC-1-Fc-KiH" or "NC-1-Fc(KiH)".

NC-1 and IgG1 Fc are human or derived from human. The term "derived from" is explained elsewhere herein. The "knob" and "hole" mutations in the Fc domains of IgG1 allow the formation of a Fc dimer.

The fusion protein (i) comprising, from N- to C-terminus, human NC-1 from collagen 18 fused to human IgG1 Fc with "knob" mutations, or human IgG1 Fc with "knob" mutations fused to human NC-1 from collagen 18, and (ii) human IgG1 Fc with "hole" mutations are expressed in a host cell under conditions which allow the formation of a protein oligomer wherein the protein oligomer comprises at least two or more heterodimeric human NC-1-Fc proteins. To this end, the host cell can, e.g., be co-transfected with two different expression vectors, one comprising the nucleic acid sequence encoding the fusion protein (i) comprising, from N- to C-terminus, human NC-1 from collagen 18 fused to human IgG1 Fc with "knob" mutations, or human IgG1 Fc with "knob" mutations fused to human NC-1 from collagen 18, under the control of a suitable promoter, and the other expression vector comprising (ii) human IgG1 Fc with "hole" mutations under the control of an appropriate promoter. However, it is evident to those skilled in the art that the host cell can also be transfected with a single expression vector containing both the nucleic acid sequence encoding the fusion protein (i) comprising, from N- to C-terminus, human NC-1 from collagen 18 fused to human IgG1 Fc with "knob" mutations, or human IgG1 Fc with "knob" mutations fused to human NC-1 from collagen 18, and (ii) the human IgG1 Fc with "hole" mutations, under the control of suitable promoters.

It has been found by the present inventors that it is important that the fusion protein (i) comprising, from N- to C-terminus, human NC-1 from collagen 18 fused to human IgG1 Fc with "knob" mutations, or human IgG1 Fc with "knob" mutations fused to human NC-1 from collagen 18, and the human IgG1 Fc with "hole" mutations of (ii) are expressed in a ratio of 2:1 or higher, such as 3:1 or 4:1 or even higher, in order to prevent dimerization of two human IgG1 Fc domains with "hole" mutations ("hole-hole Fc dimers") and to achieve efficient production of the heterodimeric human NC-1-Fc protein which then forms the protein oligomer with the desired biological activities, as explained elsewhere herein and shown in the following Examples. Put in other words: the fusion protein (i) comprising, from N- to C-terminus, human NC-1 from collagen 18 fused to human IgG1 Fc with "knob" mutations, or human IgG1 Fc with "knob" mutations fused to human NC-1 from collagen 18, has to be expressed in excess in the host cell, in comparison to human IgG1 Fc with "hole" mutations (ii). The desired ratio of the fusion protein (i) comprising, from N- to C-terminus, human NC-1 fused to human IgG1 Fc with "knob" mutations, or human IgG1 Fc with "knob" mutations fused to human NC-1 from collagen 18, and the human IgG1 Fc with "hole" mutations of (ii) of 2:1 or higher can be achieved, e.g., by using appropriate promoters directing the expression with different promoter strength.

To achieve the desired ratio, the present inventors utilized double the amount of the "knob" plasmid for transient expression systems. They also utilized multiplicity of infection (MOI) up to 4:1 for "knob":"hole" by using two different viral particles, each harboring a construct. In an alternative approach one could also include the NC-1-Fc-knob or Fc-knob-NC-1 construct and the Fc-hole in double promoter systems, for transient transfection and stable cell generation, as mentioned above. Then not the amount of DNA (transient) or MOI (virus) needs to be in more than 2:1 in favor of the NC-1-Fc-knob or Fc-knob-NC-1 construct, but rather this could be controlled by different promoter strengths, e.g. CMV "knob" vs. EF1 "hole" etc.

Preferably, the fusion protein (i) comprising, from N- to C-terminus, human NC-1 from collagen 18 fused to human IgG1 Fc with "knob" mutations, or human IgG1 Fc with "knob" mutations fused to human NC-1 from collagen 18, and the human IgG1 Fc with "hole" mutations of (ii) are expressed in a ratio of higher than 2:1. Ratios equal to or higher than 5:1 might be contra-productive, due to aggregation of the NC-1 oligomerization domain in "knob" constructs. Accordingly, the preferred ratio is 2:1, 3:1 or 4:1.

Finally, the protein oligomer comprising at least two, or more heterodimeric human NC-1-Fc proteins are obtained from the host cell by methods well known in the art; see, e.g., Sambrook et al., Molecular cloning:a laboratory manual/Sambrook, Joseph; Russell, David W. --. 3rd ed. —New York: Cold Spring Harbor Laboratory, 2001. Ausubel et al., Current Protocols in Molecular Biology. To obtain the protein oligomer comprising at least two heterodimeric human NC-1-Fc proteins from the host cell or supernatant, the present inventors performed protein A purification and size-exclusion chromatography, indicating two peaks at 1:1 ratio. The first peak was the envisioned heterodimeric construct, the second consisted of "hole-hole dimers". Accordingly, the inventors moved to 2:1 "knob" vs. "hole" to augment NC-1-Fc-knob production which almost diminished the formation of a second peak (Fc-hole-dimers). Anyway, heterodimeric NC-1-Fc-KiH could be well separated by the first peak in a fraction collector.

In a preferred embodiment of the method of the invention for producing a protein oligomer comprising at least two heterodimeric human NC-1-Fc proteins, the method further comprises a step c) wherein the formation of a (preferred) trimer is tested by crosslinking non-denatured heterodimeric human NC-1-Fc proteins. How to carry out crosslinking experiments of non-denatured proteins is well described in the art. Crosslinking has been carried out by the present inventors to ensure that the natural protein structure (esp. tertiary and quaternary) is not lost upon electrophoresis. Crosslinking was, therefore, performed to identify the in-vivo composition of this molecule, which was found to form a trimer in the same manner as the natural or native NC-1 domain. Said method is preferably employed in the production process of the therapeutic substance to assure that indeed an NC-1-trimer is formed in the production process of future production pipelines.

In another preferred embodiment of the method of the invention for producing a protein oligomer comprising at least two heterodimeric human NC-1-Fc proteins, the human IgG1 Fc comprises the "knob" mutations S354C/T366W, and the human IgG1 Fc the "hole" mutations Y349C/T366S/L368A/Y407V.

Preferably, the human IgG1 Fc with the "knob" mutations S354C/T366W comprises SEQ ID NO: 25, and the human IgG1 Fc with "hole" mutations Y349C/T366S/L368A/Y407V comprises SEQ ID NO: 26.

More preferably, the fusion protein (i) comprising, from N- to C-terminus, human NC-1 from collagen 18 fused to human IgG1 Fc with "knob" mutations comprises or consists of SEQ ID NO: 27, 29, or 31, and the human IgG1 Fc with "hole" mutations of (ii) comprises or consists of SEQ ID NO: 28, 30, or 32.

Particularly preferred, the fusion protein (i) comprising, from N- to C-terminus, human NC-1 from collagen 18 fused to human IgG1 Fc with "knob" mutations comprises or consists of SEQ ID NO: 31, and the human IgG1 Fc with "hole" mutations of (ii) comprises or consists of SEQ ID NO: 32 (see FIG. 9 and Table 1, Molecule #1).

In a still further embodiment of the method of the invention for producing a protein oligomer comprising at least two heterodimeric human NC-1-Fc proteins, KiH-engineered human IgG4 Fc is used, instead of KiH-engineered human IgG1 Fc. The "knob" and "hole" mutations in the Fc domains of IgG4 allow the formation of a Fc dimer. The corresponding amino acid sequence of human IgG4 Fc is shown, e.g., in FIG. 6 of US 2013/0177555A1.

Moving from endostatin to NC-1 as an antiangiogenic and anticancer drug was the first major step by the inventors of the present application; see WO 2013/026913 and WO 2017/093569.

Since this discovery, these inventors have spent almost a decade now to achieve a system for large scale production of NC-1, and failed with numerous constructs and classical tags, as demonstrated herein and the following Examples.

The inventors' major aim was to move in the area of immunoglobulin IgG Fc conjugation with numerous biotechnological, pharmacokinetic as well as biological advantages.

However, generation of NC-1-Fc is not a straight forward process and not at all something that would be apparent for a person skilled in the art to pursue.

The reason for this is that there are two oligomerization forces, one trimerization and aggregation force induced by the NC-1 oligomerization (or association) domain, and a second dimerization force induced by the IgG-Fc. The inventors have spent tremendous time with all different existing technologies, i.e., C- or N-terminal conjugation of NC-1 to standard IgG Fc fusion, like previously performed with endostatin, and all these approaches failed, as explained in the following Examples.

One has to consider that in classical Fc-tagging approaches, one would produce an N- or C-terminal conjugated NC-1 molecule that without the NC-1 oligomerization domain would form a dimer. However, with NC-1 oligomerization domain one receives aggregates and very pure expression.

To the inventors' best knowledge, there is no existing literature about successful and efficient production of NC-1-Fc fusion proteins and oligomers containing the same.

As described herein, the present inventors have studied different approaches to circumvent this main issue and after a decade of research are able to present a successful strategy. One central point was to generate dimeric Fc-monovalent NC-1, or heterodimeric NC-1-Fc. The inventors decided to use a mutation in Fc that precludes dimerization of NC-1-Fc with NC-1-Fc, using the Fc "Knobs-in-Holes" (KiH) strategy. Hence, NC-1-Fc-knob would only dimerize with empty Fc-hole. While knob-knob dimerization is prohibited, hole-hole dimerization could still occur at lower levels. Indeed, the inventors found two peaks, one being the envisioned NC-1-Fc-KiH heterodimer, and a second peak being Fc-hole-hole dimers (see Examples below). This indicated that NC-1-Fc-knob was more difficult for cells to be expressed. The inventors again circumvented this problem by increasing the expression of NC-1-Fc-knob vs. Fc-hole (e.g., 2:1, 3:1, 4:1 or higher), this leads to mainly one peak of NC-1-Fc-KiH heterodimer with excellent expression efficacy. However, in size exclusion column (SEC) the inventors recognized that the molecule under physiologic condition is much larger than one would expect from a NC-1-Fc-KiH heterodimer (see the following Examples). Subsequent crosslinking experiment confirmed that the inventors have strikingly achieved to produce a trimeric molecule, i.e., a trimer of NC-1-Fc-KiH heterodimer. This molecule preserves all excellent properties of Fc plus the trimeric NC-1. Strikingly, this trimeric NC-1-Fc-KiH molecule demonstrates the same efficacy in binding unique oligomeric NC-1 binding partners, such as fibronectin, VEGF, and MMP-2/9. With excellent expression ratio and availability of sufficient amount of recombinant NC-1, the inventors have now after long time the possibility to perform in-vivo experiments in different disease models with this NC-1 molecule. In addition to the data in lung cancer (LLC) model and the lung fibrosis model, further experiments are ongoing and will tremendously improve the inventors' understanding of this molecule.

Of note, separate expression of NC-1-Fc-knob and NC-1-Fc-hole and later dimerization via redox system all failed to produce an efficient NC-1-Fc construct. Hence, the steric hindrance of a heterodimeric Fc was crucial for the success and lack of aggregation. Next, the inventors aimed to evaluate whether adding moieties to the "empty" Fc-hole will affect the expression of the molecule. To this end, they conjugated classical Fab fragment of antibody to the Fc-hole and co-expressed it with NC-1-Fc-knob. Intriguingly, addition of a steric hindrance by a Fab moiety NC-1-Fc-KiH-Fab decreased the efficiency of expression compared to NC-1-Fc-KiH heterodimer, as shown in the Examples and Table 6.

Together, the trimeric NC-1-Fc-KiH heterodimer reported by the inventors is the first NC-1-based Fc construct which could be expressed in sufficient amounts for preclinical and clinical studies, and given the 3D complexities of both NC-1 and Fc engineering such a molecule was and is not a trivial process that one would be able to deduce from current literature.

The invention further relates to a method for producing a protein oligomer comprising at least two, and preferably three monomeric human NC-1-Fc proteins, the method comprising:

a) culturing a host cell expressing a fusion protein comprising, from N- to C-terminus, human NC-1 from collagen 18 fused to human IgG1 Fc, or human IgG1 Fc fused to human NC-1 from collagen 18, wherein the human IgG1 Fc comprises at least one monomeric mutation, preferably the monomeric mutation F405R, and one or more half-life extension mutations, preferably the half-life extension mutations M252Y, S254T and T256E, under conditions which allow the formation of a protein oligomer comprising at least two, and preferably three monomeric human NC-1-Fc proteins, and b) obtaining from the host cell of step a) the protein oligomer comprising at least two, and preferably three monomeric human NC-1-Fc proteins.

Also in this method of the invention, a protein oligomer is produced. The protein oligomer comprises at least two monomeric human NC-1-Fc proteins but can comprise also more than two monomeric human NC-1-Fc proteins, such as three, four, five, six or even more monomeric human NC-1-Fc proteins. Preferably, the protein oligomer comprises three monomeric human NC-1-Fc proteins.

Figure 10:
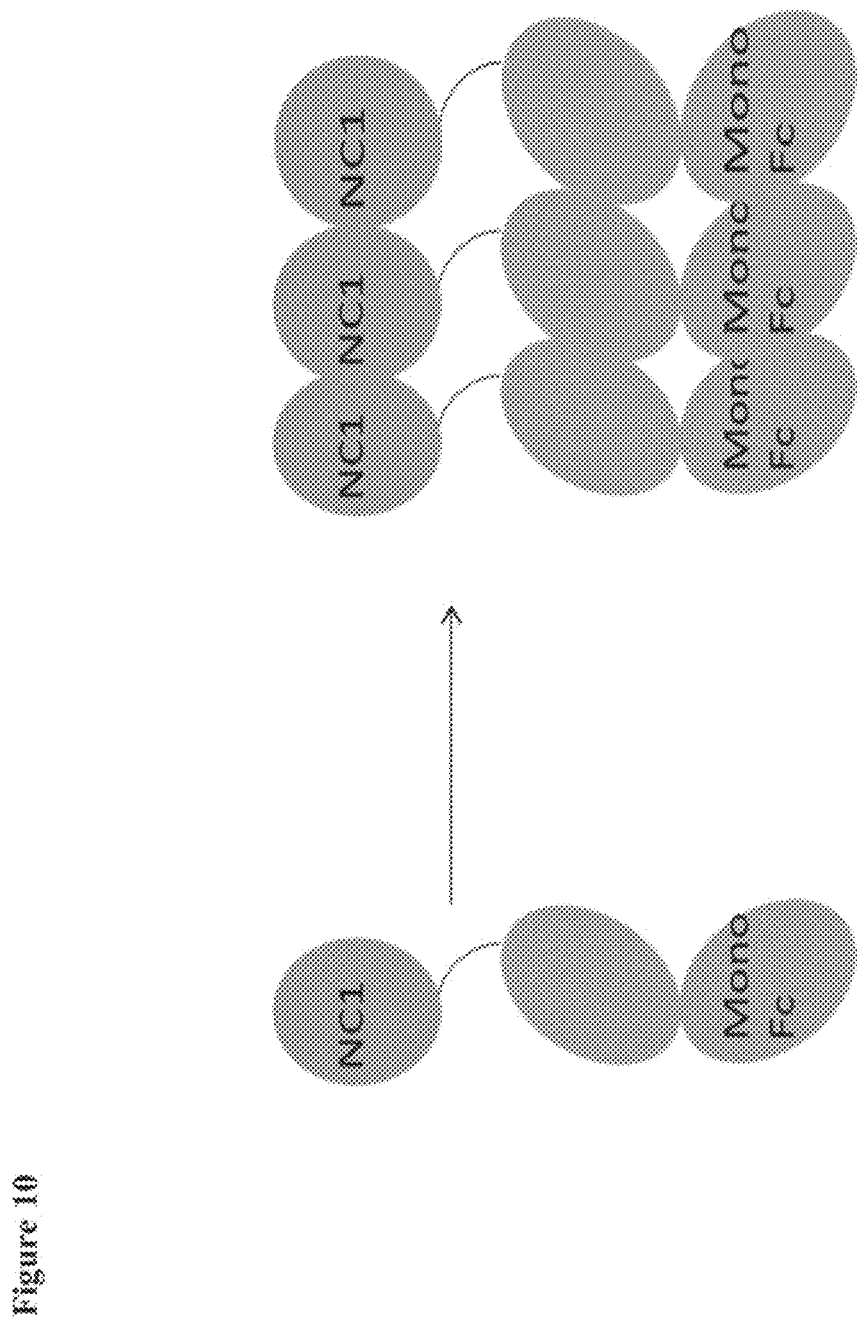

A monomeric human NC-1-Fc protein and a protein oligomer encompassing three monomeric human NC-1-Fc proteins are illustrated in FIG. 10.

The monomeric human NC-1-Fc protein comprises a fusion protein comprising, from the N-terminus to the C-terminus, human NC-1 from collagen 18 fused to human IgG1 Fc, or human IgG1 Fc fused to human NC-1 from collagen 18. The monomeric human NC-1-Fc protein is also referred to herein as "NC-1-Fc(mono)".

The human IgG1 Fc comprises one or more monomeric mutation(s), which means that the human IgG1 Fc domain is engineered to a monomeric Fc in that one, two, three, four, five or even more critical amino acid residues at positions located on the human IgG1 Fc dimerization interface are mutated. A human IgG1 Fc carrying one or more of such monomeric mutation(s) is no longer able to dimerize with another human IgG1 Fc domain but only forms a monomer. An example for such a mutation is the monomeric mutation F405R.

Evidently, a fusion protein comprising, from N- to C-terminus, human NC-1 from collagen 18 fused to human IgG1 Fc, or human IgG1 Fc fused to human NC-1 from collagen 18, wherein the human IgG1 Fc comprises one or more monomeric mutation(s) is no longer able to dimerize with another human IgG1 Fc. However, such a fusion protein is able to oligomerize with other fusion proteins comprising, from N- to C-terminus, human NC-1 from collagen 18 fused to human IgG1 Fc, or human IgG1 Fc fused to human NC-1 from collagen 18, wherein the human IgG1 Fc comprises one or more monomeric mutation(s), via the oligomerization domain of NC-1, as shown in the following Examples, FIG. 10 and Table 4 (Molecule #4, SEQ ID NO: 37).

The human IgG1 Fc further comprises one, two, three, four, five or even more half-life extension mutations, such as the mutations M252Y, S254T and/or T256E (YTE). Half-life extension mutations have been reported to enhance binding to the neonatal Fc receptor (FcRn) and increase serum half-life, in comparison to wild-type IgG1 (Dall'Acqua et al., J Biol Chem. 2006 Aug. 18; 281(33): 23514-24. Epub 2006 Jun. 21).

As appreciated by those skilled in the art IgG1 is not an obligation for generation of monomeric Fc, and IgG4 could be used here as well. For example, there is an approach by MedImmune which can be used in context of NC-1. IgG4 naturally falls apart into half-antibodies and then quickly reforms, this process is known as Fab-arm exchange and was first reported by van der Neut Kolfschoten et al., Science. 2007 Sep. 14; 317(5844):1554-7 and then later by Labrijn et al., Nat Biotechnol. 2009 August; 27(8):767-71. doi: 10.1038/nbt.1553. Epub 2009 Jul. 20. For this reason, MedImmune selected IgG4 as starting point to generate monomeric Fc as it was easier to prevent this dimerizing than IgG1. However, it turned out that some of the mutations discovered work for both human IgG4 and IgG1 (even mouse IgG1 do work in this format as well). One would select a human IgG4 for a blocking antibody (i.e. no ADCC or CDC) and IgG1 to activate the immune response. In case of NC-1-Fc, the present inventors have no evidence yet how much the oligomerization over NC-1 conserves the avidity and retain the ADCC potential of the compound. If ADCC plays no role, one could also possibly pursue an IgG4-based strategy.

Accordingly, in another embodiment of this method of the invention, a human IgG4 Fc comprising at least one monomeric mutation, and one or more half-life extension mutations, can be used, instead of human IgG1 Fc; see, e.g., US 2013/0177555.

In addition to the human IgG1 Fc comprising the monomeric mutation F405R, and the half-life extension mutations M252Y, S254T and T256E (Shan L, Colazet M, Rosenthal K L, Yu X-Q, Bee J S, Ferguson A, et al. (2016) Generation and Characterization of an IgG4 Monomeric Fc Platform. PLoS ONE 11(8): e0160345), the present inventors have tested so far an approach as reported by Wilkinson et al. (MAbs. 2013 May 1; 5(3): 406-417; US20130177555) as an alternative.

Other possible alternatives are provided by the studies presented by Ying et al. (The Journal of Biological Chemistry 287, 19399-19408; and Tianlei Ying, Yang Feng, Yanping Wang, Weizao Chen & Dimiter S. Dimitrov (2014). Monomeric IgG1 Fc molecules displaying unique Fc receptor interactions that are exploitable to treat inflammation-mediated diseases, mAbs, 6:5, 1201-1210), US 2013/0177555 and U.S. Pat. No. 9,200,060.

Preferably, the human IgG1 Fc comprises the monomeric mutation F405R and the half-life extension mutations M252Y, S254T and T256E (YTE).

The aforementioned fusion protein is expressed in a host cell under conditions which allow for the formation of a protein oligomer wherein the protein oligomer comprises at least two or more monomeric human NC-1-Fc proteins.

Preferably, the monomeric human NC-1-Fc protein comprises or consists of SEQ ID NO: 37.

Finally, the protein oligomer comprising at least two, or more monomeric human NC-1-Fc proteins is obtained from the host cell by methods well known in the art; see, e.g., Sambrook et al., Molecular cloning:a laboratory manual/ Sambrook, Joseph; Russell, David W. --. 3rd ed. —New York: Cold Spring Harbor Laboratory, 2001; Ausubel et al., Current Protocols in Molecular Biology. Here, the present inventors have received a trimeric molecule consisting of three NC1-Fc(mono), as shown in the following Examples.

In a preferred embodiment, the methods of the invention are in vitro methods.

A monomeric NC-1-Fc fusion protein could successfully be produced by the present inventors using the monomeric mutation F405R and YTE-mutated IgG1 Fc domain carrying the half-life extension mutations M252Y, S254T and T256E (see, e.g., WO2013/096291A2) (see FIG. 10 and Table 4, Molecule #4, SEQ ID NO: 37). Oligomerization via the NC-1 oligomerization domain results in the formation of a trimeric NC-1 with one monomeric Fc domain each. This fusion protein could be produced highly efficient by transient expression (30 mg/l). Monomeric Fc is not able to elicit antibody-dependent cell-mediated cytotoxicity (ADCC), under standard conditions. It is currently under investigation, if the trimerization of the Fc domains via NC-1 can increase the avidity, possibly resulting in antibody-dependent cell-mediated cytotoxicity (ADCC).

Taken together, after having failed with numerous constructs and classical tags for almost a decade now, the present inventors finally managed to achieve systems for large scale production of NC-1. In addition, the inventors unexpectedly found that protein oligomers with the heterodimeric NC-1-Fc or monomeric NC-1-Fc proteins presented herein show a higher efficacy in initial preclinical tumor models and fibrosis studies, in comparison to homodimeric Fc-endostatin (Fc-ES, U.S. Pat. No. 8,703,908B2, US20130165634A1), as demonstrated in the following Examples and FIGS. 7 and 8.

The term "protein" or "polypeptide" or "(poly)peptide" or "peptide" (all terms are used interchangeably, if not indicated otherwise) as used herein encompasses isolated and/or purified (poly)peptides being essentially free of other host cell polypeptides. The term "peptide" as referred to herein comprises at least two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 45, 50, 60, 70, 80, 90, 100, 150, 200, 250, 300 or even more amino acid residues where the alpha carboxyl group of one is bound to the alpha amino group of another. A post-translational modification of the protein or peptide as used and envisaged herein is the modification of a newly formed protein or peptide and may involve deletion, substitution or addition of amino acids, chemical modification of certain amino acids, for example, amidation, acetylation, phosphorylation, glycosylation, formation of pyroglutamate, oxidation/reduction of sulfa group on a methionine, or addition of similar small molecules, to certain amino acids.

The term "protein" or "peptide" as used herein encompasses peptidomimetics. As known in the art, peptidomimetics are compounds whose essential elements (pharmacophore) mimic a natural peptide or protein in 3D space and which retain the ability to interact with the biological target (such as Fibronectin, VEGF, MMP-2 and/or MMP-9) and produce the same biological effect (for example, anti-fibrotic activity, anti-angiogenic activity, anti-invasive/anti-metastatic activity, reducing vascular permeability activity, anti-inflammatory and anti-tumorigenic activity, induction of antibody-dependent cell-mediated cytotoxicity (ADCC)); see, e.g., the review by Vagner et al. 2008, Current Opinion in Chemical Biology 12, Pages 292-296. Peptidomimetics are designed to circumvent some of the problems associated with a natural peptide, e.g., stability against proteolysis (duration of biological activity) and poor bioavailability. Certain other properties, such as selectivity for the biological target as mentioned above or potency of the biological activity, such as the aforementioned biological activities, often can be substantially improved.

Protein or peptide modifications as used herein include synthetic embodiments of (poly)peptides described herein. In addition, analogs (non-peptide organic molecules), derivatives (chemically functionalized (poly)peptide molecules obtained starting with the disclosed (poly)peptide sequences) and variants (homologs) of these proteins can be utilized in the means and methods and medical and diagnostic uses described herein. Each (poly)peptide of this disclosure is comprised of a sequence of amino acids, which may be either L- and/or D-amino acids, naturally occurring and otherwise. (Poly)peptides can be modified by a variety of chemical techniques to produce derivatives having essentially the same biological activity (for example, anti-fibrotic activity, anti-angiogenic activity, anti-invasive/anti-metastatic activity, reducing vascular permeability activity, anti-inflammatory and anti-tumorigenic activity, and/or induction of antibody-dependent cell-mediated cytotoxicity (ADCC)) as the unmodified (poly)peptides, and optionally having other desirable properties. For example, carboxylic acid groups of the protein, whether carboxyl-terminal or side chain, can be provided in the form of a salt of a pharmaceutically-acceptable cation or esterified to form a C1-C16 ester, or converted to an amide of formula NR1R2 wherein R1 and R2 are each independently H or C1-C16 alkyl, or combined to form a heterocyclic ring, such as a 5- or 6-membered ring. Amino groups of the polypeptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to C1-C16 alkyl or dialkyl amino or further converted to an amide. Hydroxyl groups of the polypeptide side chains may be converted to C1-C16 alkoxy or to a C1-C16 ester using well-recognized techniques. Phenyl and phenolic rings of the polypeptide side chains may be substituted with one or more halogen atoms, such as fluorine, chlorine, bromine or iodine, or with C1-C16 alkyl, C1-C16 alkoxy, carboxylic acids and esters thereof, or amides of such carboxylic acids. Methylene groups of the polypeptide side chains can be extended to homologous C2-C4 alkylenes. Thiols can be protected with any one of a number of well-recognized protecting groups, such as acetamide groups. Those skilled in the art will also recognize methods for introducing cyclic structures into the (poly)peptides of this invention to select and provide conformational constraints to the structure that result in enhanced stability.

The protein or (poly)peptide as referred to herein can also be a fusion protein. The term "fusion protein" as used herein denotes a chimeric protein (literally, made of parts from different sources) which is created through the joining of two or more genes that originally coded for separate proteins. Translation of this fusion gene results in a single or multiple polypeptides with functional properties derived from each of the original proteins. For example, the method of the invention for producing a protein oligomer comprising at least two heterodimeric human NC-1-Fc proteins uses a fusion protein comprising, from N- to C-terminus, human NC-1 from collagen 18 fused to human IgG1 Fc with "knob" mutations. This fusion protein then heterodimerizes with the IgG1 Fc domain comprising the appropriate "hole" mutations, as illustrated in FIG. 9. To provide a further example for a fusion protein, the method of the invention for producing a protein oligomer comprising at least two monomeric human NC-1-Fc proteins uses a fusion protein comprising, from N- to C-terminus, human NC-1 from collagen 18 fused to human IgG1 Fc, wherein the human IgG1 Fc comprises the monomeric mutation F405R, and the half-life extension mutations M252Y, S254T and T256E.

The fusion protein as defined herein can be manufactured by chemical synthesis or recombinant molecular biology techniques well known to the person skilled in the art. This applies mutatis mutandis to the isolation of fusion protein from the host cell or supernatant; see, e.g., Sambrook et al., Molecular cloning: a laboratory manual/Sambrook, Joseph; Russell, David W. --. 3rd ed. —New York: Cold Spring Harbor Laboratory, 2001; Ausubel, Current Protocols in Molecular Biology, Green Publishing Associates and Wiley Interscience, N.Y. (1994).

The fusion protein as defined herein can also comprise a purification tag, a label, or another therapeutic agent, such as an anti-fibrotic agent, an anti-angiogenic agent and/or anti-tumorigenic agent, or the like. A "label" as referred to herein is a detectable compound or composition that is conjugated directly or indirectly to another molecule, such as the fusion protein or protein oligomer as defined herein, to facilitate detection of that molecule. Specific, non-limiting examples of labels include fluorescent tags, enzymatic linkages, and radioactive isotopes well known in the art. In one embodiment, a protease cleavage site and/or linker (i.e. a protease cleavage site; or a linker; or both a protease cleavage site and a linker; or the linker comprises a protease cleavage site) can be present between the NC-1 and Fc domain. The protease cleavage site can be used to cleave off the Fc domain by treatment with proteases, such as enterokinase or thrombin, if desired. For example, the Fc domain can be used as a tag for expression and purification while NC-1 can be isolated post-cleavage with the protease. As well known by the skilled person, besides the basic role in linking the functional domains together (as in flexible and rigid linkers) or releasing free functional domain in vivo (as in in vivo cleavable linkers), linkers may offer many other advantages for the production of fusion proteins, such as improving biological activity, increasing expression yield, and achieving desirable pharmacokinetic profiles. The linker can be, e.g., a protein/peptide linker such as a polyglycine linker or other linker known in the art (see, e.g., Chen et al., Adv Drug Deliv Rev. 2013; 65(10): 1357-1369). Evidently, the linker can be designed in a way that it comprises a protease cleavage site. As appreciated by those skilled in the art, the fusion protein as defined herein does not contain a protease cleavage site and/or linker for clinical use, or the protease cleavage site and/or linker is removed from the fusion protein prior to and for clinical use.

Collagen 18 consists of a central, interrupted triple-helical domain, flanked at the N-terminus (NC-11 domain) and C-terminus (NC-1 domain), by larger non-triple helical, globular structures (Oh et al., PNAS 1994, 91, 4229; Oh et al., Genomics 1994, 19, 494; Abe et al. 1993, Biochem. Biophys. Res. Commun. 196, 576). The Type XVIII collagen belongs to a unique and novel subclass of the collagen superfamily for which the name "MULTIPLEXIN family" has been proposed.

The cloning of the mouse and human collagen 18 proteins has been described by Oh et al. (loc. cit.). The nucleotide and amino acid sequences of mouse collagen 18 are shown in accession number NM_001109991.1, whereas the corresponding human sequences are shown in NM_030582.3. Further, the amino acid sequences of mouse and human collagen 18 are shown in SEQ ID NOs: 1 and 2, respectively.

The "NC-1 domain" (or briefly NC-1 or NC1) as used herein is derived from or is from the C-terminus of collagen 18 and includes (i) an N-terminal association region (of about 50 amino acid residues), (ii) a central protease-sensitive hinge region (of about 70 amino acid residues) and/or (iii) a C-terminal stable endostatin domain (of about 180 amino acid residues) (Sasaki et al., 1998, EMBO J. 17, 4249; WO 2013/026913 and WO 2017/093569). The NC-1 domain (or briefly NC-1 or NC1) as used herein preferably comprises (i) the N-terminal association region, (ii) the central protease-sensitive hinge region and (iii) the C-terminal stable endostatin domain. In other preferred embodiments, the NC-1 domain as used herein comprises (i) the N-terminal association region and (iii) the C-terminal stable endostatin domain in which the central protease-sensitive hinge region (ii) is lacking. Such NC-1 domains without the (ii) the central protease-sensitive hinge region are particularly useful for clinical and therapeutic purposes, due to the lack of this region sensitive to proteases.

The amino acid sequence of the NC-1 domain of the mouse collagen 18 is depicted in SEQ ID NO: 3, whereas the corresponding sequence of the NC-1 domain of human collagen 18 sequence is shown in SEQ ID NO: 4. It is preferred that the NC-1 domain of collagen 18 is human or derived from human.

A (poly)peptide "derived from" the NC-1 domain as used herein means that such a (poly)peptide is identical to or can differ from the corresponding amino acid sequence of the native (poly)peptide in the NC-1 domain, in one, two, three, four, five, six, seven, eight, nine, ten, 15, 20, 25, 30, 35, 40, 50 or even more amino acid residues, while at least maintaining (or even exceeding) the biological activity (as described elsewhere herein) of the corresponding NC-1 domain, such as the oligomerization properties, anti-fibrotic activity, anti-angiogenic activity, anti-invasive/anti-metastatic activity, reducing vascular permeability activity, anti-inflammatory and/or anti-tumorigenic activity. For example, a NC-1 domain derived from human collagen 18 can carry one, two, three, four, five or even more mutations, compared to the native human NC-1 domain. Such mutations are well known in the art and include, e.g., substitutions, additions and/or deletions in the nucleic acid or amino acid sequence of the native (or wildtype) human NC-1. Tests for determining such biological activities are described, e.g., in WO 2013/026913 and WO 2017/093569. The mentioned term (poly)peptide "derived from" the human NC-1 domain comprises variants of the human NC-1 domain. Preferably, the said variant sequence is at least 50%, at least 60%, at least 70%, at least 75%, at least 80%, at least 85%, at least 90%, at least 91%, at least 92%, at least 93%, at least 94%, at least 95%, at least 96%, at least 97%, at least 98% or at least 99% identical to the specific amino acid sequence of the human NC-1 domain as shown in SEQ ID NO: 4, over the entire length. Means and methods for carrying sequence alignments and determining sequence identity are known in the art and described elsewhere herein.

The "association domain" or "association region" or "oligomerization domain" (all terms are interchangeably) of the human NC-1 domain comprising amino acid residues from about 10 to about 60 of the amino acid sequence shown in SEQ ID NO: 4 is responsible for non-covalent trimerization of the NC-1 monomer to form a globular trimer. Accordingly, this association domain functions as a trimerization domain. The proteolytic cleavage-sensitive "hinge region" comprises amino acid residues from about 61 to about 129 of the amino acid sequence shown in SEQ ID NO: 4. The compact "endostatin domain" comprises amino acid residues from about 130 to about 308 of the amino acid sequence shown in SEQ ID NO: 4; see, e.g., Sasaki, loc. cit.; Kuo 2001, JCB 152, 1233; Tjin et al. 2005, Cancer Res 65, 3656. The endostatin domain comprises a zinc binding site which mediates binding to zinc and is located at the N-terminus of endostatin (Ding et al., 1998, PNAS 95, 10443; U.S. Pat. No. 7,524,811). Interestingly, this zinc binding site has been shown to be responsible for the anti-tumor/anti-angiogenic activity of endostatin (Boehm et al., 1998, Biochem. Biophys. Res. Commun. 252, 190). The association region and the endostatin domain in the NC-1 domain are connected by the hinge region (see Sasaki et al., loc. cit.). The hinge region has been found to be cleaved, for instance, by matrix metalloproteinases (MMPs), such as MMP-3, -7, -9, -13 and -20 (Heliasvaara et al., Exp Cell Res 2005, 307, 192).

The term "Fc domain" or "Fc region" as used herein means the fragment crystallizable region which is the tail region of an antibody or immunoglobulin that interacts with cell surface receptors, i.e. Fc receptors, and some proteins of the complement system. This property allows antibodies to activate the immune system. In IgG, IgA and IgD antibody isotypes, the Fc domain is composed of two identical protein fragments, derived from the second and third constant domains of the antibody's two heavy chains; IgM and IgE Fc domains contain three heavy chain constant domains (CH domains 2-4) in each polypeptide chain. The Fc domains of IgGs bear a highly conserved N-glycosylation site. Glycosylation of the Fc fragment is essential for Fc receptor-mediated activity. The N-glycans attached to this site are predominantly core-fucosylated diantennary structures of the complex type. In addition, small amounts of these N-glycans also bear bisecting GlcNAc and α-2,6 linked sialic acid residues. Fusion of the Fc domain of immunoglobulins to proteins has been found to enhance the production and secretion of the fusion proteins in mammalian cells (see, e.g., Lo et al., 1998, Protein Eng. 11, 495, Capon et al., 1989, Nature 337, 525). In addition, linking of angiogenesis inhibitors to an immunoglobulin Fc domain have shown to increase the half life of said inhibitors (see, e.g., Capon et al. 1989, Nature 337, 525; Gordon et al., 2001, J. Clin. Oncol. 19, 843; Holash et al., 2002, Proc. Natl. Acad. Sci. USA 99, 11393). However, the Fc domain can not only be used for purification, solubilization and/or detection purposes but alters advantageously the biological and pharmacokinetic properties of a fusion protein or protein oligomer, as set forth herein and in the following Examples. In one embodiment, the Fc domain can be cleaved off by treatment with proteases, such as enterokinase or thrombin, if desired. As evident to those skilled in the art, in principle, any IgG isoform can be used to generate the protein oligomer or fusion protein as defined herein. Even sub-fragments or single chains of the Fc domain of IgG can be used in order to prolong the half life or oligomerization of the protein oligomer or fusion protein described herein.

It is preferred that the Fc domain as referred to herein is from human IgG or derived from human IgG, such as human IgG1 or IgG4, more preferably from human IgG1 or derived from human IgG1 (Bergers and Javaherian Science 1999; Lee et al Clin Canc Res 2008). The human Fc domain from IgG1 comprises or consists of an amino acid sequence as shown in SEQ ID NO: 6 or SEQ ID NO: 24.

A Fc domain "derived from" human IgG1 or human IgG4 as used herein means that such a Fc domain is identical to or can differ from the corresponding amino acid sequence of the native (poly)peptide in the human IgG1 Fc domain or human IgG4 Fc domain, in one, two, three, four, five, six, seven, eight, nine, ten, 15, 20, 25, 30, 35, 40, 50 or even more amino acid residues, while altering, maintaining or even exceeding the biological activity of the corresponding native human IgG1 Fc domain or human IgG4 Fc domain, such as dimerization property, Fc receptor binding e.g. binding to FcRn and modifying the pharmacokinetic of the construct as well as or induction of antibody-dependent cell-mediated cytotoxicity (ADCC). For example, a Fc domain derived from the human IgG1 Fc domain can carry one, two, three, four, five or even more mutations, compared to the native (or wildtype) human IgG1 Fc domain. Such mutations are well known in the art and include, e.g., substitutions, additions and/or deletions in the nucleic acid or amino acid sequence of the native (or wildtype) human IgG1 Fc domain. The mentioned term (poly)peptide "derived from" the human IgG1 Fc domain comprises variants of the human IgG1 domain. Preferably, the said variant sequence is at least 50%, at least 60%, at least 70%, at least 75%, at least 80%, at least 85%, at least 90%, at least 91%, at least 92%, at least 93%, at least 94%, at least 95%, at least 96%, at least 97%, at least 98% or at least 99% identical to the specific amino acid sequence of the human IgG1 domain as shown in SEQ ID NO: 6 or 24, over the entire length. The mentioned term (poly)peptide "derived from" the human IgG4 Fc domain comprises variants of the human IgG1 domain. Preferably, the said variant sequence is at least 50%, at least 60%, at least 70%, at least 75%, at least 80%, at least 85%, at least 90%, at least 91%, at least 92%, at least 93%, at least 94%, at least 95%, at least 96%, at least 97%, at least 98% or at least 99% identical to the specific amino acid sequence of the human IgG4 domain as shown as shown, e.g., in FIG. 6 of US20130177555A1, over the entire length.

In one aspect, the Fc domain is a "knobs-into-holes" (KiH) engineered Fc domain. A "knobs-into-holes" (KiH) engineered Fc domain has been used by the present inventors to produce protein oligomers comprising heterodimeric NC-1-Fc, as demonstrated in the following Examples. Knobs-into-holes is a well-validated heterodimerization technology for the third constant domain of an antibody. Basically, the concept relies on modifications of the interface between the two CH3 domains where most interactions occur. A bulky residue is introduced into the CH3 domain of one antibody heavy chain and acts similarly to a key. In the other heavy chain, a "hole" is formed that is able to accommodate this bulky residue, mimicking a lock. The resulting heterodimeric Fc-part can be further stabilized by artificial disulfide bridges. During the process of optimizing the heterodimerization interface, various rational designs, including steric complementarity, KiH, disulfide bonds and salt bridges juxtaposing oppositely charged residues on either side of the CH3 domain, were evaluated and ultimately optimized using a phage display library. Correct heavy chain association with heterodimerization yields above 97% can be achieved by introducing six mutations: S354C, T366W in the "knob" heavy chain and Y349C, T366S, L368A, Y407V in the "hole" heavy chain (Klein et al., MAbs. 2012 Nov. 1; 4(6): 653-663; Ridgway et., Protein Eng. 1996 July; 9(7): 617-21). In addition, properties of antibodies with KiH mutations such as (thermal) stability, FcγR binding and effector functions (e.g., antibody-dependent cell-mediated cytotoxicity (ADCC), FcRn binding) and pharmacokinetic (PK) behavior are not affected. The non-covalent interactions, along with disulfide bridges in the hinge region, drive assembly toward heterodimer formation and minimize combinatorial heterogeneity. Suitable KiH-engineered Fc domains are depicted, e.g., in SEQ ID NOs. 25, 26, 28 and 30. For example, SEQ ID NO: 25 shows the amino acid sequence of the human IgG1 Fc with the "knob" mutations S354C/T366W, and SEQ ID NO: 26 depicts the amino acid sequence of the human IgG1 Fc with the "hole" mutations Y349C/T366S/L368A/Y407V.

SEQ ID NO: 27 shows the amino acid sequence of a fusion protein comprising human NC-1 fused via an enterokinase cleavage site and a linker to the human IgG1 Fc with "knob" mutations (S354C/T366W) (from N- to C-terminus). This fusion protein is able to heterodimerize with the human IgG1 Fc with "hole" mutations Y349C/T366S/L368A/Y407V (SEQ ID NO: 28). Such a heterodimer is illustrated in FIG. 9.

SEQ ID NO: 29 shows the amino acid sequence of a fusion protein comprising human IgG1 Fc with "knob" mutations (S354C/T366W) fused via a linker and an enterokinase site to human NC-1 (from N- to C-terminus). This fusion protein is able to heterodimerize with the human IgG1 Fc with "hole" mutations Y349C/T366S/L368A/Y407V (SEQ ID NO: 30).

It has been found by the present inventors that "knobs-into-holes" (KiH)-engineered Fc domains are particularly useful for the production of a protein oligomer comprising at least two or more heterodimeric human NC-1-Fc proteins, as demonstrated in the following Examples. Accordingly, it is preferred that KiH-engineered Fc domains of human immunoglobulins, such as human IgG1 or human IgG4, more preferably KiH-engineered Fc domains of human IgG1 be used for the production of said protein oligomers.

In another aspect, the Fc domain is monomeric, i.e. engineered by mutating critical residues located on the IgG1 or IgG4 Fc dimerization interface. How to produce monomeric IgG1 or monomeric IgG4 is known in the art; see, e.g., Wang et al., Front. Immunol., 13 Nov. 2017.

It has been found by the present inventors that a monomeric Fc domain is particularly useful in producing protein oligomers comprising two or more monomeric NC-1-Fc fusion proteins, as demonstrated in the following Examples. Preferably, the Fc domain is from IgG1 and comprises the mutations F405R corresponding to the monomeric mutation, and mutations M252Y, S254T and T256E corresponding to half-life extension mutations, in the monomeric NC-1-Fc fusion protein(s). Further monomeric NC-1-Fc fusion proteins will be identified using the RCB technology by Selexis.

The term "oligomer" usually refers to a macromolecular complex formed by non-covalent bonding of a few macromolecules like proteins or nucleic acids, in biochemistry. A dimer is per definition a macromolecular complex formed by two, usually non-covalently bound, molecules like proteins or peptides. Such a complex can also be formed by protein domains which are parts of protein sequences and structures that can evolve, function, and exist independently of the rest of the protein chain(s). A homodimer is formed by two identical molecules. The underlying process is called homodimerization. A hetero-dimer is built by two different molecules which are formed by heterodimerization. As known in the art, most dimers or trimers in biochemistry are not connected by covalent bonds, with the exception of disulfide bridges. Some proteins contain specialized domains to ensure dimerization, trimerization or oligomerization, so called dimerization, trimerization or oligomerization domains, as defined herein, and well known in the art. To give an example, dimerization can be mediated by an Fc domain of an immunoglobulin or by disulfide bridges or, both or, other means known in the art. For instance, a heterodimeric human NC-1-Fc protein is illustrated in FIG. 9. Here, the NC-1-Fc-knob dimerizes with Fc-hole.

Accordingly, a trimer is a macromolecular complex formed by three, usually non-covalently bound peptides, proteins or protein domains. A homo-trimer is formed by three identical molecules, whereas a hetero-trimer is built by three different molecules. For instance, collagen 18 is a homo-trimeric protein. A tetramer consists of four molecules, a pentamer of five molecules, and so on. In these cases, complex formation is often mediated by oligomerization domains, as set forth above. For instance, for trimerization, the native association region (or oligomerization domain) within the NC-1 domain can be used which mediates the trimerization of NC-1 of collagen 18 because the native association region within the NC-1 domain of collagen 18 functions as a trimerization domain.

In the context of the present invention, an "oligomer" is to be understood as a "protein oligomer" that comprises a few monomer units, e.g., two, three, four, five or even more monomer units. Accordingly, the oligomer can be, e.g., a dimer, trimer, tetramer, pentamer, and so on. Preferably, the oligomer is a homo-dimer, homo-trimer etc. The monomer unit (or briefly monomer) can be, e.g., a heterodimeric human NC-1-Fc protein or a monomeric NC-1-Fc which can form a trimer via the oligomerization domain of NC-1. The monomer unit "heterodimeric human NC-1-Fc protein" then forms a trimer via the oligomerization (or association) domain of NC-1; see FIG. 9. Also the monomer unit "monomeric NC-1-Fc" forms a trimer via the oligomerization domain of NC-1, as depicted in FIG. 10.

The protein oligomer of the invention has at least one, preferably at least two, more preferably at least three, four, five, particularly preferred all of the following biological activities: anti-fibrotic activity, anti-angiogenic activity, anti-invasive/anti-metastatic activity, reducing vascular permeability activity, anti-inflammatory and/or anti-tumorigenic activity, mediated by oligomeric NC-1. Tests for said biological activities and properties are known in the art; see, e.g., WO 2013/026913 and WO 2017/093569. Further, the protein oligomer of the invention has preferably the capability of inducing antibody-dependent cell-mediated cytotoxicity (ADCC), via the dimerized or oligomerized Fc domains. Means and methods for testing ADCC are well described in the literature (see, e.g., Yamashita et al., Scientific Reports volume 6, Article number: 19772 (2016); doi:10.1038/srep19772; Parekh et al., MAbs. 2012 May 1; 4(3): 310-318. doi: Chung et al., J Immunol Methods. 2014 May; 407:63-75. doi: 10.1016/j.jim.2014.03.021. Epub 2014 Apr. 3; Tada et al. (2014) PLoS ONE 9(4): e95787; PDF available on the Essenbioscience website, entitled Immunce Cell Killing Tumor Spheroids Assay Protocol.

The protein oligomer as defined herein can be manufactured by chemical synthesis or recombinant molecular biology techniques and be isolated from host cells or cell culture supernatants by methods well known in the art; see, e.g., Sambrook et al., Molecular cloning: a laboratory manual/ Sambrook, Joseph; Russell, David W.—3rd ed. —New York: Cold Spring Harbor Laboratory, 2001.

The term "protein oligomer" as used herein includes also protein preparations comprising the protein oligomer and other proteins, agents or compounds, in addition. For example, said protein oligomer as defined herein can be administered to a subject, preferably human subject, in the need thereof, in a combination regimen, using one or more further anti-fibrotic, anti-angiogenic and/or anti-tumorigenic protein(s), compound(s) or agent(s). Combinations of medications are often more effective against the diseases defined herein than a single medication used alone. To provide an example, the protein oligomer as defined herein can be used in combination with angiostatin or an angiostatin fusion protein, such as angiostatin linked to an Fc domain of an immunoglobulin, or together with inhibitors of other pathways associated with the fibrosis process, including, for example, inhibitors of TGF-beta, PDGF, VEGF, mTOR, CTGF, integrins, matrix-metalloproteinases, anti-inflammatory agents such as steroids inhibitors of cyclooxygenase, IKK/NFkB. JAK/STAT, and/or Pi3K signaling.

The present invention further relates to a protein oligomer comprising at least two, and preferably three heterodimeric human NC-1-Fc proteins for use in treating, ameliorating or preventing an angiogenesis-related disease, wherein the heterodimeric human NC-1-Fc protein comprises (i) a fusion protein comprising, from N- to C-terminus, human NC-1 from collagen 18 fused to human IgG1 Fc comprising "knob" mutations S354C/T366W, or human IgG1 Fc comprising "knob" mutations S354C/T366W fused to human NC-1 from collagen 18 and (ii) the human IgG1 Fc the "hole" mutations Y349C/T366S/L368A/Y407V.

Preferably, the human IgG1 Fc with the "knob" mutations S354C/T366W comprises SEQ ID NO: 25, and the human IgG1 Fc with "hole" mutations Y349C/T366S/L368A/Y407V comprises SEQ ID NO: 26.

More preferably, the fusion protein (i) comprising, from N- to C-terminus, human NC-1 from collagen 18 fused to human IgG1 Fc with "knob" mutations comprises or consists of SEQ ID NO: 27, 29, or 31, and the human IgG1 Fc with "hole" mutations of (ii) comprises or consists of SEQ ID NO: 28, 30, or 32.

Particularly preferred, the fusion protein (i) comprising, from N- to C-terminus, human NC-1 from collagen 18 fused to human IgG1 Fc with "knob" mutations comprises or consists of SEQ ID NO: 31, and the human IgG1 Fc with "hole" mutations of (ii) comprises or consists of SEQ ID NO: 32 (see FIG. 9 and Table 1, Molecule #1).

Such a protein oligomer has been found to be particularly useful as a pharmaceutical composition for treating, ameliorating or preventing an angiogenesis-related disease, as demonstrated in the following Examples and FIGS. 7 and 8.

A "pharmaceutical composition" as used herein can be used for non-human or, preferably, human therapy of diseases referred to herein, in a therapeutically effective dose. The "subject" as referred to herein is preferably a human suffering from a disease referred to herein.

The protein oligomer comprising at least two heterodimeric human NC-1-Fc proteins as defined herein, the monomeric human NC-1-Fc protein of the invention, or the protein oligomer comprising at least two monomeric human NC-1-Fc proteins of the invention, is the active ingredient of the pharmaceutical composition or medicament (both terms are used interchangeably), and is in one aspect, administered in conventional dosage forms prepared by combining the drug with standard pharmaceutical carriers according to conventional procedures. These procedures may involve mixing, granulating, and compressing, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables.

The carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatine, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pennsylvania.

The diluent(s) is/are selected so as not to affect the biological activity of the pharmaceutical composition. Said biological activity has been defined elsewhere herein. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like.

The protein oligomer comprising at least two heterodimeric human NC-1-Fc proteins as defined herein, the monomeric human NC-1-Fc protein of the invention, or the protein oligomer comprising at least two monomeric human NC-1-Fc proteins of the invention, is preferably formulated as a pharmaceutical composition which can be administered by standard routes. Generally, the pharmaceutical composition may be administered by the topical, transdermal, intraperitoneal, intracranial/intrathecal, intravitreal, intracerebroventricular, intracerebral, intravaginal, intrauterine, oral, rectal or parenteral (e.g. intravenous, intraspinal, subcutaneous or intramuscular) route.

Preferably, the protein oligomer comprising at least two heterodimeric human NC-1-Fc proteins as defined herein, the monomeric human NC-1-Fc protein of the invention, or the protein oligomer comprising at least two monomeric human NC-1-Fc proteins of the invention, is administered intravenously, subcutaneously, intracranial/intrathecal, intravitreal, or intraperitoneally.

A therapeutically effective dose refers to an amount of the protein oligomer comprising at least two heterodimeric human NC-1-Fc proteins as defined herein, the monomeric human NC-1-Fc protein of the invention, or the protein oligomer comprising at least two monomeric human NC-1-Fc proteins of the invention, to be used in a pharmaceutical composition which prevents, ameliorates or treats the symptoms accompanying the disease referred to in this specification. Therapeutic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

Preferably, the protein oligomer comprising at least two heterodimeric human NC-1-Fc proteins as defined herein, the monomeric human NC-1-Fc protein of the invention, or the protein oligomer comprising at least two monomeric human NC-1-Fc proteins of the invention, is administered in a concentration from about 1 to 100 mg/kg body weight. More preferably, the concentration is from about 5 to 75 mg/kg or from about 10-50 mg/kg, most preferably about 15 mg/kg body weight.

The medicament or pharmaceutical composition referred to herein is administered at least once in order to treat or ameliorate or prevent the disease recited in this specification. However, the said medicament may be administered more than one time, e.g., two, three, four, five, six times or even more frequently. For example, the medicament or pharmaceutical composition referred to herein can be administered once daily, or every second, third, fourth, fifth or sixth day, or weekly. It can also be administered every second or every third or every fourth week.

Preferred is a target plasma concentration of about 5 to 100, 10 to 50, or 15 microgram/ml blood.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent. The resulting formulations are to be adapted to the mode of administration. Dosage recommendations shall be indicated in the prescribers or users instructions in order to anticipate dose adjustments depending on the considered recipient.

The pharmaceutical composition may in a further aspect of the invention comprise drugs in addition to the protein oligomer comprising at least two heterodimeric human NC-1-Fc proteins as defined herein, the monomeric human NC-1-Fc protein of the invention, or the protein oligomer comprising at least two monomeric human NC-1-Fc proteins of the invention, which are added to the medicament during its formulation. For example, it can be used together with angiostatin, in a combination regimen. Further, combinations with recently approved modulators of fibrosis such as VEGF/PDFG RTKi (e.g. Nindetanib), specific and non-specific inhibitors of TGF-beta-signaling (Perfinidone) and modulators of integrin signaling (cilengitide, or anti alphaV abituzumab) or inflammation (leukocyte infiltration, cytokine inhibitors, antibodies against subpopulations) are envisaged, in another aspect. Thus, in preferred embodiments of the protein oligomer comprising at least two heterodimeric human NC-1-Fc proteins as defined herein, the monomeric human NC-1-Fc protein of the invention, or the protein oligomer comprising at least two monomeric human NC-1-Fc proteins of the invention, said protein oligomer or monomeric human NC-1-Fc protein further comprises angiostatin (U.S. Pat. No. 8,206,718). In specific embodiments, the angiostatin is an Fc-angiostatin or angiostatin-Fc fusion protein, preferably human fusion protein.

It is to be understood that the formulation of a pharmaceutical composition takes place under GMP standardized conditions or the like in order to ensure quality, pharmaceutical security, and effectiveness of the medicament.

The term "treatment" as used herein denotes the improvement or even elimination of one or more symptoms associated with the disease as referred to herein, by the administration of a protein oligomer or fusion protein as defined herein to a subject in the need thereof.

The term "amelioration" as referred to herein means the act of making better or improving the disease as referred to herein in the subject, by administering the protein oligomer or fusion protein as specified herein. An improvement may also be seen as a slowing or stopping of the progression of the disease.

The term "prevention" as utilized herein means the avoidance of the occurrence or re-occurrence of the disease referred to herein, by the administration of a protein oligomer or fusion protein as defined herein.

The angiogenesis-related disease is preferably selected from the group consisting of angiogenesis-dependent cancer including solid tumors, melanomas, tumor metastases, blood born tumors such as leukemias, benign tumors such as hemangiomas, acoustic neuromas, neurofibromas, trachomas, pyogenic granulomas; rheumatoid arthritis; psoriasis; ocular angiogenic diseases such as diabetic retinopathy, retinopathy of prematurity, macular degeneration, corneal graft rejection, neovascular glaucoma, retrolental fibroplasias, rubeosis; Osler-Webber syndrome; myocardial angiogenesis; plaque neovascularization; telangiectasia; hemophiliac joints; angiofibroma; wound granulation; diseases of excessive or abnormal stimulation of endothelial cells such as intestinal adhesions, atherosclerosis, scleroderma, hypertrophic scars (keloids); diseases that have angiogenesis as a pathologic consequence such as cat scratch disease (Rochele minalia quintosa) and ulcers (*Helicobacter pylori*).

Angiogenesis-related diseases are described and characterized in WO 2013/026913. The definitions and embodiments of WO 2013/026913 apply mutatis mutandis to the present application. Diseases described in WO 2017/093569 which are—or may be considered as—angiogenesis-related diseases are explicitly excluded and disclaimed from the scope of the medical use of the present invention in which a protein oligomer comprising at least two heterodimeric human NC-1-Fc proteins as defined herein is used for treating, ameliorating or preventing an angiogenesis-related disease as defined herein.

The present invention also relates to a monomeric NC-1-Fc protein, comprising human NC-1 from collagen 18 and a Fc domain from human IgG1, wherein the Fc domain from human IgG1 comprises at least one monomeric mutation, and one or more half-life extension mutations. For example, the monomeric mutation can be F405R, and the half-life extension mutations can be M252Y, S254T and/or T256E.

Preferably, the invention relates to a monomeric NC-1-Fc protein, comprising, from N- to C-terminus, human NC-1 from collagen 18 and a Fc domain from human IgG1, or a Fc domain from human IgG1 and human NC-1 from collagen 18, wherein the Fc domain from human IgG1 comprises the monomeric mutation F405R, and the half-life extension mutations M252Y, S254T and T256E. More preferably, the monomeric NC-1-Fc protein comprises or consists of SEQ ID NO: 37 (see FIG. 10, Table 4, Molecule #4).

In another embodiment, the monomeric NC-1-Fc protein comprises human NC-1 from collagen 18 and a Fc domain from human IgG4, wherein the Fc domain from human IgG4 comprises at least one monomeric mutation, and one or more half-life extension mutations.

The present invention further provides for a protein oligomer comprising at least two monomeric human NC-1-Fc fusion proteins comprising human NC-1 from collagen 18 and a Fc domain from human IgG1 or human IgG4, wherein the Fc domain from human IgG1 or IgG4 comprises at least one monomeric mutation, and one or more half-life extension mutation(s).

Preferably the monomeric mutation in human IgG1 Fc is F405R, and the half-life extension mutations are M252Y, S254T and T256E.

In addition, the present invention provides for a protein oligomer produced by a method for producing a protein oligomer comprising at least two monomeric human NC-1-Fc proteins, wherein the method comprises:
  a) culturing a host cell expressing a fusion protein comprising, from N- to C-terminus, human NC-1 from collagen 18 fused to human IgG1 Fc, or a Fc domain from human IgG1 and human NC-1 from collagen 18, wherein the human IgG1 Fc comprises at least one monomeric mutation, preferably the monomeric mutation F405R, and one or more half-life extension mutations, preferably the half-life extension mutations M252Y, S254T and T256E, under conditions which allow the formation of a protein oligomer comprising at least two, and preferably three monomeric human NC-1-Fc proteins, and b) obtaining from the host cell of step a) the protein oligomer comprising at least two, and preferably three monomeric human NC-1-Fc proteins.

Preferably, the protein oligomer comprising at least two monomeric human NC-1-Fc fusion proteins binds to fibronectin, VEGF, MMP-2 and/or MMP-9, more preferably to each of these proteins.

Preferably, the Fc domains included in the protein oligomer comprising at least two monomeric human NC-1-Fc fusion proteins are capable of inducing antibody-dependent cell-mediated cytotoxicity (ADCC).

The invention also pertains to a protein oligomer comprising at least two monomeric NC-1-Fc proteins, wherein the monomeric NC-1-Fc protein comprises, from N- to C-terminus, human NC-1 from collagen 18 and a Fc domain from human IgG1, or a Fc domain from human IgG1 and human NC-1 from collagen 18, wherein the Fc domain from human IgG1 comprises at least one monomeric mutation, and one or more half-life extension mutations, for use as a medicament.

Such a protein oligomer comprising three monomeric NC-1-Fc proteins of the invention has been found to be impressively useful as a pharmaceutical composition for treating, ameliorating or preventing fibrosis in a lung fibrosis model, as demonstrated in the following Examples and FIG. 16 (see NC-1-Fc(mono)).

It further relates to a protein oligomer comprising at least two monomeric NC-1-Fc proteins, wherein the monomeric NC-1-Fc protein comprises, from N- to C-terminus, human NC-1 from collagen 18 and a Fc domain from human IgG4, or a Fc domain from human IgG4 and human NC-1 from collagen 18, wherein the Fc domain from human IgG4 comprises at least one monomeric mutation, and one or more half-life extension mutations, for use as a medicament.

Preferably, the protein oligomer comprises at least two monomeric human NC-1-Fc fusion proteins comprising, from N- to C-terminus, human NC-1 from collagen 18 and a Fc domain from human IgG1, or a Fc domain from human IgG1 and human NC-1 from collagen 18, wherein the Fc domain from human IgG1 comprises the monomeric mutation F405R, and the half-life extension mutations M252Y, S254T and T256E.

In addition, the invention relates to a protein oligomer produced by the method of the invention for producing a protein oligomer comprising at least two monomeric human NC-1-Fc proteins, for use as a medicament.

Preferably, the medicament is for treating, ameliorating or preventing a disease selected from the group consisting of:

(i) an angiogenesis-related disease comprising angiogenesis-dependent cancer including solid tumors, melanomas, tumor metastases, blood born tumors such as leukemias, benign tumors such as hemangiomas, acoustic neuromas, neurofibromas, trachomas, pyogenic granulomas; rheumatoid arthritis; psoriasis; ocular angiogenic diseases such as diabetic retinopathy, retinopathy of prematurity, macular degeneration, corneal graft rejection, neovascular glaucoma, retrolental fibroplasias, rubeosis; Osler-Webber syndrome; myocardial angiogenesis; plaque neovascularization; telangiectasia; hemophiliac joints; angiofibroma; wound granulation; diseases of excessive or abnormal stimulation of endothelial cells such as intestinal adhesions, atherosclerosis, scleroderma, hypertrophic scars (keloids); diseases that have angiogenesis as a pathologic consequence such as cat scratch disease (Rochele minalia quintosa) and ulcers (*Helicobacter pylori*);

(ii) fibrosis or a fibrosis-associated disease, comprising fibrosis of the skin, preferably scleroderma; keloid or keloid scar; hypertrophic scar; morphea; fibrosis as a result of graft-versus-host disease; subepithelial fibrosis; endomyocardial fibrosis; uterine fibrosis; myelofibrosis; retroperitoneal fibrosis; nephrogenic systemic fibrosis; scarring after surgery; asthma; cirrhosis/liver fibrosis; fibrosis as a result of aberrant wound healing; glomerulonephritis; multifocal fibrosclerosis; radiation-induced fibrosis, preferably radiation-induced pneumonitis or radiation-induced lung fibrosis; chemotherapy-induced or drug-induced fibrosis, e.g., as a result of mTOR or EGFR kinase inhibition; usual or idiopathic pulmonary fibrosis; fibrosis as the result of autoimmune diseases, e.g., Lupus, intra-tumoral- and cancer-associated fibrosis/fibrogenesis, organ fibrosis-followed chronic inflammation, e.g., via viral stimulus or transplantation; organ fibrosis as the endstage of chronic kidney diseases, long term dialysis, or diabetes mellitus;

(iii) a vascular endothelial growth factor (VEGF)-related disease comprising a benign pathophysiological conditions depending on deregulation of the VEGF levels such as wet macular degeneration, endometriosis, bronchial asthma and diabetes mellitus, enhanced VEGF-induced vascular permeability (e.g. enhanced permeability after irradiation of brain tissue, "radionecrosis"), alterations of vaso-tonus (e.g. hypertension), rheumatoid arthritis, as well as malignant VEGF-dependent diseases such as renal cell cancer and other VEGF-addicted tumors, VEGF-dependent development of ascites, VEGF-dependent suppression of immune system, e.g. recruitment and microenvironmental education of bone marrow-derived cells (BMDC), myeloid derived suppressor cells (MdSC), or immature dendritic cells; and (iv) a matrix metalloproteinase (MMP)-related disease comprising a benign and malignant disease where MMP activation contributes to the pathophysiology, e.g., activation of MMPs during the process of local tumor invasion and cancer metastasis inherently evident in tumors with high local therapy failure rates such as glioblastoma, pancreatic cancer, lung cancer, as well as acquired enhanced MMP activation as the function of therapy induced selection pressures (e.g. tumor hypoxia and fibrosis post radiotherapy), overt immune reaction in autoimmune diseases and chronic inflammatory diseases.

The definitions, embodiments and explanations with respect to therapeutic uses of the invention of the protein oligomer comprising at least two heterodimeric NC-1-Fc fusion proteins, apply mutatis mutandis to the protein oligomer comprising at least two monomeric NC-1-Fc fusion proteins of the invention.

In a preferred embodiment, the protein oligomer comprising at least two heterodimeric human NC-1-Fc proteins, or the protein oligomer comprising at least two monomeric human NC-1-Fc fusion proteins, is administered intravenously, intracranial/intrathecal, intravitreal, subcutaneously or intraperitoneally, preferably at a concentration of 0.1-1 mg/kg/day.

In another preferred embodiment, the protein oligomer comprising at least two heterodimeric human NC-1-Fc proteins, or the protein oligomer comprising at least two monomeric human NC-1-Fc fusion proteins, has one or more biological activities selected from the group consisting of: anti-fibrotic activity, anti-angiogenic activity, anti-invasive/ anti-metastatic activity, reducing vascular permeability activity, anti-inflammatory and anti-tumorigenic activity and capability of inducing antibody-dependent cell-mediated cytotoxicity (ADCC).

In still another embodiment, the protein oligomer comprising at least two heterodimeric human NC-1-Fc proteins, or the protein oligomer comprising at least two monomeric human NC-1-Fc fusion proteins, further comprises angiostatin, thrombospondin, anti-PD-1/PD-L1 antibodies or another therapy employed for treating, ameliorating or preventing of an angiogenesis-related disease, fibrosis or fibrosis-associated disease, VEGF-related disease or MMP-related disease, as defined herein.

Medicaments for the therapy of a vascular endothelial growth factor (VEGF)-related disease which can be used in addition to the protein oligomer comprising at least two monomeric human NC-1-Fc proteins include, for example, other modulators of vascular permeability (e.g. enhanced permeability after irradiation of brain tissue, "radionecrosis") and vaso-tonus (e.g. endothelin antagonists macitentan, AT1/ACE inhibitors), ß2-sympathomimetics and corticoids in asthma, immune-suppressants in chronic inflammatory/ auto-immune diseases, chemotherapy and radiotherapy for different VEGF dependent tumors and ascites, kinase inhibitors used e.g. in renal cell cancer (mTORi e.g., RAD001, multikinase inhibitors pazopanib/suitinib/axitinib, immune modulators e.g. checkpoint inhibitors anti PD-1/PD-11). Medicaments for the therapy of a matrix metalloproteinase-related disease which can be used in addition to the protein oligomer comprising at least two monomeric human NC-1-Fc proteins include, for example, locally invasive tumors with high loco-regional therapy failure rates treated with radio-(chemo)-therapy such as glioblastoma, pancreatic cancer, anti-inflammatory and immunosuppressive therapy (anti-TNF alpha antibodies/infliximab, mycophenolic acid, cyclophosphamide etc.), tumor invasion or pseudoprogression after cancer treatment e.g. anti-angiogenic therapy in recurrent glioma, treatments of metastatic diseases with high MMP-2/MMP-9 activity such as breast cancer (i.e. hormonal therapy tamoxifen, Trastuzumab in HER2+disease, chemotherapies).

The invention further describes a polynucleotide encoding a heterodimeric human NC-1-Fc protein or a monomeric human NC-1-Fc protein.

The term "polynucleotide" or "nucleic acid" as used herein refers to single- or double-stranded DNA molecules as well as to RNA molecules. Encompassed by the said term is genomic DNA, cDNA, hnRNA, mRNA as well as all naturally occurring or artificially modified derivatives of such molecular species. The polynucleotide may be in an aspect a linear or circular molecule. Moreover, in addition to the nucleic acid sequence encoding the heterodimeric human NC-1-Fc protein or monomeric human NC-1-Fc protein, a polynucleotide may comprise additional sequences required for proper transcription and/or translation such as 5"- or 3"-UTR sequences. In light of the degeneracy of the genetic code, optimized codons may be used in the nucleic acid sequences encoding the heterodimeric human NC-1-Fc protein or monomeric human NC-1-Fc proteins. Thereby, optimal expression in, e.g., a host cell can be achieved.

It will be understood that the present invention also encompasses variants of such specific amino acid sequences of the heterodimeric human NC-1-Fc protein or monomeric human NC-1-Fc protein or nucleic acid sequences encoding them as long as these variant sequences also allow for the formation of a protein oligomer. Protein oligomers formed by said variants have preferably at least one, preferably at least two, more preferably at least three, particularly preferred all of the following biological activities: anti-fibrotic activity, anti-angiogenic activity, anti-invasive/anti-metastatic activity, reducing vascular permeability activity, anti-inflammatory and/or anti-tumorigenic activity. Further, protein oligomers formed by said variants have preferably the capability of inducing antibody-dependent cell-mediated cytotoxicity (ADCC).

In an aspect, a sequence variant as used herein differs from the specific amino acid sequence or a specific nucleic acid sequence as specified before by one, two, three, four, five or more amino acid or nucleotide substitutions, additions and/or deletions. In another aspect, the said variant sequence is at least 50%, at least 60%, at least 70%, at least 80%, at least 85%, at least 90%, at least 91%, at least 92%, at least 93%, at least 94%, at least 95%, at least 96%, at least 97%, at least 98% or at least 99% identical to the specific nucleic acid sequence or amino acid sequence of the respective two chains of the heterodimeric human NC-1-Fc protein or monomeric human NC-1-Fc protein over the entire length or over at least a stretch of half of the length of the specific sequence. It is preferred that the said variant sequence is at least 50%, at least 60%, at least 70%, at least 80%, at least 85%, at least 90%, at least 91%, at least 92%, at least 93%, at least 94%, at least 95%, at least 96%, at least 97%, at least 98% or at least 99% identical to the sequences depicted in SEQ ID NO: 27, 28, 29, 30, 31, 32 or 37 over the entire length. The term "identical" as used herein refers to sequence identity characterized by determining the number of identical amino acids between sequences wherein the sequences are aligned so that the highest order match is obtained. It can be calculated using published techniques or methods codified in computer programs such as, for example, BLASTP or FASTA (Altschul 1990, *J Mol Biol* 215, 403). The percent identity values are, in one aspect, calculated over the entire amino acid sequence or over a sequence stretch of at least 50% of the query sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, *CABIOS* 5, 151) or the programs Gap and BestFit (Needleman 1970, *J Mol Biol* 48; 443; Smith 1981, *Adv Appl Math* 2, 482), which are part of the GCG software packet (Genetics Computer Group 1991, 575 Science Drive, Madison, Wisconsin, USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

The invention further describes a vector comprising the polynucleotide encoding the heterodimeric human NC-1-Fc protein or monomeric human NC-1-Fc protein.

Preferably, the vector is an expression vector.

The term "vector" encompasses preferably phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, in an aspect, comprise DNA of sufficient length for either homologous or heterologous recombination as described in detail below. The vector encompassing the mentioned polynucleotide, in an aspect, further comprises selectable markers for propagation and/or selection in a host cell. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells.

Moreover, in an aspect, the above-indicated polynucleotide is operatively linked to expression control sequences allowing expression in prokaryotic or eukaryotic host cells or isolated fractions thereof in the said vector. Thus, in an aspect, the vector is an expression vector. Expression of the polynucleotide comprises transcription of the polynucleotide into a translatable mRNA. Regulatory elements ensuring expression in host cells are well known in the art. In an aspect, they comprise regulatory sequences ensuring initiation of transcription and/or poly-A signals ensuring termination of transcription and stabilization of the transcript. Additional regulatory elements may include transcriptional as well as translational enhancers. Possible regulatory elements permitting expression in prokaryotic host cells comprise, e.g., the lac-, trp- or tac-promoter in *E. coli*, and examples for regulatory elements permitting expression in eukaryotic host cells are the AOX1- or the GAL1-promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotide or vector into a targeted cell population. Methods which are well known to those skilled in the art can be used to construct recombinant viral vectors; see, for example, the techniques described in Sambrook, Molecular Cloning A Laboratory Manual, Cold Spring Harbor Laboratory (2001) N.Y. and Ausubel, Current Protocols in Molecular Biology, Green Publishing Associates and Wiley Interscience, N.Y. (1994).

The invention further describes a host cell comprising the polynucleotide encoding the heterodimeric human NC-1-Fc protein or monomeric human NC-1-Fc protein.

The term "host cell" as used herein as used herein encompasses prokaryotic and eukaryotic host cells. In an aspect the host cell is a bacterial cell. In one aspect, the said bacterial host cell is an *E. coli* host cell. Such a bacterial host cell may be used, e.g., for reproduction of the mentioned polynucleotide or vector.

A eukaryotic host cell, in an aspect, is a cell which comprises the polynucleotide encoding the heterodimeric human NC-1-Fc protein or monomeric human NC-1-Fc protein, or the vector wherein said polynucleotide or vector are expressed in the host cell in order to generate a protein oligomer comprising the heterodimeric human NC-1-Fc protein or monomeric human NC-1-Fc protein. The polynucleotide may be introduced into a host cell either transiently or stably. In an aspect, the eukaryotic host cell may be a cell of a eukaryotic host cell line which stably expresses the polynucleotide. In another aspect, the host cell is a eukaryotic host cell which has been transiently transfected with the polynucleotide or vector and which expresses the polynucleotide. In another aspect, the said cell is a cell which has been genetically engineered to produce the protein. How such cells can be genetically engineered by molecular biology techniques is well known to the skilled person.

Sequences

The sequences show:

SEQ ID NO: 1: murine Collagen 18
SEQ ID NO: 2: human Collagen 18
SEQ ID NO: 3: NC-1 domain of murine Collagen 18
SEQ ID NO: 4: NC-1 domain of human Collagen 18
SEQ ID NO: 5: murine Fc domain
SEQ ID NO: 6: human Fc domain
SEQ ID NO: 7: murine Superstatin
SEQ ID NO: 8: murine Fibronectin motif
SEQ ID NO: 9: murine N-terminal zinc-binding domain Endostatin
SEQ ID NO: 10: human N-terminal zinc-binding domain Endostatin
SEQ ID NO: 11: murine RGD motif
SEQ ID NO: 12: human RGD motif
SEQ ID NO: 13: human Superstatin
SEQ ID NO: 14: human Superstatin with His at positions 1 and 3 replaced by Ala
SEQ ID NO: 15: human Superstatin with Gln at position 7 replaced by Cys
SEQ ID NO: 16: human Superstatin with "RGD" motif replaced by "RAD" motif
SEQ ID NO: 17: murine integrin-binding motifs of Fibronectin
SEQ ID NO: 18: mEndostatin (murine)
SEQ ID NO: 19: hEndostatin (human)
SEQ ID NO: 20: mP1 peptide (murine; N-terminal)
SEQ ID NO: 21: E4 peptide of Endostatin (human; C-terminal)
SEQ ID NO: 22: hP1 peptide of Endostatin (human; N-terminal)
SEQ ID NO: 23: Enterokinase cleavage site
SEQ ID NO: 24: Fc sequence of wildtype human IgG1
SEQ ID NO: 25: Fc sequence "knob" human IgG1 Fc: S354C/T366W
SEQ ID NO: 26: Fc sequence "hole" human IgG1 Fc Y349C/T366S/L368A/Y407V
SEQ ID NO: 27: NC-1-enterokinase site-linker-human IgG1 Fc with "knob" mutations (S354C/T366W)
SEQ ID NO: 28: Human IgG1 Fc with "hole" mutations Y349C/T366S/L368A/Y407V
SEQ ID NO: 29: Human IgG1 Fc with "knob" mutations (S354C/T366W)-linker-enterokinase site-NC-1
SEQ ID NO: 30: Human IgG1 Fc with "hole" mutations Y349C/T366S/L368A/Y407V SEQ ID NO: 31: NC-1-Fc fusion protein with "knob" mutations S354C/T366W; chain 1 of heterodimeric NC-1-Fc (Molecule #1)

SEQ ID NO: 32: Fc with "hole" mutations Y349C/T366S/L368A/Y407V; chain 2 of heterodimeric NC-1-Fc (Molecule #1)

SEQ ID NO: 33: NC-1-Fc fusion protein with "knob" mutations S354C/T366W; chain 1 of homodimeric NC-1-Fc (Molecule #2)

SEQ ID NO: 34: Fc with "hole" mutations Y349C/T366S/L368A/Y407V; chain 2 of homodimeric NC-1-Fc (Molecule #2)

SEQ ID NO: 35: Fc-Endostatin fusion protein with "knob" mutations S354C/T366W; chain 1 of heterodimeric Fc-Endostatin (Molecule #3)

SEQ ID NO: 36: Fc-Endostatin fusion protein with "hole" mutations Y349C/T366S/L368A/Y407V; chain 2 of heterodimeric Fc-Endostatin (Molecule #3)

SEQ ID NO: 37: Monomeric NC-1-Fc, wherein Fc includes monomeric mutation F405R and YTE half life extension mutations M252Y/S254T/T256E (Molecule #4)

SEQ ID NO: 38: Monomeric Fc-Endostatin, wherein Fc includes monomeric mutation F405R and YTE half life extension mutations M252Y/S254T/T256E (Molecule #5)

FIGURES

The Figures show:

FIG. 1: SDS-PAGE (left) and Western Blot (right) analysis of mouse NC-1 and human NC-1 from cell culture supernatant.
Lane M: Marker
Lanes 1 to 3: Cell culture supernatant from day 2, 4 and 5 post-transfection under a reducing condition
Lanes 4 to 6: Cell culture supernatant from day 2, 4 and 5 post-transfection under a non-reducing condition
Lane NC1: Negative control under a reducing condition
Lane NC2: Negative control under a non-reducing condition
Primary antibody: Mouse anti-His mAb (Genscript)

FIG. 2: SDS-PAGE (left) and Western Blot (right) analysis of cell lysates of mouse NC-1 and human NC-1.
Lanes 1 to 3: Cell lysate from day 2, 4 and 5 post-transfection under a reducing condition
Lane 4: Cell debris from day 4 post-transfection under a reducing condition
Lanes 5 to 7: Cell lysate from day 2, 4 and 5 post-transfection under a non-reducing condition
Lane 8: Cell debris from day 4 post-transfection under a non-reducing condition
Lane NC1: Negative control under a reducing condition
Lane NC2: Negative control under a non-reducing condition
Primary antibody: Mouse anti-His mAb (Genscript)

FIG. 3: Transient mammalian (Expi) expression of heterodimeric NC-1-Fc using two plasmids encoding the NC-1-Fc-knob and Fc-hole led to formation of two peaks in SEC after protein A purification. The composition of each peak is shown by SDS-PAGE under reduced and non-reduced conditions. Peak one consists of two bands under reduced conditions containing the NC-1-Fc-knob at 62 kDa and Fc-hole at 30 kDa. In contrast, peak 2 consists of only a single band of Fc-hole under reduced conditions indicating that Fc-hole dimers were generated. Accordingly, peak 1 corresponds to an 88 kDa heterodimeric NC-1-Fc(KiH) protein under non-reduced conditions, whereas, the size of the Fc-hole dimer peak 2 corresponds to an about 50 kDa protein under non-reduced condition.

FIG. 4: After protein A purification of protein supernatant, a SEC-HPLC was performed to detect the size of the expressed protein under native conditions. To better estimate the size of the expressed proteins (two peaks) well-known spike in controls consisting of IgG1/2B, Albumin, human Fc and IgG1-Fab were utilized. As expected peak 2 consisting of a Fc-hole dimer runs at the same time as an Fc domain. However, Peak 1 appeared to be larger than a standard IgG (150 kDa). This is unexpected as the reduced gel in FIG. 3 clearly shows that peak 1 contains both the NC-1-Fc-knob and Fc-hole parts resulting in an 88 kDa heterodimeric NC-1-Fc protein.

Figure 5:
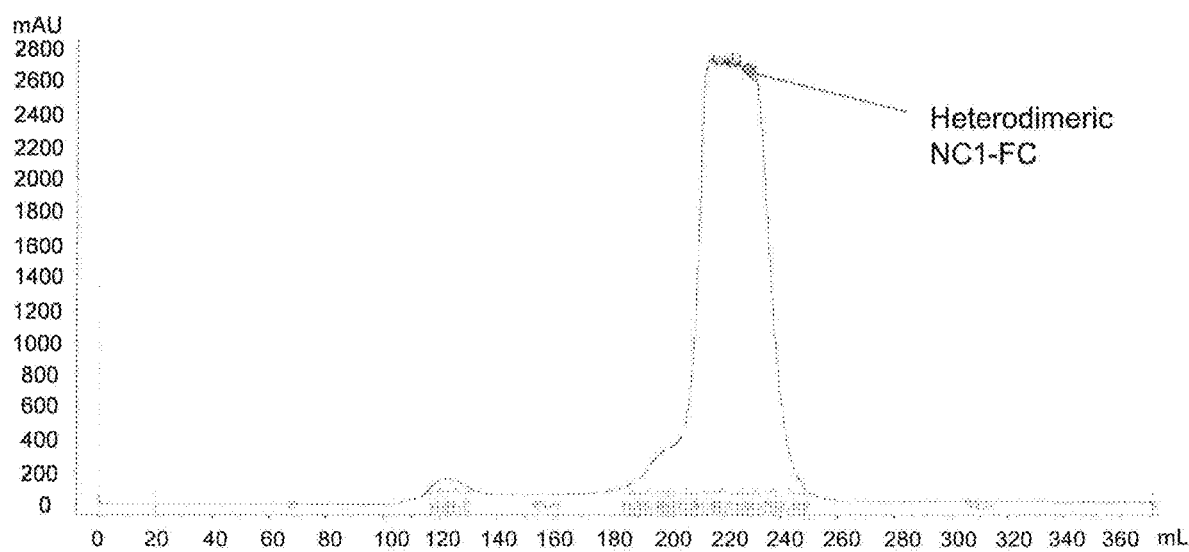

FIG. 5: Transducing mammalian cells with 2:1 ratio of NC-1-Fc-knob vs. Fc-hole plasmids enhanced formation of heterodimeric NC-1-Fc-KiH and almost diminished the formation of Fc-hole dimers.

Figure 6:
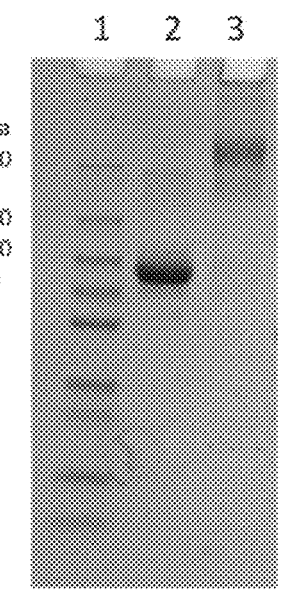

FIG. 6: Crosslinking studies finally confirmed the observation of SEC that heterodimeric NC-1-Fc must be substantially larger than 88 kDa monomeric molecule found in non-reduced gel (Band 2). Indeed, heterodimeric NC-1-Fc (KiH) forms a trimer under physiologic conditions (Band 3). Details of the crosslinking procedure are found in the description of FIG. 17.

Figure 7:
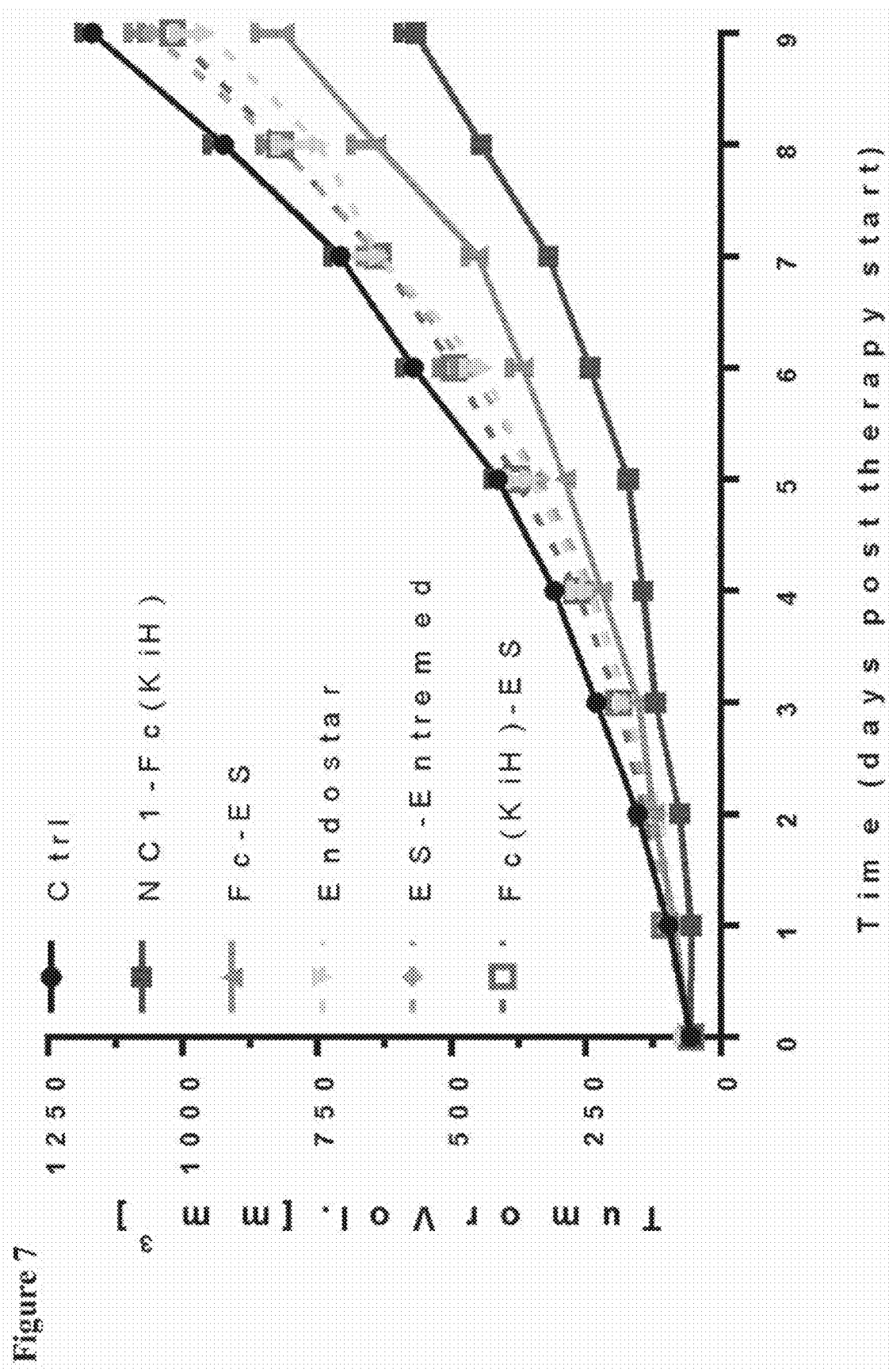

FIG. 7: Superior anticancer effects of NC-1-Fc-KiH in Lewis Lung Cancer Model. Tumor growth kinetic of syngeneic Lewis Lung Cancer (LLC) model in C57bl6 mice. The trimeric NC-1-Fc(KiH) demonstrated superior activity compared to all recombinant monomeric endostatin molecules as well as Fc-Endostatin (Fc-ES) that forms a dimer over the Fc moiety. Three monomeric endostatin compounds were utilized including, heterodimeric Fc (KiH) Endostatin (Fc-(KiH)-ES) that forms a monomeric endostatin with a dimeric Fc, i.e., the reference backbone construct for heterodimeric NC-1-Fc(KiH), Endostar, monomeric recombinant E. coli His-tag endostatin approved in China, and Entemed endostatin (ES-Entremed), monomeric recombinant P. pastoris endostatin that was in Phase I/II trials in US/Europe. All drugs were administered s.c. at endostatin equivalent dose of 20 µg/mouse/day. Bars represent mean of n:7 +/− SEM.

FIG. 8: Tumor growth inhibition. Trimeric NC-1-Fc(KiH) performed best with 51% inhibition of LLC tumor growth at day 9 post treatment start (B). This effect was significantly more pronounced compared to all monomeric endostatin molecules (p<0.001). Intriguingly, NC-1-Fc(KiH) was significantly more effective than dimeric Fc-ES (A, p<0.01). Hence, in addition to oligomerization other biological properties of the entire NC-1 sequence vs. only the N-terminal endostatin domain might be relevant for the anticancer activity of this molecule.

Figure 11:
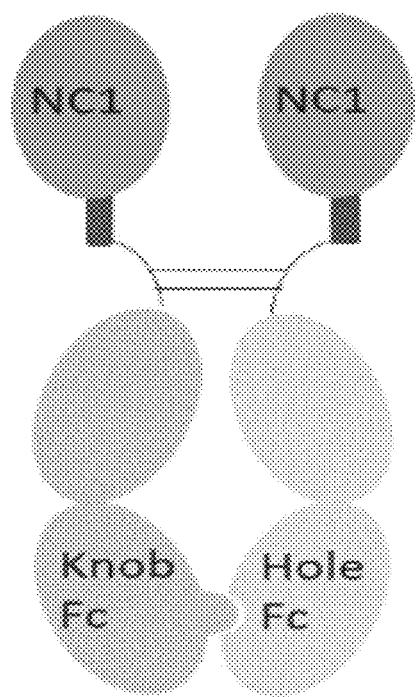
Figure 12:
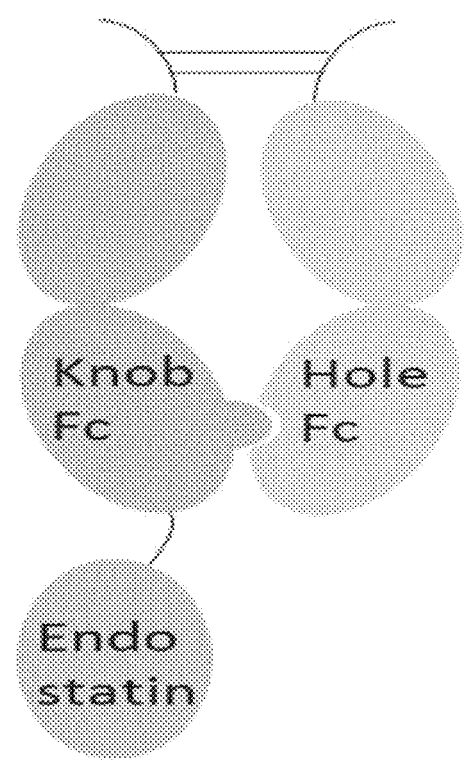
Figure 13:
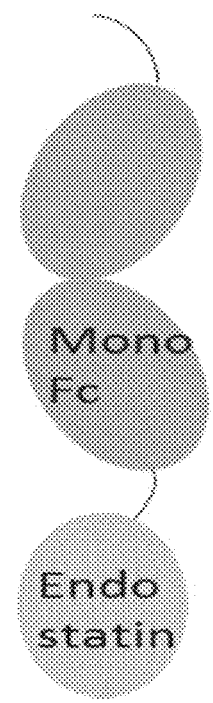
Figure 14:
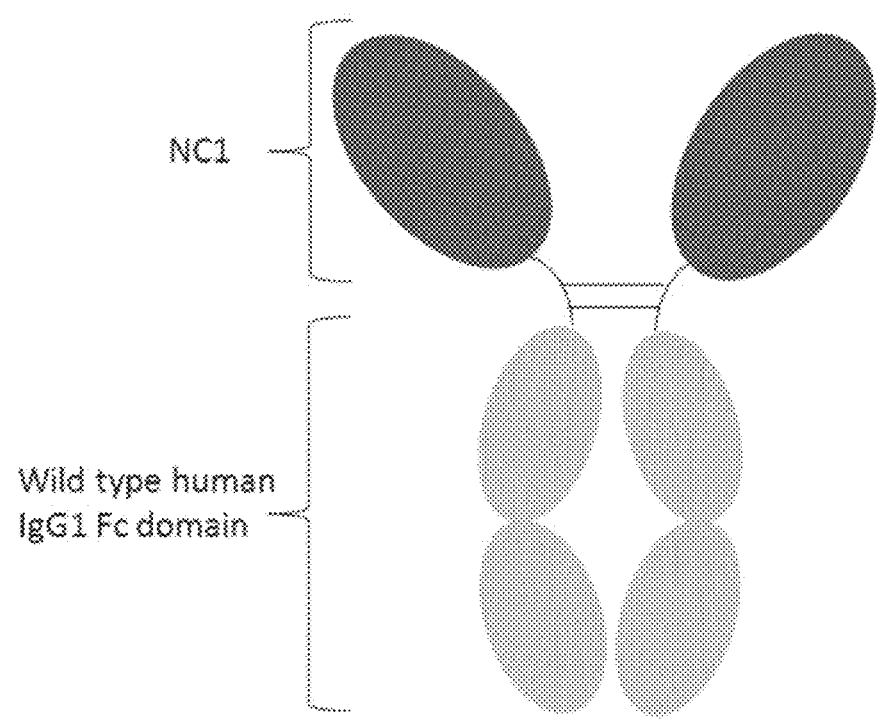

FIG. 9: Heterodimeric NC-1-Fc (Molecule #1)
FIG. 10: Monomeric NC-1-Fc (Molecule #4)
FIG. 11: Homodimeric NC-1-Fc (Molecule #2)
FIG. 12: Heterodimeric Fc-Endostatin (Molecule #3)
FIG. 13: Monomeric Fc-Endostatin (Molecule #5)
FIG. 14: N and C-terminal NC-1-Fc fusion proteins using IgG1 wild type backbone, in analogy to Fc-Endostatin (Molecule #6)
FIG. 15: (A) Heterodimeric proteins consisting of NC-1-Fc(knob) with Fc(hole) fused to different moieties including an IgG Fab fragment (Molecule #7). (B)
FIG. 16: In-vivo treatments with protein oligomers comprising monomeric NC-1-Fc (NC-1-Fc(mono)) (SEQ ID NO: 37) in a lung fibrosis model (see Example 4).

Fibrosis data n: 10 each group
IR dose: 15Gy
Monomers: Patterned structure
* P<0.05, **p<0.01
Dashed lines 16 weeks post IR (red) vs. non-irradiated (black) lines.

Figure 17:
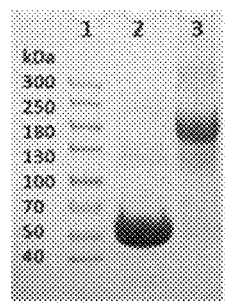

FIG. 17: NC-1-Fc-mono forms a trimer

Protein associations and 3D property are in part lost even at non-reducing conditions by gel-electrophoresis. Hence, crosslinking of native protein was required to decipher the composition of the NC-1-Fc-mono. To this end, a crosslinking protocol was utilized as described (Kuo, Javaherian et al. JCB 2001, PMID: 11257123) with modifications. Briefly, 50 tig of protein in 50 µl of PBS containing 50 µM zinc-chloride was employed. To this, 5 µl of cross-linker EGS (Ethylene Glycol-bis(succinic acid N-hydroxysuccinimide ester), which had been dissolved in DMSO at 10 mM concentration, was added. After incubating the sample at 37° C. for ½ hr, the reaction was stopped by 4 µl of 1 M Tris, pH8. Finally, the sample was subjected to SDS-PAGE under non-reduced condition. The inventors' data clearly indicate that NC-1-Fc(mono) forms a trimer over the NC-1 oligomerization domain as found after crosslinking in lane 3. These data are in line with observation of NC-1-Fc(mono) size under native conditions in SEC.

Figure 18:
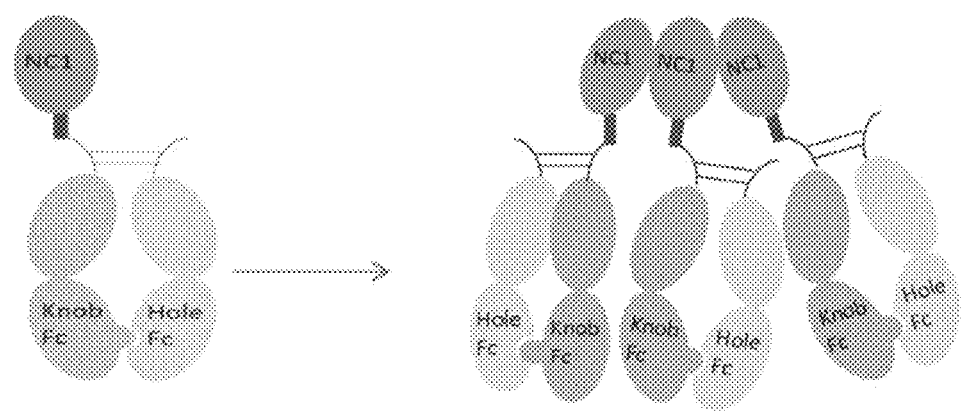

FIG. 18: Heterodimeric NC-1-Fc (Molecule #1) forms a trimer over the oligomerization domain of NC-1 as revealed by crosslinking of non-denatured protein.

Figure 19:
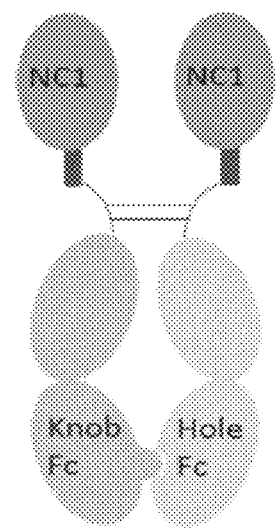

FIG. 19: Homodimeric NC-1-Fc (Molecule #2).

Figure 20:
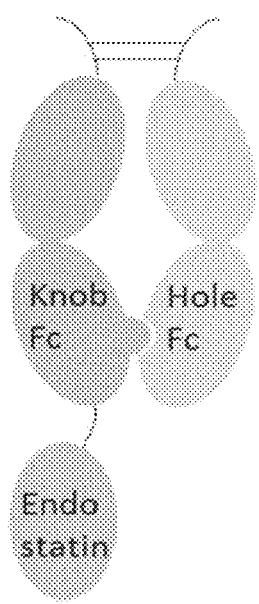

FIG. 20: Heterodimeric Fc-Endostatin (Molecule #3).

Figure 21:
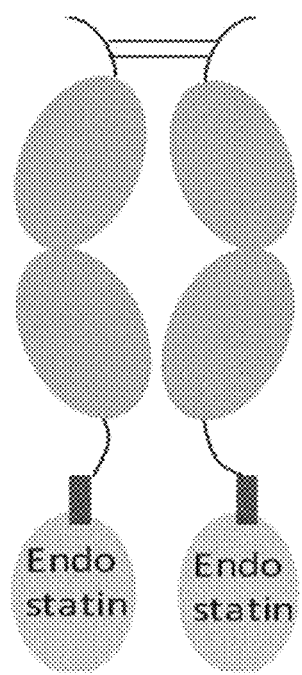

FIG. 21: Endostatin constructs conjugated via N-terminal conjugation to Fc(knob).

Figure 22:
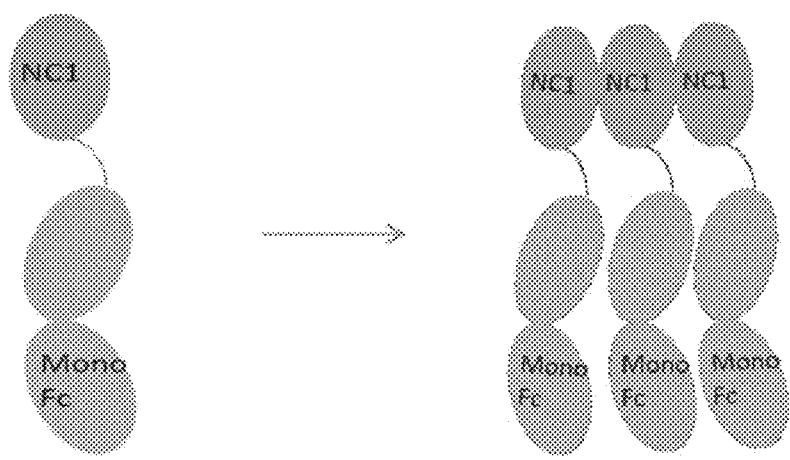

FIG. 22: Monomeric NC-1-Fc (Molecule #4) forms a trimer via NC-1 oligomerization domain.

Figure 23:
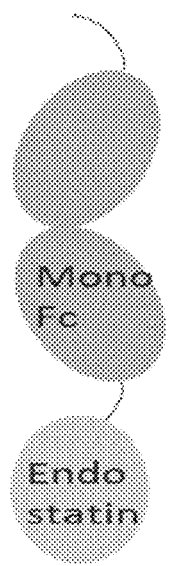

FIG. 23: Monomeric Fc-Endostatin (Molecule #5).

Figure 24:
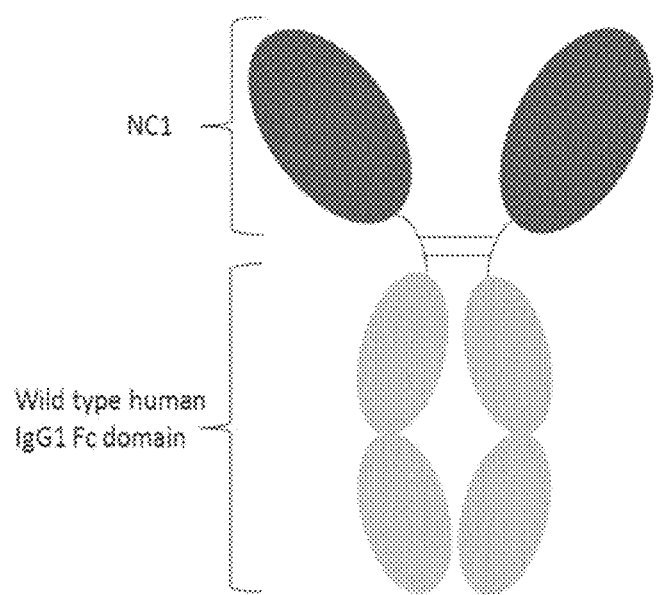

FIG. 24: N and C-terminal NC-1-Fc fusion proteins using IgG1 wild type backbone, in analogy to Fc-Endostatin (Molecule #6).

FIG. 25: (A) Heterodimeric proteins consisting of NC-1-Fc(knob) with Fc(hole) fused to different moieties including an IgG Fab fragment. (Molecule #7). (B) is a size exclusion chromatogram including Molecule #7.

TABLES
Table 1: Heterodimeric NC-1-Fc (Molecule #1)
Table 2: Homodimeric NC-1-Fc (Molecule #2)
Table 3: Heterodimeric Fc-Endostatin (Molecule #3)
Table 4: Monomeric NC-1-Fc (Molecule #4)
Table 5: Monomeric Fc-Endostatin (Molecule #5)
Table 6: Additional constructs designed but failed The invention will now be illustrated by examples which shall, however, not be construed as limiting the scope of the invention.

EXAMPLES

Example 1: Recombinant Expression of NC-1 not Feasible for Preclinical and Clinical Studies Production of Collagen 18 NC-1 was from the beginning a big challenge due to aggregation of the molecule over the oligomerization domain. Therefore, no-in-vivo data exist on the efficacy of NC-1, and only little research was conducted on this so far believed precursor molecule to endostatin.

Dr. Javaherian and few other labs were able to express very little of recombinant NC-1 by His-tag and Flag-tag, respectively, but it was never enough for a preclinical dosing of animals. Therefore, production of NC-1 amounts relevant for preclinical and clinical studies constituted a challenge. On confirmation of this postulate, data on ultra-low yield of human and mouse His-tag NC-1 expression are provided by the present inventors, in the following.

DNA sequences encoding mouse NC-1 and human NC-1 were designed and synthesized. The complete sequences, i.e. EcoRI-Kozak sequence-Leader sequence-His6 tag-Mouse NC-1-Stop codon-HindIII (SEQ ID NO. 40), and EcoRI-Kozak sequence-Leader sequence-His6 tag-Human NC-1-Stop codon—HindIII (SEQ ID NO. 42), were then subcloned into the pcDNA3.4 vector for Expi293F cell expression. Expi293F cells were grown in serum-free Expi293FTM Expression Medium (Thermo Fisher Scientific). The cells were maintained in Erlenmeyer Flasks (Corning Inc., Acton, MA) at 37° C. with 8% CO2 on an orbital shaker (VWR Scientific, Chester, PA). One day prior to transfection, the cells were seeded at an appropriate density in Corning Erlenmeyer Flasks. On the day of transfection, DNA and transfection reagent were mixed at an optimal ratio and then added into the flask with cells ready for transfection. The recombinant plasmids encoding target proteins of mouse NC-1 and human NC-1 were transiently transfected into 40 ml suspension Expi293F cell culture, respectively. The cell culture supernatants collected on day 2, 4 and day 5 were used for the protein expression evaluation. About 1 ml cell culture supernatant and cell pellet samples were collected on day 2, day 4 and day 5 post-transfection and analyzed by SDS-PAGE and Western blot analysis to evaluate the expression levels of mouse NC-1 and human NC-1 as shown in FIGS. 1 and 2. The primary antibody used for Western blots was Mouse-anti-his mAb (GenScript, Cat.No.A00186).

The present inventors have tried to express and detect mouse NC-1 and human NC-1 in suspension Expi293F cell cultures.

For mouse NC-1, a weak target band was positively detected from cell culture supernatant by Western blot analysis as shown in FIG. 1B. The target signal with estimated molecular weight of ~40 kDa (Cal.MW.38.17) was observed from cell debris by reducing condition SDS-PAGE and Western blot analysis as shown in FIGS. 2E and F (black arrow). This suggests poor secretion of the target protein. The estimated expression level of target protein is ~0.1 mg/L. This suggests poor secretion of the target protein.

For human NC-1, obvious target band with estimated molecular weight of ~40 kDa (C Cal.MW.37.47) was detected from cell culture supernatant and cell debris by SDS-PAGE and Western blot analysis under reducing condition as shown in FIGS. 1C and D and FIGS. 2G and H. The estimated expression level of target protein is low <3 mg/L. Compared to mouse NC-1, the expression of human NC-1 was better, but still at low levels for most downstream evaluations, e.g., in-vivo studies.

This data shows that recombinant expression of NC-1 was challenging and not feasible for preclinical and clinical studies.

Example 2: Engineering Collagen 18 NC-1-Fc Constructs

The major aim by the present invention was to move in the area of immunoglobulin IgG Fc conjugation with numerous biotechnological, pharmacokinetic as well as biological advantages.

However, generation of Fc-NC-1 was not a straight forward process as evident from the fact that the present inventors have spent almost a decade now to achieve systems for large scale production of NC-1 and failed with numerous constructs and classical tags.

The reason for this is that there are two oligomerization forces, one trimerization force induced by the NC-1 oligomerization domain, and a second dimerization force induced by the IgG-Fc. The present inventors have spent tremendous time with all different existing technologies, i.e., C- or N-terminal conjugation of NC-1 to Fc, like previously performed with endostatin, and all these approaches failed; see, e.g. Tables 2 and 6.

One has to consider that in classical Fc-tagging approaches, one would produce an N- or C-terminal conjugated Fc-NC-1 molecule that without the NC-1 oligomerization domain would form a dimer. However, with NC-1 oligomerization domain one receives aggregates and very pure expression.

To the present inventor's knowledge, there is no existing literature about successful NC-1-Fc conjugation.

As described below, the present inventors have studied different approaches to circumvent this main issue and after a decade of research found successful strategies. One central point was to generate monovalent NC-1-dimeric Fc, or heterodimeric NC-1-Fc. The present inventors decided to use a mutation in Fc that precludes dimerization of NC-1-Fc with NC-1-Fc, using the Fc "Knob-in-Hole" (KiH) strategy. Hence, NC-1-Fc-knob would only dimerize with empty Fc-hole. While knob-knob dimerization is prohibited, hole-hole dimerization could still occur. Indeed, the present inventors found two peaks, one being the envisioned NC-1-Fc(KiH) heterodimer and a second peak being Fc-hole-Fc-hole dimers. This indicated that NC-1-Fc-knob was more difficult for cells to be expressed. The present inventors again circumvented this problem by increasing the expression of NC-1-Fc-knob vs. Fc-hole (at the beginning ratio of 2:1, then 4:1); this leads to mainly one peak of heterodimeric NC-1-Fe-KiH with excellent expression efficacy. However, in size exclusion column the present inventors recognized that the molecule under physiologic condition is much larger than one would expect from a NC-1-Fc-KiH heterodimer. Subsequent crosslinking experiments confirmed that they have strikingly achieved to produce a trimeric molecule i.e. a trimer of NC-1-Fc-KiH heterodimer. This molecule preserves all excellent properties of Fc plus the trimeric NC-1. Strikingly, this trimeric NC-1-Fc-KiH molecule demonstrates the same efficacy in binding unique oligomeric NC-1 binding partners such as Fibronectin, VEGF, and MMP-2/-9. With excellent expression ratio, the present inventors have now after long time the possibility to perform in-vivo experiments in different model with this NC-1 molecule. In addition to the data in lung cancer (LLC) model and the lung fibrosis model, further experiments are ongoing and will tremendously improve their understanding of this molecule.

Of note, separate expression of NC-1-Fc-knob and NC-1-Fe-hole and later dimerization via redoxsystem all failed to produce an efficient NC-1-Fc construct. Hence, the steric hindrance of a heterodimeric Fc was crucial for the success and lack of aggregation. Next, the present inventors aimed to evaluate whether adding moieties to the "empty" Fc-hole will affect the molecule. To this end, they conjugated classical Fab fragment of antibody to the Fe-hole and co-expressed it with NC-1-Fc-knob. Intriguingly, addition of a steric hindrance by a Fab moiety NC-1-Fc-KiH-Fab decreased the efficiency of expression compared to NC-1-Fc-KiH heterodimer.

Together, the trimeric NC-1-Fc-KiH heterodimer (SEQ ID NO: 31/32; Table 1; FIG. 9; Molecule #1) seems to be the first NC-1 based Fc construct reported by the present inventors, and given the 3D complexities of both NC-1 and Fc engineering such a molecule was and is not a trivial process that one would be able to deduce from current literature.

Example 2A: Heterodimeric NC-1-Fc (SEQ ID NO: 31/32)

Transient mammalian (Expi) expression of heterodimeric NC-1-Fc-KiH using two plasmids encoding the NC-1-Fc-knob and Fc-hole led to formation of two peaks in SEC after protein A purification. The composition of each peak is shown by SDS-PAGE under reduced and non-reduced conditions, in FIG. 3. Peak one consists of two bands under reduced conditions containing the NC-1-Fc-knob at 62 kDa and Fc-hole at 30 kDa. In contrast, peak 2 consists of only a single band of Fc-hole under reduced conditions indicating that Fc-hole dimers were generated. Accordingly, peak 1 corresponds to an 88 kDa heterodimeric NC-1-Fc-KiH protein under non-reduced conditions, whereas, the size of the Fc-hole dimer peak 2 corresponds to an about 50 kDa protein under non-reduced condition; see FIG. 3.

The present inventors ran SEC-HPLC for these two separated peaks and compared them to other proteins with known sizes (see FIGS. 4 to 6). As expected, peak 2 runs at the same size as an Fc domain. Peak 1 appeared to be larger than a standard IgG. This is unexpected as the reduced gel in FIG. 3 clearly shows that peak 1 contains both the knob and hole parts (i.e., NC-1-Fc-knob at 62 kDa and Fc-hole at 30 kDa).

Crosslinking studies finally confirmed that the present inventors were for the first time able to generate an NC-1 trimer on top of an Fc backbone, i.e., a trimer of NC-1-Fc-KiH (or NC-1-Fc(KiH)) under physiologic conditions.

By increasing the amount of NC-1-Fc-knob vs. Fc-hole (ratio of 2:1 at the beginning, then 4:1) they were able to further optimize the production of this NC-1-Fc-KiH trimeric construct by almost eradicating the hole-hole formation (peak 2); see FIG. 5.

So far binding studies demonstrate that NC-1-Fe-Kin trimer retains central properties of NC-1 like binding to Fibronectin and also to VEGF and MMP-2/-9.

Crosslinking experiments confirmed the formation of a trimeric NC-1-Fc-KiH heterodimer under physiologic conditions; see FIG. 6.

Example 2B: Monomeric NC-1-Fc (SEQ ID NO: 37)

The present inventors further generated a monomeric NC-1-Fc (SEQ ID NO: 37; FIG. 10; Molecule #4). The IgG1 Fc includes the monomeric mutation F405R, and the YTE half life extension mutations M252Y/S254T/T256E. High yields of monomeric NC-1-Fc (also named NC-1-Fc(mono) herein) could be obtained upon expression. NC-1-Fc(mono) forms a trimer over the NC-1 oligomerization domain as found after crosslinking in lane 3 of FIG. 17; see also Example 5. Protein oligomers comprising monomeric NC-1-Fc (NC-1-Fc(mono)) (SEQ ID NO: 37) show superior antifibrotic activity in a lung fibrosis model, as demonstrated in Example 4.

Example 3: Anticancer Effects by Collagen 18 NC-1-Fc Constructs

As a tumor model, Lewis Lung Cancer (LLC) s.c. syngeneic models on C57b16 mouse background have been used. The mice have been treated with equivalent doses of:

Heterodimeric NC-1-Fc (KiH) that forms a trimer over the NC-1 oligomerization domain (NC-1-Fc(KiH)) (SEQ ID NO: 31/32), Heterodimeric Fc (KiH) Endostatin (Fc-(KiH)-ES) (SEQ ID NO: 35/36), that forms a monomeric endostatin with a dimeric Fc, i.e., the reference construct for heterodimeric NC-1-Fc(KiH)

Fc-Endostatin (Fc-ES) that forms a dimer over the Fc moiety,

Endostar, monomeric recombinant *E. coli* His-tag endostatin approved in China,

Entemed endostatin (ES-Entremed), monomeric recombinant *P. pastoris* endostatin that was in Phase I/II trials in US/Europe.

The tumor growth delay data clearly show the superior activity of NC-1 based drug design, the trimeric NC-1-Fc (KiH) over all other construct in tumor growth inhibition in the prototypic LLC model in a direct back-to-back comparison; see FIG. 7.

Of note, the superior activity of trimeric NC-1-Fc(KiH) with 51% inhibition of tumor growth at day 9 post treatment start versus 30% inhibition with dimeric Fc-ES (p<0.01) clearly indicate that not only oligomerization (trimer vs. dimer) but also other biological properties of the entire NC-1 sequence vs. only the N-terminal endostatin domain contribute to the therapeutic effect of the trimeric NC-1-Fc (KiH); see FIG. 8.

Example 4: Antifibrotic Effects by Collagen 18 NC-1-Fc Constructs

In-vivo treatments with protein oligomers comprising monomeric NC-1-Fc (NC-1-Fc(mono)) (SEQ ID NO: 37) have been generated in a lung fibrosis model, the results of which are shown in FIG. 16.

The present inventors have previously shown that the N-terminus of Endostatin and oligomerization demonstrated by NC-1 mimicking (oligomeric Fc-Endostatin, FcES) are crucial in preventing the development of pulmonary fibrosis induced by ionizing radiation (IR; WO 2017/093569). The present inventors aimed to discover the potential of the novel protein oligomer comprising recombinant monomeric NC-1-Fc (NC-1-Fc(mono)) (SEQ ID NO: 37) to inhibit and eventually reverse fibrosis in a back-to-back comparison with FcEs and three monomeric endostatin constructs, i.e. Entremed Endostatin, Endostar and Fc(mono)-ES. C57bl6 radiation induced lung fibrosis (RILF) Model was used. Treatment started 16 Weeks after 15Gy whole thoracic irradiation where the average lung density was increased from −380 hounsfield units (HU, black dashed line) in control mice, to −320 HU (red dashed line) in irradiated lungs (FIG. 16A). All compounds were administered daily s.c. for a duration of 8 weeks at equimolar dose. Both oligomeric construct FcES and NC-1-Fc(mono) showed antifibrotic effects by reducing lung density (FIG. 16B), increasing lung volume (FIG. 16C) and improving the quantitative CT based lung fibrosis index (FIG. 16D) (FI, Zhou et al. 2017, 16; Pubmed document 29116014).

Intriguingly, the novel protein oligomer comprising recombinant monomeric NC-1-Fc (NC-1-Fc(mono)) (SEQ ID NO: 37) was the only compound that was able to reverse fibrosis in this intervention trial. The antifibrotic effects of said protein oligomer of the invention was significantly stronger vs. FcES (p<0.01). All three monomeric constructs are shown as patterned bars. Bars represent mean of n:10 +/− SEM.

Example 5: NC-1-Fc(Mono) (SEQ ID NO. 37) Forms a Trimer

Protein associations and 3D property are in part lost even at non-reducing conditions by gel-electrophoresis. Hence, crosslinking of native protein was required to decipher the composition of the NC-1-Fc(mono). To this end, a cross-linking protocol was utilized as described (Kuo, Javaherian et al. JCB 2001, PMID: 11257123) with modifications. Briefly, 50 µg of protein in 50 µl of PBS containing 50 µM zinc-chloride was employed. To this, 5 µl of cross-linker EGS (Ethylene Glycol-bis(succinic acid N-hydroxysuccinimide ester), which had been dissolved in DMSO at 10 mM concentration, was added. After incubating the sample at 37° C. for ½ hr, the reaction was stopped by 4 µl of 1 M Tris, pH8. Finally, the sample was subjected to SDS-PAGE under non-reduced condition. The inventors' data clearly indicate that NC-1-Fc(mono) forms a trimer over the NC-1 oligomerization domain as found after crosslinking in lane 3 of FIG. 17. These data are in line with observation of NC-1-Fc (mono) size under native conditions in SEC.

TABLE 1

| | Heterodimeric NC-1-Fc |
|---|---|
| Molecule # | 1 |
| Name | Heterodimeric NC-1-Fc<br>Alias NC-1-Fc(KiH) |
| Chain 1<br>(NC-1-Fc<br>with<br>knob<br>mutations:<br>Pr00129-<br>10.35) | SGVRLWATRQAMLGQVHEVPEGWLIFVAEQEELYVRV<br>QNGFRKVQLEARTPLPRGTDNEVAALQPPVVQLHDSN<br>PYPRREHPHPTARPWRADDILASPPRLPEPQPYPGAP<br>HHSSYVHLRPARPTSPPAHSHRDFQPVLHLVALNSPL<br>SGGMRGIRGADFQCFQQARAVGLAGTFRAFLSSRLQD<br>LYSIVRRADRAAVPIVNLKDELLFPSWEALFSGSEGP<br>LKPGARIFSFDGKDVLRHPTWPQKSVWHGSDPNGRRL<br>TESYCETWRTEAPSATGQASSLLGGRLLGQSAASCHH<br>AYIVLCIENSFMTASKDDDDDKGGGGSEPKSQDKTHT<br>CPPCPAPELLGGPSVFLFPPKPKDTLMISRTPEVTCV<br>VVDVSHEDPEVKFNWYVDGVEVHNAKTKPREEQYNST<br>YRVVSVLTVLHQDWLNGKEYKCKVSNKALPAPIEKTI<br>SKAKGQPREPQVYTLPPCRDELTKNQVSLWCLVKGFY<br>PSDIAVEWESNGQPENNYKTTPPVLDSDGSFFLYSKL<br>TVDKSRWQQGNVFSCSVMHEALHNHYTQKSLSLSPGK |
| Chain 2<br>(Fc with<br>hole<br>mutation:<br>pUV10.36<br>empty) | GGGGSEPKSQDKTHTCPPCPAPELLGGPSVFLFPPKP<br>KDTLMISRTPEVTCVVVDVSHEDPEVKFNWYVDGVEV<br>HNAKTKPREEQYNSTYRVVSVLTVLHQDWLNGKEYKC<br>KVSNKALPAPIEKTISKAKGQPREPQVCTLPPSRDEL<br>TKNQVSLSCAVKGFYPSDIAVEWESNGQPENNYKTTP<br>PVLDSDGSFFLVSKLTVDKSRWQQGNVFSCSVMHEAL<br>HNHYTQKSLSLSPGK |
| Image | Heterodimeric NC-1-Fc forms a trimer over the oligomerization domain of NC-1 as revealed by crosslinking of non-denatured protein; see FIG. 18 |
| Notes | Knob Fc has KiH mutations S354C/T366W and hole Fc has mutations Y349C/T366S/L368A/Y407V. An enterokinase cleavage site is present between NC-1 and the Fc domain. Enterokinase (EK) recognizes lysine which is preceded by 4 aspartic (DDDDK). The amino acid following K should not be proline. The enterokinase was made only for research purpose, i.e. to use the Fc as a tag for expression and purification while NC-1 shall be isolated post cleavage with entorkinase (EK). This strategy was previously designed for Fc-endostatin and works well. In contrast, for NC-1, the present inventors found this to be a |

TABLE 1-continued

Heterodimeric NC-1-Fc low yield procedure as a substantial part of NC-1 aggregates after digestion by EK. For clinical use, the enterokinase cleavage site should be removed. This was done in all subsequent constructs such as monomeric Fc backbones.
Could induce ADCC due to dimeric Fc component.
High yield after optimization, i.e. >2:1 NC-1-Fc(knob) to Fc hole ratio. Expression of NC-1-Fc(knob) and Fc (hole)
each alone and later heterodimerization via redox also failed due to aggregation of NC-1-Fc(knob) construct when expressed alone.

TABLE 2

Homodimeric NC-1-Fc

| | |
|---|---|
| Molecule # | 2 |
| Name | Homodimeric NC-1-Fc<br>Alias Homodimeric NC-1-Fc (KiH) |
| Chain 1<br>(NC-1-Fc<br>with knob<br>mutations:<br>Pr00129-<br>10.35) | SGVRLWATRQAMLGQVHEVPEGWLIFVAEQEELYVRVQNG<br>FRKVQLEARTPLPRGTDNEVAALQPPVVQLHDSNPYPRRE<br>HPHPTARPWRADDILASPPRLPEPQPYPGAPHHSSYVHLR<br>PARPTSPPAHSHRDFQPVLHLVALNSPLSGGMRGIRGADF<br>QCFQQARAVGLAGTFRAFLSSRLQDLYSIVRRADRAAVPI<br>VNLKDELLFPSWEALFSGSEGPLKPGARIFSFDGKDVLRH<br>PTWPQKSVWHGSDPNGRRLTESYCETWRTEAPSATGQASS<br>LLGGRLLGQSAASCHHAYIVLCIENSFMTASKDDDDKGG<br>GGSEPKSQDKTHTCPPCPAPELLGGPSVFLFPPKPKDTLM<br>ISRTPEVTCVVVDVSHEDPEVKFNWYVDGVEVHNAKTKPR<br>EEQYNSTYRVVSVLTVLHQDWLNGKEYKCKVSNKALPAPI<br>EKTISKAKGQPREPQVYTLPPCRDELTKNQVSLWCLVKGF<br>YPSDIAVEWESNGQPENNYKTTPPVLDSDGSFFLYSKLTV<br>DKSRWQQGNVFSCSVMHEALHNHYTQKSLSLSPGK |
| Chain 2<br>(NC-1-Fc<br>with hole<br>mutations:<br>Pr00129-<br>10.36) | SGVRLWATRQAMLGQVHEVPEGWLIFVAEQEELYVRVQNG<br>FRKVQLEARTPLPRGTDNEVAALQPPVVQLHDSNPYPRRE<br>HPHPTARPWRADDILASPPRLPEPQPYPGAPHHSSYVHLR<br>PARPTSPPAHSHRDFQPVLHLVALNSPLSGGMRGIRGADF<br>QCFQQARAVGLAGTFRAFLSSRLQDLYSIVRRADRAAVPI<br>VNLKDELLFPSWEALFSGSEGPLKPGARIFSFDGKDVLRH<br>PTWPQKSVWHGSDPNGRRLTESYCETWRTEAPSATGQASS<br>LLGGRLLGQSAASCHHAYIVLCIENSFMTASKDDDDKGG<br>GGSEPKSQDKTHTCPPCPAPELLGGPSVFLFPPKPKDTLM<br>ISRTPEVTCVVVDVSHEDPEVKFNWYVDGVEVHNAKTKPR<br>EEQYNSTYRVVSVLTVLHQDWLNGKEYKCKVSNKALPAPI<br>EKTISKAKGQPREPQVCTLPPSRDELTKNQVSLSCAVKGF<br>YPSDIAVEWESNGQPENNYKTTPPVLDSDGSFFLVSKLTV<br>DKSRWQQGNVFSCSVMHEALHNHYTQKSLSLSPGK |
| Image | See FIG. 19 |
| Notes | Knob Fc has KiH mutations S354C/T366W and hole Fc has mutations Y349C/T366S/L368A/Y407V. An enterokinase cleavage site is present between NC-1 and the Fc domain.<br>Forms aggregates, very poor expression ~3 mg/L after transient transduction with formation of several peaks indicating a heterogenous population of moelcules. Failed to produce larger amount of the recombinant molecule for further pre-clinical studies. |

TABLE 3

Heterodimeric Fc-Endostatin

| | |
|---|---|
| Molecule # | 3 |
| Name | Heterodimeric Fc Endostatin<br>Alias Fc(KiH)-ES |
| Chain 1<br>(Knob-<br>Fc-<br>Endo-<br>statin:<br>Pr00130-<br>10.37) | EPKSQDKTHTCPPCPAPELLGGPSVFLFPPKPKDTLMISR<br>TPEVTCVVVDVSHEDPEVKFNWYVDGVEVHNAKTKPREEQ<br>YNSTYRVVSVLTVLHQDWLNGKEYKCKVSNKALPAPIEKT<br>ISKAKGQPREPQVYTLPPCRDELTKNQVSLWCLVKGEYPS<br>DIAVEWESNGQPENNYKTTPPVLDSDGSFFLYSKLTVDKS<br>RWQQGNVFSCSVMHEALHNHYTQKSLSLSPGGGGGSGGGG<br>SHSHRDFQPVLHLVALNSPLSGGMRGIRGADFQCFQQARA<br>VGLAGTFRAFLSSRLQDLYSIVRRADRAAVPIVNLKDELL<br>FPSWEALFSGSEGPLKPGARIFSFDGKDVLRHPTWPQKSV<br>WHGSDPNGRRLTESYCETWRTEAPSATGQASSLLGGRLLG<br>QSAASCHHAYIVLCIENSFMTASK |
| Chain 2<br>(Fc<br>hole:<br>pUV10.38<br>empty) | EPKSQDKTHTCPPCPAPELLGGPSVFLFPPKPKDTLMISR<br>TPEVTCVVVDVSHEDPEVKFNWYVDGVEVHNAKTKPREEQ<br>YNSTYRVVSVLTVLHQDWLNGKEYKCKVSNKALPAPIEKT<br>ISKAKGQPREPQVCTLPPSRDELTKNQVSLSCAVKGFYPS<br>DIAVEWESNGQPENNYKTTPPVLDSDGSFFLVSKLTVDKS<br>RWQQGNVFSCSVMHEALHNHYTQKSLSLSPGGGGGSGGGG<br>S |
| Image | See FIG. 20 |
| Notes | Knob Fc has KiH mutations S354C/T366W and hole Fc has mutations Y349C/T366S/L368A/Y407V.<br>Of note, Endostatin constructs were conjugated via N-terminal conjugation to Fc(knob). Because, the prototypic Fc-Endostatin utilized was designed by Javaherian et al, was an N-terminal fusion protein to wild type IgG1 Fc linked via an EK digestion site.<br>This compound was used as reference for dimeric Endostatin in the present studies. See FIG. 21. |

TABLE 4

Monomeric NC-1-Fc

| | |
|---|---|
| Molecule # | 4 |
| Name | Monomeric NC-1-Fc<br>Alias NC-1-Fc(mono) |
| Chain 1<br>(NC-1<br>mono Fc:<br>Pr00175) | SGVRLWATRQAMLGQVHEVPEGWLIFVAEQEELYVRVQNG<br>FRKVQLEARTPLPRGTDNEVAALQPPVVQLHDSNPYPRRE<br>HPHPTARPWRADDILASPPRLPEPQPYPGAPHHSSYVHLR<br>PARPTSPPAHSHRDFQPVLHLVALNSPLSGGMRGIRGADF<br>QCFQQARAVGLAGTFRAFLSSRLQDLYSIVRRADRAAVPI<br>VNLKDELLFPSWEALFSGSEGPLKPGARIFSFDGKDVLRH<br>PTWPQKSVWHGSDPNGRRLTESYCETWRTEAPSATGQASS<br>LLGGRLLGQSAASCHHAYIVLCIENSFMTASKGGGGSGGG<br>GSAPELLGGPSVFLFPPKPKDTLYITREPEVTCVVVDSVH<br>EDPEVKFNWYVDGVEVHNAKTKPREEQYNSTYRVVSVLTV<br>LHQDWLNGKEYKCKVSNKALPAPIEKTISKAKGQPREPQV<br>YTLPPSRDELTKNQVSLTCLVKGFYPSDIAVEWESNGQPE<br>NNYKTTPPVLDSDGSFRLYSKLTVDKSRWQQGNVFSCSVM<br>HEALHNHYTQKSLSLSPGK |
| Image | Monomeric NC-1-Fc forms a trimer via NC-1 oligomerization domain. See FIG. 22. |

TABLE 4-continued

Monomeric NC-1-Fc

| | |
|---|---|
| Notes | Fc includes monomeric mutation F405R and YTE half life extension mutations M252Y/S254T/T256E. High yield. Monomeric Fc is not supposed to induce ADCC. However, trimerization over the NC-1 domain may convey higher affinity binding than one would expect from a "standard" monomeric Fc. |

TABLE 5

Monomeric Fc-Endostatin

| | |
|---|---|
| Molecule # | 5 |
| Name | Monomeric Fc-Endostatin Alias Fc(Mono)-ES |
| Chain 1 (Mono Fc-Endo-statin: Pr00176) | APELLGGPSVFLFPPKPKDTLYITREPEVTCVVVDVSHED PEVKFNWYVDGVEVHNAKTKPREEQYNSTYRVVSVLTVLH QDWLNGKEYKCKVSNKALPAPIEKTISKAKGQPREPQVYT LPPSRDELTKNQVSLTCLVKGFYPSDIAVEWESNGQPENN YKTTPPVLDSDGSFRLYSKLTVDKSRWQQGNVFSCSVMHE ALHNHYTQKSLSLSPGGGGSGGGGSHSHRDFQPVLHLVA LNSPLSGGMRGIRGADFQCFQQARAVGLAGTFRAFLSSRL QDLYSIVRRADRAAVPIVNLKDELLFPSWEALFSGSEGPL KPGARIFSFDGKDVLRHPTWPQKSVWHGSDPNGRRLTESY CETWRTEAPSATGQASSLLGGRLLGQSAASCHHAYIVLCI ENSFMTASK |
| Image | See FIG. 23 |
| Notes | Fc includes monomeric mutation F405R and YTE half life extension mutations M252Y/S254T/T256E. This molecule was engineered as the reference monomeric endostatin construct for back-to-back comparisons with NC-1-Fc(mono) |

TABLE 6

Additional constructs that failed

| | |
|---|---|
| Molecule # | 6 |
| Name | N and C-terminal NC-1-Fc fusion proteins using IgG1 wild type backbone, in analogy to Fc-Endostatin. |
| Image | See FIG. 24 |
| Notes | The production of N- and C-terminal conjugation of NC-1 to wild type Fc failed as described for molecule #2: homodimeric NC-1-Fc(KiH). |
| Molecule # | 7 |
| Name | Heterodimeric proteins consisting of NC-1-Fc(knob) with Fc(hole) fused to different moieties including an IgG Fab fragment. |
| Image | See FIG. 25 |
| Notes | Low yield, aggregation and generation of a large number of products on SEC after protein A purification is shown. |

---

The invention claimed is:

1. A method for producing a protein oligomer comprising at least two heterodimeric human NC-1-Fc proteins, the method comprising:
   a) culturing a host cell expressing (i) a fusion protein comprising, from N- to C-terminus, human NC-1 from collagen 18 fused to human IgG1 Fc with "knob" mutations, or human IgG1 Fc with "knob" mutations fused to human NC-1 from collagen 18, and (ii) human IgG1 Fc with "hole" mutations, under conditions which allow the formation of a protein oligomer comprising at least two heterodimeric human NC-1-Fc proteins, and wherein the fusion protein of (i) and the human IgG1 Fc with "hole" mutations of (ii) are expressed in a ratio of 2:1 or higher,
   wherein the human IgG1 Fc with the "knob" mutations S354C/T366W comprises SEQ ID NO: 25, and the human IgG1 Fc with "hole" mutations Y349C/T366S/L368A/Y407V comprises SEQ ID NO: 26, and
   b) obtaining from the host cell of step a) the protein oligomer comprising at least two heterodimeric human NC-1-Fc proteins.

2. The method of claim 1, further comprising a step c) wherein the formation of a trimer is tested by crosslinking non-denatured heterodimeric human NC-1-Fc proteins.

3. The method of claim 1, wherein the protein oligomer comprises at least three heterodimeric human NC-1-Fc proteins.

* * * * *